US012577305B2

(12) United States Patent
Huang et al.

(10) Patent No.: US 12,577,305 B2
(45) **Date of Patent: *Mar. 17, 2026**

(54) MULTISPECIFIC ANTIGEN BINDING PROTEINS CAPABLE OF BINDING CD19 AND CD3, AND USE THEREOF

(71) Applicant: ITabMed (HK) Limited, Hong Kong (CN)

(72) Inventors: Zhihua Huang, Shanghai (CN); Wuzhong Shen, Shanghai (CN); Yiqun Rao, Shanghai (CN); Yumin Cui, Shanghai (CN); Xiaoqiang Yan, Shanghai (CN)

(73) Assignee: ITabMed (HK) Limited, Hong Kong (CN)

( * ) Notice: Subject to any disclaimer, the term of this patent is extended or adjusted under 35 U.S.C. 154(b) by 969 days.

This patent is subject to a terminal disclaimer.

(21) Appl. No.: 17/417,480

(22) PCT Filed: Dec. 23, 2019

(86) PCT No.: PCT/CN2019/127433
§ 371 (c)(1),
(2) Date: Jun. 23, 2021

(87) PCT Pub. No.: WO2020/135335
PCT Pub. Date: Jul. 2, 2020

(65) Prior Publication Data
US 2022/0064295 A1 Mar. 3, 2022

(30) Foreign Application Priority Data

Dec. 24, 2018 (WO) ................ PCT/CN2018/123108

(51) Int. Cl.
| | |
|---|---|
| *C07K 16/28* | (2006.01) |
| *A61K 39/00* | (2006.01) |
| *A61P 35/00* | (2006.01) |
| *A61P 35/02* | (2006.01) |

(52) U.S. Cl.
CPC .......... *C07K 16/2809* (2013.01); *A61P 35/00* (2018.01); *A61P 35/02* (2018.01); *C07K 16/2803* (2013.01); *A61K 2039/505* (2013.01); *C07K 2317/31* (2013.01); *C07K 2317/522* (2013.01); *C07K 2317/55* (2013.01); *C07K 2317/56* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,237,224 A | 12/1980 | Cohen et al. | |
| 4,485,045 A | 11/1984 | Regen | |
| 4,544,545 A | 10/1985 | Ryan et al. | |
| 4,676,980 A | 6/1987 | Segal et al. | |
| 4,683,195 A | 7/1987 | Mullis et al. | |
| 4,683,202 A | 7/1987 | Mullis | |
| 4,751,180 A | 6/1988 | Cousens et al. | |
| 4,816,567 A | 3/1989 | Cabilly et al. | |
| 4,935,233 A | 6/1990 | Bell et al. | |
| 4,946,778 A | 8/1990 | Ladner et al. | |
| 5,013,556 A | 5/1991 | Woodle et al. | |
| 5,030,719 A | 7/1991 | Umemoto et al. | |
| 5,151,510 A | 9/1992 | Stec et al. | |
| 5,283,173 A | 2/1994 | Fields et al. | |
| 5,468,614 A | 11/1995 | Fields et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,585,089 A | 12/1996 | Queen et al. | |
| 5,591,669 A | 1/1997 | Krimpenfort et al. | |
| 5,612,205 A | 3/1997 | Kay et al. | |
| 5,625,126 A | 4/1997 | Lonberg et al. | |
| 5,625,825 A | 4/1997 | Rostoker et al. | |
| 5,633,425 A | 5/1997 | Lonberg et al. | |
| 5,643,763 A | 7/1997 | Dunn et al. | |
| 5,661,016 A | 8/1997 | Lonberg et al. | |
| 5,693,761 A | 12/1997 | Queen et al. | |
| 5,693,792 A | 12/1997 | Torii et al. | |
| 5,703,057 A | 12/1997 | Johnston et al. | |
| 5,714,350 A | 2/1998 | Co et al. | |
| 5,721,367 A | 2/1998 | Kay et al. | |
| 5,733,743 A | 3/1998 | Johnson et al. | |

(Continued)

FOREIGN PATENT DOCUMENTS

| | | |
|---|---|---|
| CN | 101687915 A | 3/2010 |
| CN | 103842383 A | 6/2014 |

(Continued)

OTHER PUBLICATIONS

Janeway, 2001, Immunbiology, The generation of diversity in immunoglobulins.*
Townsend et al., 2016, Front. Immunol. vol. 7: 1-12.*
Rabia et al. 2018, Biochem. Eng. J. vol. 137: 365-374.*
Cui, Y. et al. (Nov. 29, 2018). "CD3-Activating Bi-Specific Antibody Targeting CD19 on B Cells in Mono- and Bi-Valent Format", Blood, American Society of Hematology 132(Supp. 1):4169, 2 pages.
Houdebine, L. M. (2009). "Production Of Pharmaceutical Proteins by Transgenic Animals," Comparative Immunology, Microbiology And Infectious Diseases 32(2):107-121.

(Continued)

*Primary Examiner* — Amy E Juedes

(74) *Attorney, Agent, or Firm* — MORRISON & FOERSTER LLP

(57) ABSTRACT

Provided are multispecific antigen binding proteins (MSAPs) that specifically bind to CD3 and CD19. Further provided are uses of the MSAPs for the preparation of pharmaceutical compositions, methods of treating cancer, and kits comprising the MSAPs.

26 Claims, 6 Drawing Sheets

Specification includes a Sequence Listing.

(56) References Cited

U.S. PATENT DOCUMENTS

| | | | |
|---|---|---|---|
| 5,736,137 A | 4/1998 | Anderson et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |
| 5,814,318 A | 9/1998 | Lonberg et al. |
| 5,837,458 A | 11/1998 | Minshull et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 5,959,083 A | 9/1999 | Bosslet et al. |
| 6,005,079 A | 12/1999 | Casterman et al. |
| 6,023,010 A | 2/2000 | Krimpenfort et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,255,458 B1 | 7/2001 | Lonberg et al. |
| 6,291,158 B1 | 9/2001 | Winter et al. |
| 6,291,161 B1 | 9/2001 | Lerner et al. |
| 6,326,193 B1 | 12/2001 | Liu |
| 6,410,319 B1 | 6/2002 | Raubitschek et al. |
| 6,423,498 B1 | 7/2002 | Markland et al. |
| 6,521,404 B1 | 2/2003 | Griffiths et al. |
| 6,982,321 B2 | 1/2006 | Winter |
| 7,087,409 B2 | 8/2006 | Barbas et al. |
| 7,109,003 B2 | 9/2006 | Hanson et al. |
| 7,115,717 B2 | 10/2006 | Mori et al. |
| 7,288,251 B2 | 10/2007 | Bedian et al. |
| 7,387,776 B2 | 6/2008 | Keler et al. |
| 7,429,644 B2 | 9/2008 | Garber et al. |
| 7,435,797 B2 | 10/2008 | Lowman et al. |
| 7,446,191 B2 | 11/2008 | Jensen |
| 7,462,352 B2 | 12/2008 | Hansen et al. |
| 7,514,537 B2 | 4/2009 | Jensen |
| 7,557,189 B2 | 7/2009 | Hoffee et al. |
| 7,723,482 B2 | 5/2010 | Soulillou et al. |
| 7,723,484 B2 | 5/2010 | Beidler et al. |
| 7,846,440 B2 | 12/2010 | Schoeberl et al. |
| 8,101,179 B2 | 1/2012 | Numazaki et al. |
| 8,236,308 B2 | 8/2012 | Kischel et al. |
| 8,709,421 B2 | 4/2014 | Heiss et al. |
| 8,784,821 B1 | 7/2014 | Kufer |
| 8,846,042 B2 | 9/2014 | Zhou |
| 8,884,602 B2 | 11/2014 | Utsunomiya |
| 9,718,893 B2 | 8/2017 | Jung |
| 10,428,155 B2 | 10/2019 | Moore et al. |
| 10,870,701 B2 | 12/2020 | Cui et al. |
| 11,013,800 B2 | 5/2021 | Zhou |
| 11,304,975 B2 | 4/2022 | Galetto et al. |
| 11,987,633 B2 | 5/2024 | Kufer et al. |
| 2002/0086014 A1 | 7/2002 | Korman et al. |
| 2002/0142359 A1 | 10/2002 | Copley et al. |
| 2003/0157054 A1 | 8/2003 | Gillies et al. |
| 2005/0033029 A1 | 2/2005 | Lu |
| 2005/0112694 A1 | 5/2005 | Carter et al. |
| 2005/0118183 A1 | 6/2005 | Hoffee et al. |
| 2005/0208043 A1 | 9/2005 | Adams et al. |
| 2005/0232919 A1 | 10/2005 | Grasso et al. |
| 2006/0165686 A1 | 7/2006 | Elson et al. |
| 2006/0177896 A1 | 8/2006 | Mach et al. |
| 2007/0059298 A1 | 3/2007 | Volkmann |
| 2007/0065431 A1 | 3/2007 | Coia et al. |
| 2007/0077246 A1 | 4/2007 | Koenig et al. |
| 2007/0148718 A1 | 6/2007 | Medghalchi et al. |
| 2007/0161783 A1 | 7/2007 | Barbosa et al. |
| 2007/0274981 A1 | 11/2007 | Sun et al. |
| 2007/0287170 A1 | 12/2007 | Davis et al. |
| 2008/0044429 A1 | 2/2008 | Johnson et al. |
| 2008/0260731 A1* | 10/2008 | Bernett ............. C07K 16/2803 |
| | | 536/23.53 |
| 2008/0286272 A1 | 11/2008 | Lackmann et al. |
| 2009/0136485 A1 | 5/2009 | Chu |
| 2009/0155275 A1 | 6/2009 | Wu et al. |
| 2009/0191201 A1 | 7/2009 | Heiss et al. |
| 2009/0202433 A1 | 8/2009 | Chang et al. |
| 2009/0220501 A1 | 9/2009 | Fey |
| 2009/0232810 A1 | 9/2009 | Kraus et al. |
| 2009/0304710 A1 | 12/2009 | Park et al. |
| 2009/0304716 A1 | 12/2009 | Reinhardt et al. |
| 2010/0003253 A1 | 1/2010 | Laeremans et al. |
| 2010/0003258 A1 | 1/2010 | Weng et al. |
| 2010/0025177 A1 | 2/2010 | Fukushima et al. |
| 2010/0065818 A1 | 3/2010 | Kim et al. |
| 2010/0092491 A1 | 4/2010 | Anastasi et al. |
| 2010/0150918 A1 | 6/2010 | Kufer et al. |
| 2010/0183615 A1 | 7/2010 | Kufer et al. |
| 2010/0189722 A1 | 7/2010 | Heider et al. |
| 2010/0196364 A1 | 8/2010 | Kim et al. |
| 2010/0226922 A1 | 9/2010 | Maetzel et al. |
| 2010/0239582 A1 | 9/2010 | Humphreys et al. |
| 2010/0310463 A1 | 12/2010 | Gunnarsson et al. |
| 2011/0028696 A1 | 2/2011 | Cardarelli et al. |
| 2011/0054151 A1 | 3/2011 | Lazar et al. |
| 2011/0059090 A1 | 3/2011 | Revets et al. |
| 2011/0064653 A1 | 3/2011 | Hansen et al. |
| 2011/0123529 A1 | 5/2011 | Laeremans et al. |
| 2012/0135110 A1 | 5/2012 | Chiba et al. |
| 2012/0244161 A1 | 9/2012 | Zugmeier et al. |
| 2012/0288275 A1 | 11/2012 | Zhang |
| 2012/0321626 A1 | 12/2012 | Zhou |
| 2015/0056206 A1 | 2/2015 | Zhou |
| 2015/0086550 A1 | 3/2015 | Heiss et al. |
| 2017/0174786 A1 | 6/2017 | Bacac et al. |
| 2019/0092862 A1 | 3/2019 | Cui et al. |
| 2019/0284279 A1 | 9/2019 | Kong et al. |
| 2020/0172627 A1 | 6/2020 | Bacac et al. |
| 2021/0070882 A1 | 3/2021 | Bacac et al. |
| 2021/0102001 A1 | 4/2021 | Zhou et al. |
| 2021/0214440 A1 | 7/2021 | Ganesan et al. |
| 2021/0301018 A1 | 9/2021 | Huang et al. |
| 2021/0393776 A1 | 12/2021 | Zhou et al. |

FOREIGN PATENT DOCUMENTS

| | | |
|---|---|---|
| CN | 104203981 A | 12/2014 |
| CN | 104592391 A | 5/2015 |
| CN | 104788567 A | 7/2015 |
| CN | 105378068 A | 3/2016 |
| CN | 107184977 A | 9/2017 |
| CN | 107636015 A | 1/2018 |
| CN | 107660151 A | 2/2018 |
| CN | 107903324 A | 4/2018 |
| CN | 108026177 A | 5/2018 |
| CN | 108690138 A | 10/2018 |
| CN | 110603266 A | 12/2019 |
| CN | 111484555 A | 8/2020 |
| CN | 111655733 A | 9/2020 |
| CN | 112794916 A | 5/2021 |
| EP | 0183070 A2 | 6/1986 |
| EP | 0244234 A2 | 11/1987 |
| EP | 0402226 A1 | 12/1990 |
| EP | 0463151 B1 | 6/1996 |
| EP | 0773288 A2 | 5/1997 |
| EP | 0546073 B1 | 9/1997 |
| EP | 0843961 B1 | 1/2007 |
| JP | 3068180 B2 | 7/2000 |
| JP | 3068506 B2 | 7/2000 |
| JP | 3068507 B2 | 7/2000 |
| JP | 2008-539177 A | 11/2008 |
| JP | 2009-511521 A | 3/2009 |
| JP | 2009131284 A | 6/2009 |
| JP | 2009526770 A | 7/2009 |
| JP | 2010-524435 A | 7/2010 |
| JP | 2010523096 A | 7/2010 |
| JP | 2011-501671 A | 1/2011 |
| JP | 2014-519322 A | 8/2014 |
| JP | 2015502373 A | 1/2015 |
| JP | 6400470 B2 | 9/2018 |
| JP | 2018533929 A | 11/2018 |
| JP | 7229566 B2 | 2/2023 |
| WO | WO-1991/00360 A1 | 1/1991 |
| WO | WO-1991/10741 A1 | 7/1991 |
| WO | WO-1992/01047 A1 | 1/1992 |

(56) References Cited

FOREIGN PATENT DOCUMENTS

| WO | WO-1992/03918 A1 | 3/1992 |
| WO | WO-1992/22645 A1 | 12/1992 |
| WO | WO-1992/22647 A1 | 12/1992 |
| WO | WO-1992/22670 A1 | 12/1992 |
| WO | WO-1993/08829 A1 | 5/1993 |
| WO | WO-1993/12227 A1 | 6/1993 |
| WO | WO-1994/00569 A1 | 1/1994 |
| WO | WO-1994/02602 A1 | 2/1994 |
| WO | WO-1994/04678 A1 | 3/1994 |
| WO | WO-1994/09131 A1 | 4/1994 |
| WO | WO-1994/11026 A2 | 5/1994 |
| WO | WO-1994/25585 A1 | 11/1994 |
| WO | WO-1994/25591 A1 | 11/1994 |
| WO | WO-1995/22618 A1 | 8/1995 |
| WO | WO-1996/14436 A1 | 5/1996 |
| WO | WO-1996/27011 A1 | 9/1996 |
| WO | WO-1996/33735 A1 | 10/1996 |
| WO | WO-1996/34096 A1 | 10/1996 |
| WO | WO-1996/34103 A1 | 10/1996 |
| WO | WO-1997/13852 A1 | 4/1997 |
| WO | WO-1998/24884 A1 | 6/1998 |
| WO | WO-1998/24893 A2 | 6/1998 |
| WO | WO-1999/37791 A1 | 7/1999 |
| WO | WO-2000/076310 A1 | 12/2000 |
| WO | 200129058 A1 | 4/2001 |
| WO | 200196584 A2 | 12/2001 |
| WO | WO-2002/077029 A2 | 10/2002 |
| WO | WO-2006/072620 A1 | 7/2006 |
| WO | WO-2006/095164 A1 | 9/2006 |
| WO | WO-2006/106959 A1 | 10/2006 |
| WO | WO-2006/114115 A1 | 11/2006 |
| WO | WO-2007/042261 A2 | 4/2007 |
| WO | WO-2007/065027 A2 | 6/2007 |
| WO | WO-2007/098934 A1 | 9/2007 |
| WO | WO-2008/024188 A2 | 2/2008 |
| WO | WO-2008/119566 A2 | 10/2008 |
| WO | WO-2008/119567 A2 | 10/2008 |
| WO | WO-2009/052081 A2 | 4/2009 |
| WO | WO-2009/068628 A1 | 6/2009 |
| WO | WO-2009/068630 A1 | 6/2009 |
| WO | WO-2009/149185 A2 | 12/2009 |
| WO | WO-2010/037836 A2 | 4/2010 |
| WO | WO-2010/037838 A2 | 4/2010 |
| WO | WO-2010/052014 A1 | 5/2010 |
| WO | WO-2010/069765 A1 | 6/2010 |
| WO | WO-2010/104949 A2 | 9/2010 |
| WO | WO-2010/145792 A1 | 12/2010 |
| WO | WO-2010/150918 A1 | 12/2010 |
| WO | 2011033105 A1 | 3/2011 |
| WO | WO-2011028683 A1 | 3/2011 |
| WO | WO-2011/079283 A1 | 6/2011 |
| WO | WO-2012/158818 A2 | 11/2012 |
| WO | WO-2014/012085 A2 | 1/2014 |
| WO | 2014110601 A1 | 7/2014 |
| WO | WO-2014/167022 A1 | 10/2014 |
| WO | WO-2016/055593 A1 | 4/2016 |
| WO | WO-2016/142314 A1 | 9/2016 |
| WO | WO-2016/189014 A1 | 12/2016 |
| WO | WO-2017/055314 A1 | 4/2017 |
| WO | WO-2017/157305 A1 | 9/2017 |
| WO | WO-2018/188612 A1 | 10/2018 |
| WO | WO-2020/048525 A1 | 3/2020 |
| WO | WO-2020/135335 A1 | 7/2020 |
| WO | 2024188355 A1 | 9/2024 |
| WO | 2025185760 A1 | 9/2025 |

OTHER PUBLICATIONS

Spiess, C. et al. (2015, e-pub. Jan. 27, 2015). "Alternative Molecular Formats and Therapeutic Applications for Bispecific Antibodies," Molecular Immunology 67(2):95-106.

Adams, et al. (2006, e-pub. Mar. 6, 2006). "Avidity-Mediated Enhancement of In vivo Tumor Targeting By Single-Chain Fv Dimers," Clin. Cancer Res. 12:1599-1605.

Adams, R.L.P. (Jul. 1969). "The Effect of Endogenous Pools of Thymidylate on the Apparent Rate of DNA Synthesis," Exp. Cell Res. 56(1):55-58.

Alarcon, B. et al. (Apr. 1991). "The CD3-γ And CD3-δ Subunits of the T Cell Antigen Receptor can be Expressed Within Distinct Functional TCR/CD3 Complexes," EMBO J. 10(4):903-912.

Alt, M. et al. (1999). "Novel Tetravalent And Bispecific IgG-Like Antibody Molecules Combining Single-Chain Diabodies With The Immunoglobulin γ1 Fc or CH3 region," FEES Letters 454:90-94.

Altschul, S.F. et al. (1990). "Basic Local Alignment Search Tool," J. Mol. Biol. 215(3):403-410.

Altschul, S.F. et al. (1997). "Gapped BLAST and PSI-BLAST: A New Generation of Protein Database Search Programs," Nucl. Acids Res. 25(17):3389-3402.

Amann, M. et al. (Jan. 1, 2008) "Therapeutic Window Of MuS110, A Single-Chain Antibody Construct Bispecific For Murine EpCAM and Murine CD3." Cancer Res. 68(1):143-151, 10 pages.

Anasetti, C. et al. (Dec. 1990). "Induction of Specific Nonresponsiveness in Unprimed Human T Cells by Anti-CD3 Antibody and Alloantigen," J. Exp. Med. 172(6):1691-1700.

Baldrick, P. (Oct. 2000). "Pharmaceutical Excipient Development: The Need For Preclinical Guidance," Regul. Toxicol Phaimacol. 32(2):210-218.

Bargou, R. et al. (Aug. 15, 2008). "Tumor Regression In Cancer Patients By Very Low Doses Of A T Cell-Engaging Antibody," Science 321(5981):974-977. (English Abstract Only).

Baxevanis, C. N. (2008). "Antibody-Based Cancer Therapy," Expert Opinion On Drug Discovery 3(4):441-452.

Beiboer, S.H.W. et al. (2000). "Guided Selection of a Pan Carcinoma Specific Antibody Reveals Similar Binding Characteristics Yet Structural Divergence Between the Original Murine Antibody and its Human Equivalent," J. Mol. Biol. (2000) 296(3):833-849.

Bellone, S. et al (Jan. 2016). "Solitomab, an EpCAM/CD3 Bispecific Antibody Construct (BITE), is Highly Active Against Primary Uterine Serous Papillary Carcinoma Cell Lines in Vitro", American Journal Of Obstetrics & Gynecology 214(1):99.e1-99.e8, 20 pages.

Bendig, M. M. (1995). "Humanization of Rodent Monoclonal Antibodies by CDR Grafting," Methods: A Companion to Methods in Enzymology 8:83-93.

Berger, C. et al. (Jan. 2008; e-pub. Dec. 3, 2007). "Adoptive Transfer of Effector CD8+ T Cells Derived From Central Memory Cells Establishes Persistent T Cell Memory in Primates," J. Clinical Investigation 118(1):294-305.

Beverley, P.C. et al. (Apr. 1981). "Distinctive Functional Characteristics of Human "T" Lymphocytes Defined by E Rosetting or a Monoclonal Anti-T Cell Antibody," Eur. J. Immunol. 11(4):329-334.

Biotecnol. "TribodyTM Technology," Located at <http://www.biotecnolcom/?tribody-technology>, last visited on Aug. 28, 2018, two pages.

Bird, R.E. et al. (Oct. 21, 1988). "Single-Chain Antigen-Binding Proteins," Science 242:423-426, 7 pages.

Bloom, L. et al. (Oct. 2009). "FN3: A New Protein Scaffold Reaches the Clinic," Drug Discovery Today 14(19-20):949-955.

Bobo, R.H. et al. (Mar. 15, 1994). "Convection-Enhanced Delivery of Macromolecules in the Brain," Proc. Natl. Acad. Sci. USA 91(6):2076-2080.

Boerner, P. et al. (Jul. 1, 1991). "Production of Antigen-Specific Human Monoclonal Antibodies From In Vitro-Primed Human Splenocytes," J. Immunol. 147(1):86-95.

Borden, P. et al. (Apr. 1, 1987). "Nucleotide Sequence of the cDNAs Encoding the Variable Region Heavy and Light Chains of a Myeloma Protein Specific for the Terminal Nonreducing End of Alpha (1 →6)Dextran," PNAS 84(8):2440-2443.

Bottaro, D.P. et al. (1991). "Identification of the Hepatocyte Growth Factor Receptor as the c-met Proto-Oncogene Product," Science 251(4995):802-804.

Bradley, P. et al. (Sep. 16, 2005). "Toward High-Resolution De Novo Structure Prediction For Small Proteins," Science 309(5742):1868-1871, 5 pages.

Brennan, M. et al. (Jul. 5, 1985). "Preparation of Bispecific Antibodies by Chemical Recombination of Monoclonal Immunoglobulin G1 Fragments," Science 229:81-83.

(56)          References Cited

OTHER PUBLICATIONS

Brooks, B.R. et al. (1983). "CHARMM: A Program For Macromolecular Energy, Minimization, and Dynamics Calculations," J. Comput. Chem. 4(2):187-217.

Bruggemann, M. et al. (1993). "Designer Mice: The Production of Human Antibody Repertoires in Transgenic Animals," Year in Immunol. 7:33-40.

Burbaum, J.J. et al. (1990). "Understanding Structural Relationships of Proteins of Unsolved Three-Dimensional Structure," Proteins 7(2):99-111.

Calaycay, J. et al. (Oct. 5, 1985). "Primary Structure of a DNA- And Heparin-Binding Domain (Domain III) in Human Plasma Fibronectin," J. Biol. Chem. 260(22):12136-12141.

Caron, P.C. et al. (1992; e-pub. Oct. 1, 1992). "Engineered Humanized Dimeric Forms of IgG Are More Effective Antibodies," J. Exp Med. 176:1191-1195.

Carpenter et al. (Apr. 15, 2002). "A Humanized Non-FcR-binding anti-CD3 Antibody, Visilizumab, For Treatment Of Steroid-Refractory Acute Graft-Versus-Host Disease," Blood 99(5):2712-2719.

Carter, P. et al. (Feb. 1992). "High Level *Escherichia coli* Expression and Production of a Bivalent Humanized Antibody Fragment," BioTechnology 10:163-167.

Chames, et al. (Apr. 2009). "Bispecific Antibodies For Cancer Therapy: The Light At The End Of The Tunnel?" mAbs 1(6):539-547.

Chang, et al. (May 2002). "Molecular Advances in Pretargeting Radioimmunotherapy with Bispecific Antibodies[1]," Mol Cancer Ther. 1:553-563.

Charman, W.N. (2000, e-pub. Aug. 2000). "Lipids, Lipophilic Drugs, and Oral Drug Delivery—Some Emerging Concepts," Journal of Pharmaceutical Sciences 89(8):967-978.

Chatzigeorgiou, A. et al. (Dec. 2009, e-pub. Nov. 2009). "CD40/CD40L Signaling and Its Implication in Health and Disease," Biofactors. 35(6):474-483.

Chaudhary, V.K. et al. (Feb. 1990). "A Rapid Method of Cloning Functional Variable-Region Antibody Genes in *Escherichia coli* as Single-Chain Immunotoxins," Proc. Natl. Acad. Sci. U.S.A. 87(3):1066-1070.

Chetty, R. et al. (1994). "CD3: Structure, Function, and Role of Immunostaining in Clinical Practice," J Pathol. 173(4):303-307.

Chiswell, D.J. et al. (1992). "Phage Antibodies: Will New 'Coliclonal' Antibodies Replace Monoclonal Antibodies?," Trends in Biotechnology 10:80-84.

Chothia, C. et al. (1987). "Canonical Structures for the Hypervariable Regions of Immunoglobulins," J. Mol. Biol. 196(4):901-917, 18 pages.

Chothia, C. et al. (Dec. 21-28, 1989). "Conformations of Immunoglobulin Hypervariable Regions," Nature 342(6252):877-883.

Clackson, T. et al. (Aug. 15, 1991). "Making Antibody Fragments Using Phage Display Libraries," Nature 352(6336):624-628.

Coloma, M. J. et al. (Feb. 1997). "Design And Production Of Novel Tetravalent Bispecific Antibodies," Nat. Biotechnol. 15:159-163.

Conrad, M.L. et al. (2007; e-pub. Jul. 25, 2007). "TCR and CD3 Antibody Cross-Reactivity in 44 Species," Cytometry (Part A) 71A:925-933.

Cote, R.J. et al. (Apr. 1983). "Generation of Human Monoclonal Antibodies Reactive With Cellular Antigens," Proc Natl Acad Sci USA 80:2026-2030.

Cwirla, S.E. et al. (Aug. 1990). "Peptides on Phage: A Vast Library of Peptides for Identifying Ligands," PNAS USA 87:6378-6382.

Darke, P.L. et al. (Feb. 5, 1989). "Human Immunodeficiency Virus Protease. Bacterial Expression and Characterization of the Purified Aspartic Protease," J. Biol. Chem. 264(4):2307-2312.

Davidson, B.L. et al. (Mar. 1993). "A Model System For in Vivo Gene Transfer into the Central Nervous System Using An Adenoviral Vector," Nature Genetics 3:219-223.

Davies, D.R. et al. (Jul. 1990). "Antibody-Antigen Complexes," Annual Rev. Biochem. 59:439- 473.

Davis, J.H. et al. (2010, e-pub. Feb. 4, 2010). "SEEDbodies: Fusion Proteins Based On Strand-Exchange Engineered Domain (Seed) CH3 Heterodimers In An Fc Analogue Platform For Asymmetric Binders Or Immunofusions And Bispecific Antibodies," Protein Engineering, Design & Selection, 23(4):195-202.

Davis, L.H. et al. (Jun. 15, 1991). "Specific 33-Residue Repeat(s) Erythrocyte Ankyrin Associate with the Anion Exchanger," J. Biol. Chem. 266(17):11163-11169.

Dayhoff, M.O. et al. (1978). "A Model Of Evolutionary Change in Proteins," Chapter 22 in Atlas of Protein Sequence and Structure, National Biomedical Research Foundation, Washington DC, 5(3):345-352.

Demydenko, D. et al. (Jun. 2009) "Expression Of Galectin-1 In Malignant Tumors," Exp Oncol. 31(2):74-79.

Deyev, S.M. et al. (2008, e-pub. 2008). "Multivalency: The Hallmark Of Antibodies Used For Optimization Of Tumor Targeting By Design," BioEssays 30:904-918.

Dietz, H. et al. (Jan. 31, 2006). "Protein Structure by Mechanical Triangulation," Proc. Nat. Acad. Sci. USA 103(5):1244-1247.

Dodson, E.J. (Nov. 7-8, 2007). "Computational Biology: Protein Predictions," Nature 450:176-177.

Donate, L.E. et al. (Dec. 1994). "Molecular Evolution and Domain Structure of Plasminogen-related Growth Factors (HGF/SF and HGF1/MSP)," Prat. Sci. 3(12):2378-2394.

Dong, J. et al. (Feb. 11, 2011). "Stable IgG-like Bispecific Antibodies Directed Toward the Type I Insulin-like Growth Factor Receptor Demonstrate Enhanced Ligand Blockade and Anti-tumor Activity," Journal of Biological Chemistry, 286(6):4703-4717.

Ehrlich, P.H. et al. (1980). "Isolation of an Active Heavy-Chain Variable Domain From a Homogeneous Rabbit Antibody by Cathepsin B Digestion of the Aminoethylated Heavy Chain," Biochem 19(17):4091-4096.

Eisenfield, J. et al. (1991; e-published on Aug. 1991). "Constrained Optimization and Protein Structure Determination," Am. J. Physiol. 261:C376-386.

Eppstein, D.A. et al. (Jun. 1985). "Biological Activity of Liposome-Encapsulated Murine Interferon γ Is Mediated by a Cell Membrane Receptor," Proc. Natl. Acad. Sci. USA 82:3688-3692.

Fellouse, F.A. et al. (Aug. 24, 2004). "Synthetic Antibodies from a Four-Amino-Acid Code: A Dominant Role for Tyrosine in Antigen Recognition," PNAS 101(34):12467-12472.

Fishwild, D.M. et al. (Jul. 1996). "High-Avidity Human IgG$_K$ Monoclonal Antibodies from a Novel Strain of Minilocus Transgenic Mice," Nature Biotechnology 14:845-851.

Flaherty, D. K. (2012) Chapter 10 "Antibody Diversity, Immunology for Pharmacy" in Immunology for Pharmacy. St. Louis, Mo.: Elsevier, 12 pages.

Froimowitz, M. (Jun. 1, 1990). "The Development of Computer Simulations of the Geometries and Thermodynamics of Biological Molecules," Biotechniques 8(6):640-644.

Geller, A.I. et al. (Aug. 1993). "Long-Term Increases in Neurotransmitter Release From Neuronal Cells Expressing a Constitutively Active Adenylate Cyclase From a Herpes Simplex Virus Type 1 Vector," Proc Natl. Acad. Sci. U.S.A. 90:7603-7607.

Geller, A.I. et al. (Feb. 1990). "Infection of Cultured Central Nervous System Neurons With a Defective Herpes Simplex Virus 1 Vector Results in Stable Expression of *Escherichia coli* β-Galactosidase," Proc Natl. Acad. Sci. USA 87:1149-1153.

Geller, A.I. et al. (Feb. 1995). "An HSV-1 Vector Expressing Tyrosine Hydroxylase Causes Production and Release of I-DOPA from Cultured Rat Striatal Cells," J. Neurochem 64(2):487-496.

Gorman, C.M. et al. (Nov. 1982). "The Rous Sarcoma Virus Long Terminal Repeat is a Strong Promoter When Introduced Into a Variety of Eukaryotic Cells by DNA-Mediated Transfection," Proc Natl. Acad. Sci. U.S.A. 79:6777-6781.

Graham, F.L. et al. (Jul. 1977). "Characteristics of a Human Cell Line Transformed by DNA From Human Adenovirus Type 5," J. Gen Virol. 36(1):59-74.

Green, L.L. et al. (May 1994). "Antigen-Specific Human Monoclonal Antibodies From Mice Engineered With Human Ig Heavy And Light Chain YACs," Nature Genetics 7(1):13-21.

(56)　　　　　　　References Cited

OTHER PUBLICATIONS

Grosschedl, R. et al. (Jul. 1985). "Cell-Type Specificity of Immunoglobulin Gene Expression is Regulated By at Least Three DNA Sequence Elements," Cell 41(3):885-897.

Grosse-Hovest, L. et al. (2003). "A Recombinant Bispecific Single-Chain Antibody Induces Targeted, Supra-Agonistic CD28-Stimulation And Tumor Cell Killing," Eur.J. Immunol. 33:1334-1340.

Gruber, M. et al. (1994). "Efficient Tumor Cell Lysis Mediated by a Bispecific Single Chain Antibody Expressed in Escherichia coli," The Journal of Immunology 152(11):5368-5374.

Gunasekaran, K, et al. (Jun. 18, 2010). "Enhancing Antibody Fc Heterodimer Formation through Electrostatic Steering Effects: Applications to Bispecific Molecules and Monovalent IgG," Journal of Biological Chemistry 285(25):19637-19646.

Guss, B. et al. (Jul. 1986). "Structure of the IgG-Binding Regions of Streptococcal Protein G," EMBO J. 5(7):1567-1575.

Hamers-Casterman, C. et al. (Jun. 3, 1993). "Naturally Occurring Antibodies Devoid of Light Chains," Nature 363(6428):446-448.

Hanes, J. et al. (May 1997). "In Vitro Selection and Evolution of Functional Proteins by Using Ribosome Display," Proc Natl. Acad. Sci. U.S.A. 94:4937-4942.

Harris, W.J. (Nov. 1, 1995). "Therapeutic Monoclonals: Production of Humanized Monoclonal Antibodies for In Vivo Imaging and Therapy," Biochem. Soc. Transactions 23(4):1035-1038.

Hein, J. (1990). "Unified Approach to Alignment and Phylogenies," Methods in Enzymology 183:626-645.

Henikoff, S. et al. (Nov. 15, 1992). "Amino Acid Substitution Matrices from Protein Blocks," Proc. Natl. Acad. Sci. USA 89(22):10915-10919.

Herold. K.C. et al. (Feb. 1, 2003). "Activation of Human T Cells by FcR Nonbinding Anti-CD3 mAb, HOKT3$\gamma$1 (Ala-Ala)," J. Clin. Invest. 111(3):409-418.

Higgins, D.G. et al. (1989). "Fast and Sensitive Multiple Sequence Alignments on a Microcomputer," Comput Appl Biosci. 5(2):151-153.

Hirsch, R. et al. (Jun. 1988). "Effects of In Vivo Administration of Anti-T3 Monoclonal Antibody on T Cell Function in Mice: I. Immunosuppression if Transplantation Responses," J. Immunol. 140(11):3766-3772.

Hochman, J. et al. (1976). "Folding and Interaction of Subunits at the Antibody Combining Site," Biochem 15(12):2706-2710.

Holliger, P. et al. (Jul. 1993). ""Diabodies": Small Bivalent and Bispecific Antibody Fragments," Proceedings of the National Academy of Sciences 90:6444-6448.

Holt, L.J. et al. (Nov. 2003). "Domain Antibodies: Proteins for Therapy," Trends in Biotechnology 21(11):484-490.

Hongo, J.S. et al. (1995). "Development and Characterization of Murine Monoclonal Antibodies to the Latency-Associated Peptide of Transforming Growth Factor $\beta_1$," Hybridoma 14(3):253-260.

Hoogenboom, H.R. et al. (1992). "By-Passing Immunisation. Human Antibodies from Synthetic Repertoires of Germline Hh Gene Segments Rearranged in Vitro," Journal of Molecular Biology 227:381-388.

Hoogenboom, H.R. et al. (Dec. 1992). "Building Antibodies from their Genes," Immunol. Reviews 130(1):41-68.

Houdebine, L. M. (1994). "Production Of Pharmaceutical Proteins From Transgenic Animals," Journal Of Biotechnology 34(3):269-287.

Hurle, M.R. et al. (Aug. 1994)."Protein Engineering Techniques for Antibody Humanization," Current Opinion in Biotechnology 5:428-433.

Huse, W.D. et al. (Dec. 8, 1989). "Generation of a Large Combinatorial Library of the Immunoglobulin Repertoire in Phage Lambda," Science 246(4935):1275-1281.

Huston, J.S. et al. (Aug. 1988). "Protein Engineering of Antibody Binding Sites: Recovery of Specific Activity in an Anti-Digoxin Single-Chain Fv Analogue Produced in Escherichia coli," Proc. Natl. Acad. Sci. U.S.A. 85(16):5879-5883.

Hwang, K.J. et al. (Jul. 1980). "Hepatic Uptake and Degradation of Unilamellar Sphingomyelin/Cholesterol Liposomes: A Kinetic Study," Proc. Natl Acad. Sci. USA 77(7):4030-4034.

Inbar, D. et al. (Sep. 1972). "Localization of Antibody-Combining Sites Within the Variable Portions of Heavy and Light Chains," Proc. Nat. Acad. Sci. USA 69(9):2659-2662.

International Preliminary Report on Patentability Chapter I mailed Sep. 18, 2018 for International Application No. PCT/CN2017/076816, filed on Mar. 15, 2017, 7 pages.

International Preliminary Report on Patentability Chapter I mailed Mar. 9, 2021 for International Application No. PCT/CN2019/104680, filed on Sep. 6, 2019, 6 pages.

International Preliminary Report on Patentability issued Jun. 16, 2021, for Patent Application No. PCT/CN2018/123108 filed on Dec. 24, 2018, 6 pages.

International Preliminary Report on Patentability issued Jun. 16, 2021, for Patent Application No. PCT/CN2019/127433 filed on Dec. 23, 2019, 5 pages.

International Preliminary Report on Patentability mailed Nov. 28, 2013, for Patent Application No. PCT/US2012/038177 filed on May 16, 2012, 7 pages.

International Search Report and Written Opinion from the International Searching Authority mailed Sep. 24, 2019, for International Patent Application No. PCT/CN2018/123108 filed Dec. 24, 2018, 15 pages.

International Search Report and Written Opinion from the International Searching Authority mailed Mar. 18, 2020, for International Patent Application No. PCT/CN2019/127433 filed Dec. 23, 2019, 13 pages.

International Search Report mailed Nov. 14, 2012, Patent Application No. PCT/US2012/038177 filed on May 16, 2012, 10 pages.

International Search Report mailed on Dec. 17, 2019 for International Patent Application No. PCT/CN2019/104680, filed on Sep. 6, 2019, 7 pages.

International Search Report mailed on Jun. 21, 2017 for International Patent Application No. PCT/CN2017/076816, filed on Mar. 15, 2017, 6 pages.

Jakobovits, A. et al. (Mar. 18, 1993) "Germ-line Transmission and Expression of a Human-derived Yeast Artificial Chromosome," Nature 362:255-258.

Jakobovits, A. et al. (Mar. 1993). "Analysis of Homozygous Mutant Chimeric Mice: Deletion of The Immunoglobulin Heavy-chain Joining Region Blocks B-Cell Development and Antibody Production," Proceedings of the National Academy of Sciences 90:2551-2555.

Jansen, F.K. et al. (Feb. 1982). "Immunotoxins: Hybrid Molecules Combining High Specificity and Potent Cytotoxicity," Immunological Reviews 62(1):185-216.

Jiang, T. et al. (Dec. 21, 2004; e-pub Dec. 15, 2004). "Tumor Imaging by Means of Proteolytic Activation of Cell-Penetrating Peptides," Proc. Natl. Acad. Sci. U.S.A. 101(51):17867-17872.

Johnson, et al. (2010, e-pub. Apr. 9, 2020). "Effector Cell Recruitment with Novel Fv-based Dual-affinity Re-targeting Protein Leads to Potent Tumor Cytolysis and in Vivo B-cell Depletion," J Mol. Biol. 399:436-449.

Johnson, G. et al. (2003). "The Kabat Database and a Bioinformatics Example," Methods in Molecular Biology 248:1-25. (Abstract Only, 1 page).

Jones, P.T. et al. (May 29, 1986). "Replacing the Complementarity-Determining Regions in a Human Antibody with Those from a Mouse," Nature 321:522-525.

Kaplitt, M.G. et al. (Oct. 1994). "Long-Term Gene Expression and Phenotypic Correction Using Adeno-Associated Virus Vectors in the Mammalian Brain," Nature Genetics 8:148-154.

Kappel, C.A. et al. (Oct. 1, 1992). "Regulating Gene Expression In Transgenic Animals," Current Opinion In Biotechnology 3(5):548-553.

Killen J.A. et al. (Nov. 1984) "Specific killing of lymphocytes that cause experimental autoimmune myasthenia gravis by ricin toxin-acetylcholine receptor conjugates," J. Immunol. 133(5):2549-2553.

(56)　　　　　References Cited

OTHER PUBLICATIONS

Kini, R.M. et al. (1991, e-pub May 21, 2012). "Molecular Modeling of Proteins: A Strategy for Energy Minimization by Molecular Mechanics in the AMBER Force Field," J. Biomol. Struct. Dyn. 9(3):475-488, 16 pages.

Kipriyanov, S.M. et al. (1999). "Bispecific tandem diabody for tumor therapy with improved antigen binding and pharmacokinetics," J Mal. Biol., 293:41-56.

Kipriyanov, S.M. and Le Gall, F. (2004). "Recent Advances In The Generation Of Bispecific Antibodies For Tumor Immunotherapy," Curr. Opin. Drug Discov. Devel. 7:233-242.

Kipriyanov, S.M. et al. (Dec. 31, 1998). "Bispecific CD3xCD19 Diabody for T Cell-Mediated LYSIS of Malignant Human B Cells," Int. J. Cancer 77:763-772.

Klimka, A. et al. (Jun. 20, 2000). "Human Anti-CD30 Recombinant Antibodies by Guided Phage Antibody Selection Using Cell Panning," British Journal of Cancer 83(2):252-260.

Koch-Nolte, F. et al. (2007; e-pub. Jun. 15, 2007). "Single Domain Antibodies From Llama Effectively and Specifically Block T Cell Ecto-ADP-Ribosyltransferase ART2.2 in vivo," FASEB J. 21:3490-3498.

Kohler, G. et al. (Aug. 7, 1975). "Continuous Cultures of Fused Cells Secreting Antibody of Predefined Specificity," Nature 256:495-497.

Koide, A. et al. (2007). "Monobodies: Antibody Mimics Based on the Scaffold of the Fibronectin Type III Domain," Methods Mol. Biol. 352:95-109.

Koide, A. et al. (Dec. 11, 1998). "The Fibronectin Type III Domain as a Scaffold For Novel Binding Proteins," J. Mol. Biol. 284(4):1141-1151.

Kontermann, R.E. (Jan. 2005). "Recombinant bispecific antibodies for cancer therapy," Acta Pharmacol. Sin. 26(1):1-9.

Kostelny, S.A. et al. (Mar. 1, 1992). "Formation of a Bispecific Antibody by the Use of Leucine Zippers," The Journal of Immunology 148(5):1547-1553.

Kozbor, D. et al. (Dec. 1984). "A Human Hybrid Myeloma for Production of Human Monoclonal Antibodies," The Journal of Immunology 133(6):3001-3005.

Kozbor, D. et al. (Mar. 1983). "The Production of Monoclonal Antibodies From Human Lymphocytes, " Immunology Today 4(3):72-79.

La Rocca, G. et al. (Apr. 5, 2004; e-pub. Mar. 16, 2004). "Zymographic Detection and Clinical Correlations of MMP-2 And MMP-9 in Breast Cancer Sera," British J. of Cancer 90(7):1414-1421.

Laplanche, L.A. et al. (Nov. 25, 1986). "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates," Nucl. Acids Res. 14(22):9081-9093.

Lavasani, S. et al. (2007; e-pub. Dec. 14, 2006). "Monoclonal Antibody against T-Cell Receptor $\alpha\beta$ Induces Self-Tolerance in Chronic Experimental Autoimmune Encephalomyelitis," Scandinavian Journal of Immunology 65(1):39-47.

Lavie, G. et al. (Apr. 1, 2000). "Inhibition of the CD8+ T Cell-Mediated Cytotoxicity Reaction By Hypericin: Potential For Treatment Of T Cell-Mediated Diseases," International Immunology 12(4):479-486.

Le Gal La Salle, G. et al. (Feb. 12, 1993). "An Adenovirus Vector for Gene Transfer Into Neurons and Glia in the Brain," Science 259(5097):988-990.

Lee, C.V. et al. (2004). "Bivalent Antibody Phage Display Mimics Natural Immunoglobulin," Journal of Immunological Methods 284(1-2):119-132.

Lee, C.V. et al. (2004). "High-affinity Human Antibodies from Phage-displayed Synthetic Fab Libraries with a Single Framework Scaffold," Journal of Molecular Biology 340:1073-1093.

Li, J. et al. (Mar. 7, 2006). "Human Antibodies for Immunotherapy Development Generated via a Human B Cell Hybridoma Technology," PNAS 103(10):3557-3562.

Lindmark, R. et al. (Aug. 12, 1983). "Binding of Immunoglobulins To Protein A and Immunoglobulin Levels in Mammalian Sera," J. Immunol. Meth. 62(1):1-13.

Liu, A.Y. et al. (May 1987). "Chimeric Mouse-Human IgG1 Antibody That Can Mediate Lysis of Cancer Cells," Proc Natl Acad Sci U S A. 84(10):3439-3443.

Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.

Liu, R. et al. (Jun. 5, 2010). "Efficient Inhibition of Human B-cell Lymphoma in SCID Mice by Synergistic Antitumor Effect of Human 4-IBB Ligand/anti-CD20 Fusion Proteins and Anti-CD3/anti-CD20 Diabodies," J Immunother. 33(5):500-509.

Lonberg, N. et al. (1995). "Human Antibodies from Transgenic Mice," International Reviews of Immunology. 13(1):65-93.

Lonberg, N. et al. (Apr. 28, 1994). "Antigen-Specific Human Antibodies from Mice Comprising Four Distinct Genetic Modifications," Nature 368:856-859.

Lu, D. et al. (2002). "Fab-scFv Fusion Protein: An Efficient Approach to Production of Bispecific Antibody Fragments," Journal of Immunological Methods 267:213-226.

Lybrand, T.P. (Jan.-Feb. 1991). "Molecular Simulation and Drug Design," J. Pharm. Belg. 46(1):49-54. (Abstract Only, 1 page).

Mabry, R. et al. (2010, e-pub. Dec. 18, 2009). "Engineering Of Stable Bispecific Antibodies Targeting IL-17A and IL-23," Protein Eng Des Sel. 23(3):115-127.

Mack, M. et al. (Jul. 1995). "A Small Bispecific Antibody Construct Expressed As A Functional Single-Chain Molecule With High Tumor Cell Cytotoxic," Proc. Natl. Acad. Sci. USA. 92:7021-7025.

Maratea, D. et al. (1985). "Deletion and Fusion Analysis of the Phage $\varphi$ X174 Lysis Gene E.," Gene 40(1):39-46.

Marks, J.D. et al. (Dec. 1991). "By-Passing Immunization: Human Antibodies From V-Gene Libraries Displayed On Phage," Journal of Molecular Biology 222(3):581-597.

Marks, J.D. et al. (Jul. 1992). "By-Passing Immunization: Building High Affinity Human Antibodies By Chain Shuffling," Biotechnology 10(7):779-783.

Martin, F.J. et al. (Jan. 10, 1982). "Irreversible Coupling of Immunoglobulin Fragments to Preformed Vesicles," J. Biol. Chem. 257(1):286-288.

Marvin, J.S. et al. (Jun. 2005). "Recombinant Approaches to IgG-like Bispecific Antibodies," Acta Pharmacol. Sin. 26(6):649-658.

Mather, J.P. (Aug. 1980). "Establishment and Characterization of Two Distinct Mouse Testicular Epithelial Cell Lines," Biol. Reprod. 23(1):243-252.

Mather, J.P. et al. (1982). "Culture of Testicular Cells in Hormone-Supplemented Serum-Free Medium," Annals N.Y. Acad. Sci. 383:44-68.

Mau-Sorensen, M. et al. (May 2015, e-pub. Mar. 27, 2015). "A Phase I Trial of Intravenous Catumaxomab: A Bispecific Monoclonal Antibody Targeting EpCAM And the T Cell Coreceptor CD3," Cancer Chemotherapy And Pharmacology 75(5):1065-1073.

Merchant, M.A. et al. (Jul. 1998). "An efficient route to human bispecific IgG," Nat Biotechnol. 16:677-681.

Mertens, N. et al. (2004). "New Strategies in Polypeptide and Antibody Synthesis: An Overview," Cancer Biotherapy & Radiopharmaceuticals 19(1):99-109.

Meylan, F. et al. (Jul. 18, 2008; Jun. 19, 2008). "The TNF-Family Receptor DR3 is Essential for Diverse T cell-mediated Inflammatory Diseases," Immunity 29(1):79-89, twenty six pages.

Michaelson, J.S. et al. (Mar./Apr. 2009). "Anti-Tumor Activity Of Stability-Engineered IgG-like Bispecific Antibodies Targeting TRAIL-R2 and LTbetaR," mAbs, 1:2:128-141.

Miller, B.R. et al. (2010, e-pub. May 10, 2010). "Stability engineering of scFvs for the development of bispecific and multivalent antibodies," Protein EnR Des Sel. 23(7):549-557.

Milstein, C. et al. (Oct. 6, 1983). "Hybrid Hybridomas and their use in Immunohistochemistry," Nature 305:537-540.

Morrison, P.F. et al. (1994). "High Flow Microinfusion: Tissue Penetration and Pharmacodynamics," Am. J. Physiol. 266:R292-R305.

Morrison, S.L. (Apr. 28, 1994). "Success in Specification," Nature 368:812-813.

(56)  References Cited

OTHER PUBLICATIONS

Morrison, S.L. et al. (Nov. 1984). "Chimeric Human Antibody Molecules: Mouse Antigen-binding Domains with Human Constant Region Domains," Proc. Nat'l Acad. Sci 81:6851-6855.

Muller, D. et al. (2010). "Bispecific Antibodies for Cancer Immunotherapy: Current Perspectives," Biodrugs 24(2):89-98.

Munson, P.J. et al. (1980). "Ligand: A Versatile Computerized Approach for Characterization of Ligand-binding Systems," Analytical Biochemistry 107:220-239.

Munz, M. et al. (Nov. 2, 2010) "Side-by-side analysis of five clinically tested anti-EpCAM monoclonal antibodies." Cancer Cell Int. 10(44):1-12.

Murphy, J.R. et al. (Nov. 1986). "Genetic Construction, Expression, and Melanoma-Selective Cytotoxicity of a Diphtheria Toxin-Related Alpha-Melanocyte-Stimulating Hormone Fusion Protein," Proc. Natl. Acad. Sci. USA 83(21):8258-8262.

Myers, E.W. et al. (1988). "Optimal Alignments in Llinear Space," Comput Appl Biosci. 4(1):11-17.

Needleman, S.B. et al. (Mar. 28, 1970). "A General Method Applicable to the Search for Similarities in the Amino Acid Sequence of Two Proteins," J. Mol. Biol. 48(3):443-453.

Nelson, A.L. et al. (Oct. 2010; e-pub Sep. 3, 2010). "Development Trends for Human Monoclonal Antibody Therapeutics," Nature Reviews Drug Discovery 9(10):767-774.

Neuberger, M. (Jul. 1996). "Generating High-Avidity Human Mabs In Mice," Nature Biotechnology 14:826, one page.

Nguyen, V.K. et al. (Apr. 2002; Feb. 26, 2002). "Heavy-Chain Antibodies in Camelidae; A Case of Evolutionary Innovation," Immunogenetics 54(1):39-47.

Nguyen, V.K. et al. (Jan. 23, 1998). "The Specific Variable Domain of Camel Heavy-Chain Antibodies is Encoded in the Germline," J. Mol. Biol. 275(3):413-418.

Nilson, B.H.K. at al. (Feb. 5, 1992). "Protein L From Peptostreptococcus Magnus Binds to the Kappa Light Chain Variable Domain," J. Biol. Chem. 267(4):2234-2239.

Obeidy, P. et al. (Dec. 2009, e-pub. Jul. 22, 2009). "NKG2D and its Ligands," Int J Biochem Cell Biol. 41(12):2364-2367.

O'Hare, M. et al. (Oct. 29, 1990). "Cytotoxicity of a Recombinant Ricin-A-Chain Fusion Protein Containing A Proteolytically-Cleavable Spacer Sequence," FEBS Lett. 273(1-2):200-204.

Okayama, H. et al. (Feb. 1983). "A cDNA Cloning Vector That Permits Expression of cDNA Inserts in Mammalian Cells," Molecular and Cellular Biology 3(2):280-289.

Olson, E.S. et al. (Mar. 2, 2010). "Activatable Cell Penetrating Peptides Linked to Nanoparticles as Dual Probes for In Vivo Fluorescence and MR Imaging of Proteases," Proc. Natl. Acad. Sci. USA 107(9):4311-4316.

Orcutt, K.D. et al. (2010, e-pub. Dec. 17, 2009). "A modular IgG-scFv Bispecific Antibody Topology," Protein Eng Des Sel. 23(4):221-228.

Ortho Multicenter Transplant Study Group "A Randomized Clinical Trial Of OKT3 Monoclonal Antibody For Acute Rejection Of Cadaveric Renal Transplants. Ortho Multicenter Transplant Study Group," N Engl. J Med., 313:337-342, (1985).

Otz, T. et al. (2009, e-pub. Oct. 2, 2008). "A Bispecific Single-Chain Antibody That Mediates Target Cell-Restricted, Supra-Agonistic CD28 Stimulation And Killing Of Lymphoma Cells," Leukemia, 23:71-77.

Parmley, S.F. et al. (1988). "Antibody-Selectable Filamentous fd Phage Vectors: Affinity Purification of Target Genes," Gene 73:305-318.

Paul, W.E. (ed.). (1993). "Fv Structure and Diversity in Three Dimensions," in Chapter 9 of Fundamental Immunology, 3rd Edition, Raven Press, 1185 Avenue of the Americas, New York, NY 10036, pp. 292-295, six pages.

Pearson, W.R. et al. (Apr. 1, 1988). "Improved Tools for Biological Sequence Comparison," Proc. Natl. Acad. Sci. USA 85(8):2444-2448.

Pedersen, L. (Sep. 1985). "Conformational Properties of Molecules by ab Initio Quantum Mechanical Energy Minimization," Environmental Health Perspectives 61:185-190.

Pessano, S. et al. (1985). "The T3/T Cell Receptor Complex: Antigenic Distinction Between The Two 20-kd T3 (T3-delta and T3-epsilon) Subunits," The EMBO J. 4(2):337-344.

Pluckthun, A. (Jun. 1991). "Antibody Engineering: Advances From the Use of Escherichia coli Expression Systems," Bio/Technology 9:545-551.

Pluckthun, A. (Oct. 4, 1990). "Antibodies from Escherichia coli," Nature 347(6292):497-498.

Portolano, S. et al. (Feb. 1, 1993). "Lack of Promiscuity in Autoantigen-Specific H and L Chain Combinations as Revealed by Human H and L Chain "Roulette"," The Journal of Immunology 150(3):880-887.

Powell, M.F. et al. (Sep.-Oct. 1998). "Compendium of Excipients for Parenteral Foimulations," PDA J Pharm Sci Technol. 52(5):238-311. (Abstract page only).

Prell, R.A. et al. (2013, e-pub. Jun. 28, 2013) "Catumaxomab (EpCAM/CD3 Multi-targeting Full-length Antibody)" Chpater 14 in Nonclinical Development of Novel Biologics, Biosimilars, Vaccines and Specialty Biologics, book, abstract only, 2 pages.

Presta, L.G. (1992). "Antibody Engineering," Current Opinion in Structural Biology 2:593-596.

Qian, B. et al. (Nov. 8, 2007). "High-Resolution Structure Prediction and the Crystallographic Phase Problem," Nature 450(7167):259-264, twenty three pages.

Rader, C. et al. (Jul. 21, 1998). "A Phage Display Approach for Rapid Antibody Humanization: Designed Combinatorial V Gene Libraries," Proc. Natl. Acad. Sci. USA 95(15):8910-8915.

Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.

Raman, S. et al. (Feb. 19, 2010). "NMR Structure Determination for Larger Proteins Using Backbone-Only Data," Science 327(5968):1014-1018, twelve pages.

Reff, M.E. (Oct. 1993). "High-Level Production of Recombinant Immunoglobulins in Mammalian Cells," Curr. Opinion Biotech. 4(5):573-576.

Reynolds, J.A. (1979). "Interaction of Divalent Antibody With Cell Surface Antigens," Biochemistry 18(2):264-269.

Ridgway, J.B.B. et al. (1996). "Knobs-Into-Holes' Engineering of Antibody CH3 Domains For Heavy Chain Heterodimerization," Protein Engineering 9(7):617-621.

Riechmann, L. et al. (Dec. 10, 1999). "Single Domain Antibodies: Comparison of Camel VH and Camelised Human VH Domains," J. Immunol. Methods 231(1-2):25-38.

Riechmann, L. et al. (Mar. 24, 1988). "Reshaping Human Antibodies for Therapy," Nature 332:323-327.

Robinson, D.F. (1971). "Comparison of Labeled Trees with Valency Three," Comb. Theor. 11:105-119.

Robinson, M.K. et al. (2008, e-pub. Oct. 7, 2008). "Targeting ErbB2 and ErbB3 with a bispecific single-chain Fv enhances targeting selectivity and induces a therapeutic effect in vitro," British Journal of Cancer 99:1415-1425.

Roux, K.H. et al. (Sep. 29, 1998). "Structural Analysis of the Nurse Shark (New) Antigen Receptor (NAR): Molecular Convergence of NAR and Unusual Mammalian Immunoglobulins," Proc. Natl. Acad. Sci. USA 95(20):11804-11809.

Rudikoff, S. et al. (Mar. 1982). "Single Amino Acid Substitution Altering Antigen-Binding Specificity," Proc. Natl. Acad. Sci. USA 79:1979-1983.

Russell, S.J. et al. (1993). "Retroviral Vectors Displaying Functional Antibody Fragments," Nucl. Acids Research 21(5):1081-1085.

Saitou, N. et al. (Jul. 1, 1987). "The Neighbor-Joining Method: A New Method For Reconstructing Phylogenetic Trees," Mol. Biol. Evol. 4(4):406-425.

Salmeron, A. et al. (Nov. 1, 1991). "A Conformational Epitope Expressed Upon Association of CD3-Epsilon With Either CD3-Delta Or CD3-Gamma Is The Main Target For Recognition By Anti-CD3 Monoclonal Antibodies," J. Immunol. 147(9):3047-3052.

(56)                    References Cited

OTHER PUBLICATIONS

Scatchard, G. (May 1949). "The Attractions of Proteins for Small Molecules and Ions," Annals of the New York Academy of Sciences 51(4):660-672.

Schaefer, W. et al. (Jul. 5, 2011; e-pub. Jun. 20, 2011). "Immunoglobulin Domain Crossover as a Generic Approach for the Production of Bispecific IgG Antibodies," Proc. Natl. Acad. Sci. USA 108(27):111870-111892.

Schmidt, M. et al. (Feb. 1, 2010, e-pub. Jul. 24, 2009). "An Open-Label, Randomized Phase II Study Of Adecatumumab, A Fully Human Anti-Epcam Antibody, As Monotherapy In Patients With Metastatic Breast Cancer," Annals Of Oncology 21(2):275-282.

Schoonjans, R. et al. (2000). "Fab Chains as an Efficient Heterodimerization Scaffold for the Production of Recombinant Bispecific and Trispecific Antibody Derivatives," Journal of Immunology 165:7050-7057.

Schueler-Furman, O. et al. (Oct. 28, 2005). "Progress in Modeling of Protein Structures and Interactions," Science 310(5748):638-642.

Schwartzberg, L.S. (Oct. 2001). "Clinical Experience With Edrecolomab: A Monoclonal Antibody Therapy For Colorectal Carcinoma," Critical Reviews In Oncology/ Hematology 40(1):17-24.

Scott, J.K. (Jul. 1992). "Discovering peptide ligands using epitope libraries," Trends in Biochemical Sciences 17(7):241-245.

Shalaby, M.F. et al. (Jan. 1992). "Development of Humanized Bispecific Antibodies Reactive with Cytotoxic Lymphocytes and Tumor Cells Overexpressing the HER2 Protooncogene," The Journal of Experimental Medicine 175:217-225.

Shen, H.M. et al. (Aug. 1, 2006). "TNF Receptor Superfamily-Induced Cell Death: Redox-Dependent Execution," FASEB J. 20(10):1589-1598.

Shen, J. et al. (2007, e-pub. Oct. 26, 2006). "Single Variable Domain Antibody As A Versatile Building Block For The Construction Of Igg-Like Bispecific Antibodies," J Immunol. Methods 318:65-74.

Shen, J. et al. (Apr. 21, 2006). "Single Variable Domain-Igg Fusion. A Novel Recombinant Approach To Fc Domain-Containing Bispecific Antibodies," J Biol. Chem. 281(16):10706-10714.

Sheriff, S. et al. (Sep. 1996). "Redefining the Minimal Antigen-binding Fragment," Nature Structural & Molecular Biology 3(9):733-736.

Shopes, B. (May 1, 1992). "A Genetically Engineered Human IgG Mutant With Enhanced Cytolytic Activity," J. Immunol. 148(9):2918-2922.

Sidhu, S.S. et al. (Apr. 2004). "Phage-displayed Antibody Libraries of Synthetic Heavy Chain Complementarity Determining Regions," Journal of Molecular Biology 338(2):299-310.

Smith, T.F. et al. (1981). "Comparison of Bio-Sequences," Adv. Appl. Math. 2:482-489.

Staerz, U.D. et al. (Mar. 1986). "Hybrid hybridoma producing a bispecific monoclonal antibody that can focus effector T-cell activity," Proc Natl Acad Sci USA, 83:1453-1457.

Stec, W.J. et al. (1984). "Automated Solid-Phase Synthesis, Separation, and Stereochemistry of Phosphorothioate Analogs of Oligodeoxyribonucleotides," J. Am. Chem. Soc. 106(20):6077-6079.

Stein, C.A. et al. (Apr. 25, 1988). "Physicochemical Properties of Phosphorothioate Oligodeoxynucleotides," Nucl. Acids Res. 16(8):3209-3221.

Stevenson, G.T. et al. (Mar. 1989). "A Chimeric Antibody With Dual Fc Regions (Bisfabfc) Prepared by Manipulations at the IgG Hinge," Anti-Cancer Drug Design 3(4):219-230.

Suresh, M.R. et al. (1986). "Bispecific Monoclonal Antibodies from Hybrid Hybridomas," Methods In Enzymology 121:210-228.

Third Party Observation submitted on Apr. 9, 2013 for International Application No. PCT/US2012/038177, filed on May 16, 2012, two pages.

Torkildsen, O. et al. (Mar. 24, 2006). "FcγR and Multiple Sclerosis: An Overview," Acta Neural Scand Suppl. 113(Suppl. 183):61-63.

Traunecker, A. et al. (1991). "Bispecific Single Chain Molecules (Janusins) Target Cytotoxic Lymphocytes on HIV Infected Cells," The EMBO Journal 10(12):3655-3659.

Trill, J.J. et al. (Oct. 1995). "Production of Monoclonal Antibodies in COS and CHO Cells," Curr. Opinion Biotech 6(5):553-560.

Turk, B.E. et al. (Jul. 1, 2001). "Determination of Protease Cleavage Site Motifs Using Mixture-Based Oriented Peptide Libraries," Nature Biotechnology 19:661-667.

Tutt, A. et al. (Jul. 1, 1991). "Trispecific F(Ab')3 Derivatives That Use Cooperative Signaling via the TCR/CD3 Complex and CD2 to Activate and Redirect Resting Cytotoxic T Cells," J. Immunol. 147(1):60-69.

Uhlmann, E. et al. (Jun. 1990). "Antisense Oligonucleotides: A New Therapeutic Principle," Chemical Reviews 90(4):543-584.

Urlaub, G. et al. (Jul. 1, 1980). "Isolation of Chinese Hamster Cell Mutants Deficient in Dihydrofolate Reductase Activity," Proc. Natl. Acad. Sci. USA 77(7):4216-4220.

Van Dijk, M.A et al. (2001). "Human Antibodies as Next Generation Therapeutics," Current Opinion in Chemical Biology 5:368-374.

Vaswani, S.K. et al. (Aug. 1998). "Humanized Antibodies as Potential Therapeutic Drugs," Annals of Allergy, Asthma & Immunology 81:105-119.

Vitetta, E.S. et al. (Nov. 20, 1987). "Redesigning Nature's Poisons to Create Anti-Tumor Reagents," Science 238:1098-1104.

Wall, R.J. (Jan. 1, 1996). "Transgenic Livestock: Progress And Prospects For The Future," Theriogenology 45(1):57-68.

Wang, W. (Aug. 1, 2000). "Lyophilization and Development of Solid Protein Pharmaceuticals," Int. J. Pharm. 203(1-2):1-60.

Weiner, S.J. et al.(Feb. 1984). "A New Force Field for Molecular Mechanical Simulation of Nucleic Acids and Proteins," J. Comput. Chem. 106(3):765-784.

Weisel, J.W. et al. (Dec. 20, 1985). "A Model for Fibrinogen: Domains and Sequence," Science 230(4732):1388-1391.

Westby, M. et al. (September-Oct. 1992). "Preparation and Characterization of Recombinant Proricin Containing an Alternative Protease-Sensitive Linker Sequence," Bioconjugate Chemistry 3(5):375-381.

Wilbur, W.J. et al. (Feb. 1, 1983). "Rapid Similarity Searches of Nucleic Acid and Protein Data Banks," Proc. Natl. Acad. Sci. USA 80(3):726-730.

Willems, A. et al. (2005, e-pub. May 13, 2005). "CD3 X CD28 Cross-Interacting Bispecific Antibodies Improve Tumor Cell Dependent T-Cell Activation," Cancer Immunol Immunother 54: 1059-1071.

Winter, G. et al. (Jun. 1993). "Humanized Antibodies," Immunol Today 14(6):243-246.

Wright, A. et al. (1992) "Genetically Engineered Antibodies: Progress And Prospects," Crit. Rev Immunol. 12(3-4)125-168.

Written Opinion of the International Searching Authority mailed on Dec. 17, 2019 for International Patent Application No. PCT/CN2019/104680, filed on Sep. 6, 2019, five pages.

Written Opinion of the International Searching Authority mailed on Jun. 21, 2017 for International Patent Application No. PCT/CN2017/076816, filed on Mar. 15, 2017, six pages.

Written Opinion of the International Searching Authority mailed on Nov. 14, 2012 for International Patent Application No. PCT/US2012/038177, filed on May 16, 2012, 5 pages.

Wu, C. et al. (Nov. 2007, e-pub. Oct. 14, 2007). "Simultaneous Targeting Of Multiple Disease Mediators By A Dual-Variable-Domain Immunoglobulin," Nat. Biotechnol. 25(11):1290-1297.

Wu, T.T. et al. (Aug. 1, 1970). "An Analysis of the Sequences of the Variable Regions of Bence Jones Proteins and Myeloma Light Chains and their Implications for Antibody Complementarity," J. Exp. Med. 132(2):211-250.

Wu, X. et al. (Mar. 16, 2015, e-pub. May 1, 2015). "Fab-based Bispecific Antibody Formats With Robust Biophysical Properties and Biological Activity," MABs. 7(3):470-482.

Xu, J. L. et al. (Jul. 2000). "Diversity in the CDR3 Region of VH Is Sufficient for Most Antibody Specificities," Immunity 13:37-45.

Yang, S.Y. et al. (Aug. 15, 1986). "A Common Pathway For T Lymphocyte Activation Involving Both the CD3-Ti Complex and CD2 Sheep Erythrocyte Receptor Determinants," J. Immunol. 137(4):1097-1100.

(56) References Cited

OTHER PUBLICATIONS

Yang, Y. et al. (Apr. 1995). "Cellular and Humoral Immune Responses to Viral Antigens Create Barriers to Lung-Directed Gene Therapy with Recombinant Adenoviruses," J. Virol. 69(4):2004-2015, 21 pages.

Yoshino, N. et al. (2000). "Upgrading of Flow Cytometric Analysis for Absolute Counts, Cytokines and Other Antigenic Molecules of Cynomolgus Monkeys (*Macaca fascicularis*) by Using Anti-Human Cross-Reactive Antibodies," Exp. Anim 49(2):97-110.

Zelensky, A.N. et al. (Dec. 2005; e-pub. Nov. 28, 2005). "The C-Type Lectin-Like Domain Superfamily," FEBS J. 272(24):6179-6217.

Zettlitz, K.A. (2010). "Protein A/G Chromatography," Chapter 34 in Antibody Engineering, Kontermann, R. (ed.) et al., Springer, Berlin, Heidelberg, 2nd Edition, Part V, 531-535.

Zhang, P. et al. (Feb. 1, 2014, e-pub. Nov. 1, 2013). "An EpCAM/CD3 Bispecific Antibody Efficiently Eliminates Hepatocellular Carcinoma Cells with Limited Galectin-1 Expression," Cancer Immunology Immunotherapy 63(2):121-132.

Zon, G. et al. (Dec. 1, 1991). "Phosphorothioate Oligonucleotides: Chemistry, Purification, Analysis, Scale-Up and Future Directions," Anti-Cancer Drug Design 6(6):539-568.

Beyer, B. M. et al. (2008, e-pub. Aug. 7, 2008). "Crystal Structures Of The Pro-Inflammatory Cytokine Interleukin-23 And Its Complex With A High-Affinity Neutralizing Antibody," Journal Of Molecular Biology 382 (4):942-955.

Li, W. et al. (2010). "Construction And Expression Of Anti-CD3/anti-CD19 Bispecific Diabody And Analyzing Its Specific Binding Activity," China Oncology 20(4):241-246 (English Abstract Only).

Schoonjans, R. et al. (2001). "A New Model For Intermediate Molecular Weight Recombinant Bispecific And Trispecific Antibodies By Efficient Heterodimerization Of Single Chain Variable Domains Through Fusion To A Fab-Chain," Biomolecular Engineering 17(6):193-202.

Herrera, A.F. et al. (Jul. 2018). "Investigational Antibody-Drug Conjugates For Treatment of B-lineage Malignancies," Clinical Lymphoma, Myeloma & Leukemia 18(7):452-468.

ClinicalTrials.gov (Aug. 21, 2025). "Trial of Mosunetuzumab (BTCT4465A) as Consolidation Therapy in Participants With Diffuse Large B-Cell Lymphoma Following First-Line Immunochemotherapy and as Monotherapy or in Combination With Polatuzumab Vedotin in Elderly/Unfit Participants With Previously Untreated Diffuse Large B-Cell Lymphoma," ClinicalTrials.gov ID No. NCT03677154, 33 pages.

ClinicalTrials.gov (Sep. 12, 2025). "A Safety, Efficacy and Pharmacokinetic Study of BTCT4465A (Mosunetuzumab) as a Single Agent and Combined With Atezolizumab in Non-Hodgkin's Lymphoma (NHL) and Chronic Lymphocytic Leukemia (CLL)," ClinicalTrials.gov ID No. NCT02500407, 20 pages.

Cuesta, A.M. et al. (May 4, 2010). "Multivalent Antibodies: When Design Surpasses Evolution," Trends Biotechnol. 28(7):355-362.

George, R.A. et al. (2002). "An Analysis of Protein Domain Linkers: Their Classification and Role in Protein Folding," Protein Eng. 15(11):871-879.

International Search Report and Written Opinion of the International Searching Authority mailed on Aug. 30, 2024 for PCT Application No. PCT/CN2024/082246, filed on Mar. 18, 2024, 18 pages.

International Search Report and Written Opinion of the International Searching Authority mailed on Jun. 16, 2025, for PCT Application No. PCT/CN2024/081471, filed on Mar. 8, 2025, 14 pages.

Kuhn, C. et al. (2016, e-pub. May 10, 2016). "Therapeutic Anti-CD3 Monoclonal Antibodies: From Bench To Bedside," Immunotherapy 8(8):889-906.

Mertens, N. (Jan. 2011). "Tribodies: Fab-scFv Fusion Proteins as a Platform to Create Multifunctional Pharmaceuticals," Bispecific Antibodies: 135-149.

Nerreter, T. et al. (2019). "Super-Resolution Microscopy Reveals Ultra-Low CD19 Expression on Myeloma Cells That Triggers Elimination by CD19 Car-T," Nature Communications 10:3137, 11 pages.

Schuster, S. J. et al. (Nov. 13, 2019). "Mosunetuzumab Induces Complete Remissions In Poor Prognosis Non-Hodgkin Lymphoma Patients, Including Those Who Are Resistant To Or Relapsing After Chimeric Antigen Receptor T-Cell (CAR-T) Therapies, And Is Active In Treatment Through Multiple Lines," Blood 134(6), 5 pages.

Tapia-Galisteo, A. et al. (Jan. 22, 2023). "When Three Is Not A Crowd: Trispecific Antibodies For Enhanced Cancer Immunotherapy," Theranostics 13(3):1028-1041.

Tu, G. et al. (Nov. 2023). "1188 In Vitro And In Vivo Characterization Of CD8+ T Cell Engagers (Tces) For Cancer Immunotherapy," J Immunother Cancer 2023;11(Suppl 1):A1308.

Ulrich H.W. et al. (2013). "The Intriguing Options of Multispecific Antibody Formats for Treatment of Cancer," Cancer Genomics & Proteomics 10:1-18.

Wang, S. et al. (Aug. 31, 2021). "Preclinical Characterization And Comparison Between CD3/CD19 Bispecific And Novel CD3/CD19/CD20 Trispecific Antibodies Against B-Cell Acute Lymphoblastic Leukemia: Targeted Immunotherapy For Acute Lymphoblastic Leukemia," Frontiers In Medicine 16(1):1-10.

Yang, Z et al. (Mar. 22, 2024). "Abstract 6704: Development And Characterization Of A Tri-Specific Selective CD8 T Cell Engager (CD8xCD3xCD19) For Treatment Of B Cell Lymphoma", Cancer Research 84(6):6704, 4 pages.

* cited by examiner

SEQUENCE LISTING

```
<160> NUMBER OF SEQ ID NOS: 61

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Ser Tyr Val Met His
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic Construct

<400> SEQUENCE: 2

Trp Ile Gly Tyr Ile Asn Pro Tyr Asn Asp Gly Thr Lys Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Gly Thr Tyr Tyr Tyr Gly Ser Arg Val Phe Asp Tyr
1               5                   10

<210> SEQ ID NO 4
<211> LENGTH: 16
```

<212> TYPE: PRT
<213> ORGANISM: Artificial Sequence
<220> FEATURE:
<223> OTHER INFORMATION: Synthetic Construct

<400> SEQUENCE: 4

```
Arg Ser Ser Lys Ser Leu Gln Asn Val Asn Gly Asn Thr Tyr Leu Tyr
1               5                   10                  15
```

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

```
Arg Met Ser Asn Leu Asn Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

```
Met Gln His Leu Glu Tyr Pro Ile Thr
1               5
```

<210> SEQ ID NO 7
<211> LENGTH: 121
<212> TYPE: PRT
<213> ORGANISM: Artificial Sequence
<220> FEATURE:
<223> OTHER INFORMATION: Synthetic Construct

<400> SEQUENCE: 7

```
Gln Val Gln Leu Val Gln Ser Gly Pro Glu Leu Ile Lys Pro Gly Gly
1               5                   10                  15

Ser Val Lys Met Ser Cys Lys Ala Ser Gly Tyr Thr Phe Thr Ser Tyr
                20                  25                  30

Val Met His Trp Val Arg Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ser Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Val Thr Val Ser Ser
            115                 120
```

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

```
Asp Val Val Met Thr Gln Ser Pro Ser Ser Ile Pro Val Thr Leu Gly
1               5                   10                  15

Glu Ser Val Ser Ile Ser Cys Arg Ser Ser Lys Ser Leu Gln Asn Val
            20                  25                  30

Asn Gly Asn Thr Tyr Leu Tyr Trp Phe Gln Gln Arg Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Pro Glu Asp Val Gly Val Tyr Tyr Cys Met Gln His
                85                  90                  95

Leu Glu Tyr Pro Ile Thr Phe Gly Ala Gly Thr Lys Leu Glu Ile Lys
            100                 105                 110

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Thr Tyr Ala Met Asn
1               5

<210> SEQ ID NO 10
<211> LENGTH: 19
<212> TYPE: PRT
<213> ORGANISM: Artificial Sequence
<220> FEATURE:
<223> OTHER INFORMATION: Synthetic Construct

<400> SEQUENCE: 10

Arg Ile Arg Ser Lys Tyr Asn Asn Tyr Ala Thr Tyr Tyr Ala Asp Ser
1               5                   10                  15

Val Lys Asp

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

<400> SEQUENCE: 11

His Gly Asn Phe Gly Asn Ser Tyr Val Ser Trp Phe Ala Tyr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Arg Ser Ser Thr Gly Ala Val Thr Thr Ser Asn Tyr Ala Asn
1               5                   10

<210> SEQ ID NO 13
<211> LENGTH: 7
```

-continued

<212> TYPE: PRT
<213> ORGANISM: Artificial Sequence
<220> FEATURE:
<223> OTHER INFORMATION: Synthetic Construct

<400> SEQUENCE: 13

Gly Thr Asn Lys Arg Ala Pro
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Ala Leu Trp Tyr Ser Asn Leu Trp Val
1               5

<210> SEQ ID NO 15
<211> LENGTH: 125
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 16
<211> LENGTH: 109
<212> TYPE: PRT
<213> ORGANISM: Artificial Sequence
<220> FEATURE:
<223> OTHER INFORMATION: Synthetic Construct

<400> SEQUENCE: 16

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

-continued

```
Ser Gly Ser Leu Leu Gly Gly Lys Ala Ala Leu Thr Leu Ser Gly Val
65              70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 17
<211> LENGTH: 249
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Met Val Thr Val Ser Ser Gly Gly Gly
                115                 120                 125

Gly Ser Gly Gly Gly Gly Ser Gly Gly Gly Gly Ser Gln Ala Val Val
        130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
                180                 185                 190

Thr Asn Lys Arg Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
        210                 215                 220

Glu Ala Glu Tyr Tyr Cys Ala Leu Trp Tyr Ser Asn Leu Trp Val Phe
225                 230                 235                 240

Gly Gly Gly Thr Lys Leu Thr Val Leu
                245

<210> SEQ ID NO 18
<211> LENGTH: 102
<212> TYPE: PRT
<213> ORGANISM: Artificial Sequence
<220> FEATURE:
<223> OTHER INFORMATION: Synthetic Construct

<400> SEQUENCE: 18

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser
            100
```

<210> SEQ ID NO 19
<211> LENGTH: 106
<212> TYPE: PRT
<213> ORGANISM: Artificial Sequence
<220> FEATURE:
<223> OTHER INFORMATION: Synthetic Construct

<400> SEQUENCE: 19

```
Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
        20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu
            100                 105
```

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

```
Gly Gly Ser Gly Gly Ser
1               5
```

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

```
Ser Gly Gly Gly Gly Ser
1               5
```

<210> SEQ ID NO 22
<211> LENGTH: 12

<212> TYPE: PRT
<213> ORGANISM: Artificial Sequence
<220> FEATURE:
<223> OTHER INFORMATION: Synthetic Construct

<400> SEQUENCE: 22

Gly Arg Ala Gly Gly Gly Gly Ala Gly Gly Gly Gly
1               5                   10

<210> SEQ ID NO 23
<211> LENGTH: 483
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser Gly Gly Gly
            115                 120                 125

Gly Ser Gly Gly Gly Gly Ser Gly Gly Gly Gly Ser Gln Ala Val Val
        130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
            180                 185                 190

Thr Asn Lys Arg Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Ala Leu Trp Tyr Ser Asn Leu Trp Val Phe
225                 230                 235                 240

Gly Gly Gly Thr Lys Leu Thr Val Leu Ser Gly Gly Gly Gly Ser Gln
                245                 250                 255

Val Gln Leu Val Gln Ser Gly Pro Glu Leu Ile Lys Pro Gly Gly Ser
            260                 265                 270

Val Lys Met Ser Cys Lys Ala Ser Gly Tyr Thr Phe Thr Ser Tyr Val
            275                 280                 285

Met His Trp Val Arg Gln Lys Pro Gly Gln Gly Leu Glu Trp Ile Gly
        290                 295                 300

Tyr Ile Asn Pro Tyr Asn Asp Gly Thr Lys Tyr Asn Glu Lys Phe Lys
305                 310                 315                 320

-continued

```
Gly Arg Ala Thr Leu Thr Ser Asp Lys Ser Ser Ser Thr Ala Tyr Met
            325                 330                 335

Glu Leu Ser Ser Leu Arg Ser Glu Asp Ser Ala Val Tyr Tyr Cys Ala
            340                 345                 350

Arg Gly Thr Tyr Tyr Tyr Gly Ser Arg Val Phe Asp Tyr Trp Gly Gln
            355                 360                 365

Gly Thr Thr Val Thr Val Ser Ser Ala Ser Thr Lys Gly Pro Ser Val
            370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
            405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
    450                 455                 460

Pro Ser Asn Thr Lys Val Asp Lys Lys Val Glu Pro Lys Ser Cys Pro
465                 470                 475                 480

Pro Cys Ser
```

```
<210> SEQ ID NO 24
<211> LENGTH: 223
<212> TYPE: PRT
<213> ORGANISM: Artificial Sequence
<220> FEATURE:
<223> OTHER INFORMATION: Synthetic Construct

<400> SEQUENCE: 24

Asp Val Val Met Thr Gln Ser Pro Ser Ser Ile Pro Val Thr Leu Gly
1               5                   10                  15

Glu Ser Val Ser Ile Ser Cys Arg Ser Ser Lys Ser Leu Gln Asn Val
            20                  25                  30

Asn Gly Asn Thr Tyr Leu Tyr Trp Phe Gln Gln Arg Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Pro Glu Asp Val Gly Val Tyr Tyr Cys Met Gln His
            85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys Pro Pro Cys Ser
    210                 215                 220
```

<210> SEQ ID NO 25
<211> LENGTH: 19
<212> TYPE: PRT
<213> ORGANISM: Artificial Sequence
<220> FEATURE:
<223> OTHER INFORMATION: Synthetic Construct

<400> SEQUENCE: 25

```
Met Glu Trp Ser Trp Val Phe Leu Phe Phe Leu Ser Val Thr Thr Gly
1               5                   10                  15

Val His Ser
```

<210> SEQ ID NO 26
<211> LENGTH: 57
<212> TYPE: DNA
<213> ORGANISM: Artificial Sequence
<220> FEATURE:
<223> OTHER INFORMATION: Synthetic Construct

<400> SEQUENCE: 26

```
atggaatgga gctgggtctt tctcttcttc ctgtcagtaa cgactggtgt ccactcc        57
```

<210> SEQ ID NO 27
<211> LENGTH: 672
<212> TYPE: DNA
<213> ORGANISM: Artificial Sequence
<220> FEATURE:
<223> OTHER INFORMATION: Synthetic Construct

<400> SEQUENCE: 27

```
gatgttgtga tgactcagtc tcccagcagc atccccgtga ccctgggcga gtctgtgtcc        60
atcagctgca gaagcagcaa gagcctgcag aacgtcaacg gcaacaccta cctgtactgg       120
ttccagcagc ggcctggcca gtctccccag ctgctgatct accggatgag caacctgaac       180
agcggcgtgc ccgatagatt ttctggctct ggcagcggca ccgacttcac cctgagaatc       240
tccggcgtgg aacccgagga cgtgggcgtg tactactgta tgcagcacct ggaataccc        300 atcaccttcg gagccggcac caagctggag atcaaacgta cggtggctgc accatctgtc       360
ttcatcttcc cgccatctga tgagcagttg aaatctggaa ctgcctctgt tgtgtgcctg       420
ctgaataact ctatcccag agaggccaaa gtacagtgga aggtggataa cgccctccaa        480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct tcaacagggg agagtgtcca       660
ccgtgctcct ag                                                          672
```

<210> SEQ ID NO 28
<211> LENGTH: 1452
<212> TYPE: DNA
<213> ORGANISM: Artificial Sequence
<220> FEATURE:
<223> OTHER INFORMATION: Synthetic Construct

<400> SEQUENCE: 28

```
gaggtgcagc tggtggagtc tgggggaggc ttggtacagc ctggggggtc cctgagactc        60
```

-continued

```
tcctgtgcag cctctggatt caccttttaac acctacgcca tgaactgggt ccgccaggct      120
ccagggaagg ggctggagtg ggtcgcacgc ataagaagta aatataataa ttatgcaaca      180
tattatgccg attcagtgaa agaccggttc accatctcca gagacgattc caagaacacg      240
ctgtatctgc aaatgaacag cctgagagcc gaggacacgg ccgtatatta ctgtgtgaga      300
catgggaact tcggtaatag ctacgtttcc tggtttgctt actggggcca agggacaatg      360
gtcaccgtct cttcaggtgg cggtggcagc ggcggtggtg ggtccggtgg cggcggatct      420
caggctgtgg tgactcagga gccctcactg actgtgtccc aggagggac agtcactctc       480 acctgtcgct caagtactgg ggctgttaca actagtaact atgccaactg ggtccagcag       540
aaacctggac aagcacccag gggtctgatt ggtggtacca caagcgagc tccaggtacc       600 cctgcccggt tctcaggctc cctccttggg ggcaaagctg ccctgacact gtcaggtgtg        660
cagcctgagg acgaggctga gtattactgc gctctatggt acagcaacct ctgggtgttc       720
ggcggaggga ccaagctgac cgtcctaagt ggcggtggag gatctcaggt gcagctggtg       780
cagtctggcc ccgagctaat caagcctggc ggcagcgtga gatgagctg caaggcctcc       840 ggctacacct tcaccagcta cgtgatgcac tgggtgcgcc agaagcctgg acagggcctg        900
gaatggatcg gctacatcaa cccctacaac gatggcacca gtacaacga gaagttcaag        960 ggcagagcca ccctgaccag cgacaagagc agcagcaccg cctacatgga actgagcagc       1020
ctgcggagcg aggacagcgc cgtgtactat tgtgccagag caacctacta ctacggcagc       1080
cgggtgttcg actactgggg acagggcacc acggtcaccg tctcctcagc tagcaccaag       1140
ggcccatccg tcttcccccct ggcaccctcc tccaagagca cctctggggg cacagcggcc      1200
ctgggctgcc tggtcaagga ctacttcccc gaaccggtga cggtgtcgtg gaactcaggc       1260
gccctgacca cgggcgtgca caccttcccg gctgtcctac agtcctcagg actctactcc       1320
ctcagcagcg tggtgaccgt gccctccagc agcttgggca cccagaccta catctgcaac       1380
gtgaatcaca agcccagcaa caccaaggtg gacaagaaag ttgagcccaa atcttgtcca       1440
ccgtgctcat ag                                                          1452
```

```
<210> SEQ ID NO 29
<211> LENGTH: 6
<212> TYPE: PRT
<213> ORGANISM: Artificial Sequence
<220> FEATURE:
<223> OTHER INFORMATION: Synthetic Construct

<400> SEQUENCE: 29

Gly Arg Ala Gly Gly Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Pro Leu Gly Leu Ala Gly
1               5

<210> SEQ ID NO 31
<211> LENGTH: 1
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1
<223> OTHER INFORMATION: Can be present in repeat of at least 1

<400> SEQUENCE: 31

Gly
1

<210> SEQ ID NO 32
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(2)
<223> OTHER INFORMATION: Can be present in repeat of at least 1

<400> SEQUENCE: 32

Gly Ser
1

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be present in repeat of at least 1

<400> SEQUENCE: 33

Gly Ser Gly Gly Ser
1               5

<210> SEQ ID NO 34
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(4)
<223> OTHER INFORMATION: Can be present in repeat of at least 1

<400> SEQUENCE: 34

Gly Gly Gly Ser
1

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be present in repeat of at least 1

<400> SEQUENCE: 35

Gly Gly Gly Gly Ser
1               5
```

-continued

```
<210> SEQ ID NO 36
<211> LENGTH: 2
<212> TYPE: PRT
<213> ORGANISM: Artificial Sequence
<220> FEATURE:
<223> OTHER INFORMATION: Synthetic Construct

<400> SEQUENCE: 36

Gly Gly
1

<210> SEQ ID NO 37
<211> LENGTH: 4
<212> TYPE: PRT
<213> ORGANISM: Artificial Sequence
<220> FEATURE:
<223> OTHER INFORMATION: Synthetic Construct

<400> SEQUENCE: 37

Gly Gly Ser Gly
1

<210> SEQ ID NO 38
<211> LENGTH: 5
<212> TYPE: PRT
<213> ORGANISM: Artificial Sequence
<220> FEATURE:
<223> OTHER INFORMATION: Synthetic Construct

<400> SEQUENCE: 38

Gly Gly Ser Gly Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Gly Ser Gly Ser Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct

<400> SEQUENCE: 40

Gly Ser Gly Gly Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Construct

<400> SEQUENCE: 41

Gly Gly Gly Ser Gly
1               5
```

```
<210> SEQ ID NO 42
<211> LENGTH: 5
<212> TYPE: PRT
<213> ORGANISM: Artificial Sequence
<220> FEATURE:
<223> OTHER INFORMATION: Synthetic Construct

<400> SEQUENCE: 42

Gly Ser Ser Ser Gly
1               5

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct

<400> SEQUENCE: 43

Gly Gly Gly Gly Ser Gly Gly Gly Ser Gly Gly Gly Gly Ser
1               5                   10                  15

<210> SEQ ID NO 44
<211> LENGTH: 5
<212> TYPE: PRT
<213> ORGANISM: Artificial Sequence
<220> FEATURE:
<223> OTHER INFORMATION: Synthetic Construct

<400> SEQUENCE: 44

Gly Gly Gly Gly Ser
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic Construct

<400> SEQUENCE: 45

Cys Pro Pro Cys
1

<210> SEQ ID NO 46
<211> LENGTH: 5
<212> TYPE: PRT
<213> ORGANISM: Artificial Sequence
<220> FEATURE:
<223> OTHER INFORMATION: Synthetic Construct

<400> SEQUENCE: 46

Cys Pro Pro Cys Ser
1               5

<210> SEQ ID NO 47
<211> LENGTH: 16
<212> TYPE: PRT
<213> ORGANISM: Artificial Sequence
<220> FEATURE:
<223> OTHER INFORMATION: Synthetic Construct

<400> SEQUENCE: 47

Arg Ser Ser Lys Ser Leu Gln Asn Val Asn Gly Asn Thr Tyr Leu Tyr
1               5                   10                  15
```

-continued

```
<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Arg Met Ser Asn Leu Asn Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Met Gln His Leu Glu Tyr Pro Leu Thr
1               5

<210> SEQ ID NO 50
<211> LENGTH: 112
<212> TYPE: PRT
<213> ORGANISM: Artificial Sequence
<220> FEATURE:
<223> OTHER INFORMATION: Synthetic Construct

<400> SEQUENCE: 50

Asp Val Val Met Thr Gln Ser Pro Ser Ser Ile Pro Val Thr Leu Gly
1               5                   10                  15

Glu Ser Val Ser Ile Ser Cys Arg Ser Ser Lys Ser Leu Gln Asn Val
            20                  25                  30

Asn Gly Asn Thr Tyr Leu Tyr Trp Phe Gln Gln Arg Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Pro Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110

<210> SEQ ID NO 51
<211> LENGTH: 248
<212> TYPE: PRT
<213> ORGANISM: Artificial Sequence
<220> FEATURE:
<223> OTHER INFORMATION: Synthetic Construct

<400> SEQUENCE: 51

Asp Val Val Met Thr Gln Ser Pro Ser Ser Ile Pro Val Thr Leu Gly
1               5                   10                  15

Glu Ser Val Ser Ile Ser Cys Arg Ser Ser Lys Ser Leu Gln Asn Val
            20                  25                  30

Asn Gly Asn Thr Tyr Leu Tyr Trp Phe Gln Gln Arg Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
```

-continued

```
65                  70                  75                  80

Ser Gly Val Glu Pro Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110

Gly Gly Gly Gly Ser Gly Gly Gly Ser Gly Gly Gly Gly Ser Gln
        115                 120                 125

Val Gln Leu Val Gln Ser Gly Pro Glu Leu Ile Lys Pro Gly Gly Ser
    130                 135                 140

Val Lys Met Ser Cys Lys Ala Ser Gly Tyr Thr Phe Thr Ser Tyr Val
145                 150                 155                 160

Met His Trp Val Arg Gln Lys Pro Gly Gln Gly Leu Glu Trp Ile Gly
                165                 170                 175

Tyr Ile Asn Pro Tyr Asn Asp Gly Thr Lys Tyr Asn Glu Lys Phe Lys
            180                 185                 190

Gly Arg Ala Thr Leu Thr Ser Asp Lys Ser Ser Ser Thr Ala Tyr Met
        195                 200                 205

Glu Leu Ser Ser Leu Arg Ser Glu Asp Ser Ala Val Tyr Tyr Cys Ala
    210                 215                 220

Arg Gly Thr Tyr Tyr Tyr Gly Ser Arg Val Phe Asp Tyr Trp Gly Gln
225                 230                 235                 240

Gly Thr Thr Val Thr Val Ser Ser
                245
```

```
<210> SEQ ID NO 52
<211> LENGTH: 104
<212> TYPE: PRT
<213> ORGANISM: Artificial Sequence
<220> FEATURE:
<223> OTHER INFORMATION: Synthetic Construct

<400> SEQUENCE: 52

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu
            100
```

```
<210> SEQ ID NO 53
<211> LENGTH: 485
<212> TYPE: PRT
<213> ORGANISM: Artificial Sequence
<220> FEATURE:
<223> OTHER INFORMATION: Synthetic Construct

<400> SEQUENCE: 53

Asp Val Val Met Thr Gln Ser Pro Ser Ser Ile Pro Val Thr Leu Gly
1               5                   10                  15
```

```
Glu Ser Val Ser Ile Ser Cys Arg Ser Ser Lys Ser Leu Gln Asn Val
            20                  25                  30

Asn Gly Asn Thr Tyr Leu Tyr Trp Phe Gln Gln Arg Pro Gly Gln Ser
            35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Pro Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110

Gly Gly Gly Gly Ser Gly Gly Gly Gly Ser Gly Gly Gly Ser Gln
            115                 120                 125

Val Gln Leu Val Gln Ser Gly Pro Glu Leu Ile Lys Pro Gly Gly Ser
    130                 135                 140

Val Lys Met Ser Cys Lys Ala Ser Gly Tyr Thr Phe Thr Ser Tyr Val
145                 150                 155                 160

Met His Trp Val Arg Gln Lys Pro Gly Gln Gly Leu Glu Trp Ile Gly
                165                 170                 175

Tyr Ile Asn Pro Tyr Asn Asp Gly Thr Lys Tyr Asn Glu Lys Phe Lys
            180                 185                 190

Gly Arg Ala Thr Leu Thr Ser Asp Lys Ser Ser Ser Thr Ala Tyr Met
            195                 200                 205

Glu Leu Ser Ser Leu Arg Ser Glu Asp Ser Ala Val Tyr Tyr Cys Ala
    210                 215                 220

Arg Gly Thr Tyr Tyr Tyr Gly Ser Arg Val Phe Asp Tyr Trp Gly Gln
225                 230                 235                 240

Gly Thr Thr Val Thr Val Ser Ser Gly Gly Gly Ser Glu Val Gln
                245                 250                 255

Leu Val Glu Ser Gly Gly Gly Leu Val Gln Pro Gly Gly Ser Leu Arg
            260                 265                 270

Leu Ser Cys Ala Ala Ser Gly Phe Thr Phe Asn Thr Tyr Ala Met Asn
            275                 280                 285

Trp Val Arg Gln Ala Pro Gly Lys Gly Leu Glu Trp Val Ala Arg Ile
    290                 295                 300

Arg Ser Lys Tyr Asn Asn Tyr Ala Thr Tyr Tyr Ala Asp Ser Val Lys
305                 310                 315                 320

Asp Arg Phe Thr Ile Ser Arg Asp Asp Ser Lys Asn Thr Leu Tyr Leu
            325                 330                 335

Gln Met Asn Ser Leu Arg Ala Glu Asp Thr Ala Val Tyr Tyr Cys Val
            340                 345                 350

Arg His Gly Asn Phe Gly Asn Ser Tyr Val Ser Trp Phe Ala Tyr Trp
            355                 360                 365

Gly Gln Gly Thr Met Val Thr Val Ser Ser Ala Ser Thr Lys Gly Pro
    370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
```

-continued

```
                435               440               445

Val Pro Ser Ser Ser Leu Gly Thr Gln Thr Tyr Ile Cys Asn Val Asn
    450               455               460

His Lys Pro Ser Asn Thr Lys Val Asp Lys Lys Val Glu Pro Lys Ser
465               470               475               480

Cys Pro Pro Cys Ser
                485

<210> SEQ ID NO 54
<211> LENGTH: 471
<212> TYPE: PRT
<213> ORGANISM: Artificial Sequence
<220> FEATURE:
<223> OTHER INFORMATION: Synthetic Construct

<400> SEQUENCE: 54

Asp Val Val Met Thr Gln Ser Pro Ser Ser Ile Pro Val Thr Leu Gly
1               5                   10                  15

Glu Ser Val Ser Ile Ser Cys Arg Ser Ser Lys Ser Leu Gln Asn Val
                20                  25                  30

Asn Gly Asn Thr Tyr Leu Tyr Trp Phe Gln Gln Arg Pro Gly Gln Ser
            35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Pro Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
                100                 105                 110

Gly Gly Gly Gly Ser Gly Gly Gly Gly Ser Gly Gly Gly Gly Ser Gln
            115                 120                 125

Val Gln Leu Val Gln Ser Gly Pro Glu Leu Ile Lys Pro Gly Gly Ser
    130                 135                 140

Val Lys Met Ser Cys Lys Ala Ser Gly Tyr Thr Phe Thr Ser Tyr Val
145                 150                 155                 160

Met His Trp Val Arg Gln Lys Pro Gly Gln Gly Leu Glu Trp Ile Gly
                165                 170                 175

Tyr Ile Asn Pro Tyr Asn Asp Gly Thr Lys Tyr Asn Glu Lys Phe Lys
                180                 185                 190

Gly Arg Ala Thr Leu Thr Ser Asp Lys Ser Ser Ser Thr Ala Tyr Met
            195                 200                 205

Glu Leu Ser Ser Leu Arg Ser Glu Asp Ser Ala Val Tyr Tyr Cys Ala
    210                 215                 220

Arg Gly Thr Tyr Tyr Tyr Gly Ser Arg Val Phe Asp Tyr Trp Gly Gln
225                 230                 235                 240

Gly Thr Thr Val Thr Val Ser Ser Gly Gly Gly Ser Gln Ala Val
                245                 250                 255

Val Thr Gln Glu Pro Ser Leu Thr Val Ser Pro Gly Gly Thr Val Thr
            260                 265                 270

Leu Thr Cys Arg Ser Ser Thr Gly Ala Val Thr Thr Ser Asn Tyr Ala
            275                 280                 285

Asn Trp Val Gln Gln Lys Pro Gly Gln Ala Pro Arg Gly Leu Ile Gly
    290                 295                 300

Gly Thr Asn Lys Arg Ala Pro Gly Thr Pro Ala Arg Phe Ser Gly Ser
```

```
305                310                315                320
Leu Leu Gly Gly Lys Ala Ala Leu Thr Leu Ser Gly Val Gln Pro Glu
                325                330                335

Asp Glu Ala Glu Tyr Tyr Cys Ala Leu Trp Tyr Ser Asn Leu Trp Val
                340                345                350

Phe Gly Gly Gly Thr Lys Leu Thr Val Leu Gly Gln Pro Lys Ala Ala
                355                360                365

Pro Ser Val Thr Leu Phe Pro Pro Ser Ser Glu Glu Leu Gln Ala Asn
        370                375                380

Lys Ala Thr Leu Val Cys Leu Ile Ser Asp Phe Tyr Pro Gly Ala Val
385                390                395                400

Thr Val Ala Trp Lys Ala Asp Ser Ser Pro Val Lys Ala Gly Val Glu
                405                410                415

Thr Thr Thr Pro Ser Lys Gln Ser Asn Asn Lys Tyr Ala Ala Ser Ser
                420                425                430

Tyr Leu Ser Leu Thr Pro Glu Gln Trp Lys Ser His Arg Ser Tyr Ser
        435                440                445

Cys Gln Val Thr His Glu Gly Ser Thr Val Glu Lys Thr Val Ala Pro
        450                455                460

Thr Glu Cys Pro Pro Cys Ser
465                470
```

```
<210> SEQ ID NO 55
<211> LENGTH: 1458
<212> TYPE: DNA
<213> ORGANISM: Artificial Sequence
<220> FEATURE:
<223> OTHER INFORMATION: Synthetic Construct

<400> SEQUENCE: 55
gatgttgtga tgactcagtc tcccagcagc atccccgtga ccctgggcga gtctgtgtcc      60
atcagctgca gaagcagcaa gagcctgcag aacgtcaacg gcaacaccta cctgtactgg     120
ttccagcagc ggcctggcca gtctccccag ctgctgatct accggatgag caacctgaac     180
agcggcgtgc ccgatagatt ttctggctct ggcagcggca ccgacttcac cctgagaatc     240
tccggcgtgg aacccgagga cgtgggcgtg tactactgta tgcagcacct ggaataccccc    300 ctgaccttcg gagccggcac caagctggag atcaaaggcg gaggcggtag tggcggtggt     360
ggttcaggcg gtggcggatc tcaggtgcag ctggtgcagt ctggccccga gctaatcaag     420
cctggcggca gcgtgaagat gagctgcaag gcctccggct acaccttcac cagctacgtg     480
atgcactggg tgcgccagaa gcctggacag ggcctggaat ggatcggcta catcaacccc     540
tacaacgatg gcaccaagta caacgagaag ttcaagggca gagccaccct gaccagcgac     600
aagagcagca gcaccgccta catggaactg agcagcctgc ggagcgagga cagcgccgtg     660
tactattgtg ccagaggcac ctactactac ggcagccggg tgttcgacta ctggggacag     720
ggcaccacgg tcaccgtctc ctcaggtggc ggaggatctg aggtgcagct ggtggagtct     780
gggggaggct tggtacagcc tggggggtcc ctgagactct cctgtgcagc ctctggattc     840
acctttaaca cctacgccat gaactgggtc cgccaggctc agggaaaggg ctggagtgg      900 gtcgcacgca taagaagtaa atataataat tatgcaacat attatgccga ttcagtgaaa     960
gaccggttca ccatctccag agacgattcc aagaacacgc tgtatctgca aatgaacagc    1020
ctgagagccg aggacacggc cgtatattac tgtgtgagac atgggaactt cggtaatagc    1080
tacgtttcct ggtttgctta ctggggccaa gggacaatgg tcaccgtctc ttcagctagc    1140
```

-continued

```
accaagggcc catccgtctt ccccctggca ccctcctcca agagcacctc tgggggcaca        1200
gcggccctgg gctgcctggt caaggactac ttccccgaac cggtgacggt gtcgtggaac        1260
tcaggcgccc tgaccagcgg cgtgcacacc ttcccggctg tcctacagtc ctcaggactc        1320
tactccctca gcagcgtggt gaccgtgccc tccagcagct tgggcaccca gacctacatc        1380
tgcaacgtga atcacaagcc cagcaacacc aaggtggaca agaaagttga gcccaaatct        1440
tgtccaccgt gctcatag                                                      1458

<210> SEQ ID NO 56
<211> LENGTH: 1416
<212> TYPE: DNA
<213> ORGANISM: Artificial Sequence
<220> FEATURE:
<223> OTHER INFORMATION: Synthetic Construct

<400> SEQUENCE: 56
gatgttgtga tgactcagtc tcccagcagc atccccgtga ccctgggcga gtctgtgtcc          60
atcagctgca gaagcagcaa gagcctgcag aacgtcaacg gcaacaccta cctgtactgg         120
ttccagcagc ggcctggcca gtctccccag ctgctgatct accggatgag caacctgaac         180
agcggcgtgc ccgatagatt ttctggctct ggcagcggca ccgacttcac cctgagaatc         240
tccggcgtgg aacccgagga cgtgggcgtg tactactgta tgcagcacct ggaatacccc         300
ctgaccttcg gagccggcac caagctggag atcaaaggcg gaggcggtag tggcggtggt         360
ggttcaggcg gtggcggatc tcaggtgcag ctggtgcagt ctggccccga gctaatcaag         420
cctggcggca gcgtgaagat gagctgcaag gcctccggct acaccttcac cagctacgtg         480
atgcactggg tgcgccagaa gcctggacag ggcctggaat ggatcggcta catcaacccc         540
tacaacgatg gcaccaagta caacgagaag ttcaagggca gagccaccct gaccagcgac         600
aagagcagca gcaccgccta catggaactg agcagcctgc ggagcgagga cagcgccgtg         660
tactattgtg ccagaggcac ctactactac ggcagccggg tgttcgacta ctggggacag         720
ggcaccacgg tcaccgtctc ctcaggtggc ggaggatctc aggctgtggt gactcaggag         780
ccctcactga ctgtgtcccc aggagggaca gtcactctca cctgtcgctc aagtactggg         840
gctgttacaa ctagtaacta tgccaactgg gtccagcaga acctggaca agcacccagg          900 ggtctgattg gtggtaccaa caagcgagct ccaggtaccc ctgcccggtt ctcaggctcc         960
ctccttgggg gcaaagctgc cctgacactg tcaggtgtgc agcctgagga cgaggctgag        1020
tattactgcg ctctatggta cagcaacctc tgggtgttcg gcggagggac caagctgacc        1080
gtcctaggcc aaccgaaagc ggcgccctcg gtcactctgt tcccgccctc ctctgaggag        1140
cttcaagcca caaggccac actggtgtgt ctcataagtg acttctaccc gggagccgtg         1200
acagtggcct ggaaggcaga tagcagcccc gtcaaggcgg gagtggagac caccacaccc        1260
tccaaacaaa gcaacaacaa gtacgcggcc agcagctatc tgagcctgac gcctgagcag        1320
tggaagtccc acagaagcta cagctgccag gtcacgcatg aagggagcac cgtggagaag        1380
acagtggccc ctacagaatg tccaccgtgc tcatag                                  1416

<210> SEQ ID NO 57
<211> LENGTH: 232
<212> TYPE: PRT
<213> ORGANISM: Artificial Sequence
<220> FEATURE:
<223> OTHER INFORMATION: Synthetic Construct
```

```
<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Pro Pro Cys Ser
225                 230

<210> SEQ ID NO 58
<211> LENGTH: 218
<212> TYPE: PRT
<213> ORGANISM: Artificial Sequence
<220> FEATURE:
<223> OTHER INFORMATION: Synthetic Construct

<400> SEQUENCE: 58

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
```

-continued

```
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Cys Pro Pro Cys Ser
    210                 215
```

```
<210> SEQ ID NO 59
<211> LENGTH: 248
<212> TYPE: PRT
<213> ORGANISM: Artificial Sequence
<220> FEATURE:
<223> OTHER INFORMATION: Synthetic Construct

<400> SEQUENCE: 59

Asp Val Val Met Thr Gln Ser Pro Ser Ser Ile Pro Val Thr Leu Gly
1               5                   10                  15

Glu Ser Val Ser Ile Ser Cys Arg Ser Ser Lys Ser Leu Gln Asn Val
                20                  25                  30

Asn Gly Asn Thr Tyr Leu Tyr Trp Phe Gln Gln Arg Pro Gly Gln Ser
                35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Pro Glu Asp Val Gly Val Tyr Tyr Cys Met Gln His
                85                  90                  95

Leu Glu Tyr Pro Ile Thr Phe Gly Ala Gly Thr Lys Leu Glu Ile Lys
                100                 105                 110

Gly Gly Gly Gly Ser Gly Gly Gly Gly Ser Gly Gly Gly Gly Ser Gln
                115                 120                 125

Val Gln Leu Val Gln Ser Gly Pro Glu Leu Ile Lys Pro Gly Gly Ser
    130                 135                 140

Val Lys Met Ser Cys Lys Ala Ser Gly Tyr Thr Phe Thr Ser Tyr Val
145                 150                 155                 160

Met His Trp Val Arg Gln Lys Pro Gly Gln Gly Leu Glu Trp Ile Gly
                165                 170                 175

Tyr Ile Asn Pro Tyr Asn Asp Gly Thr Lys Tyr Asn Glu Lys Phe Lys
                180                 185                 190

Gly Arg Ala Thr Leu Thr Ser Asp Lys Ser Ser Ser Thr Ala Tyr Met
                195                 200                 205

Glu Leu Ser Ser Leu Arg Ser Glu Asp Ser Ala Val Tyr Tyr Cys Ala
    210                 215                 220

Arg Gly Thr Tyr Tyr Tyr Gly Ser Arg Val Phe Asp Tyr Trp Gly Gln
225                 230                 235                 240

Gly Thr Thr Val Thr Val Ser Ser
                245
```

```
<210> SEQ ID NO 60
<211> LENGTH: 485
<212> TYPE: PRT
<213> ORGANISM: Artificial Sequence
<220> FEATURE:
<223> OTHER INFORMATION: Synthetic Construct

<400> SEQUENCE: 60

Asp Val Val Met Thr Gln Ser Pro Ser Ser Ile Pro Val Thr Leu Gly
1               5                   10                  15

Glu Ser Val Ser Ile Ser Cys Arg Ser Ser Lys Ser Leu Gln Asn Val
            20                  25                  30

Asn Gly Asn Thr Tyr Leu Tyr Trp Phe Gln Gln Arg Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Pro Glu Asp Val Gly Val Tyr Tyr Cys Met Gln His
                85                  90                  95

Leu Glu Tyr Pro Ile Thr Phe Gly Ala Gly Thr Lys Leu Glu Ile Lys
            100                 105                 110

Gly Gly Gly Gly Ser Gly Gly Gly Gly Ser Gly Gly Gly Gly Ser Gln
            115                 120                 125

Val Gln Leu Val Gln Ser Gly Pro Glu Leu Ile Lys Pro Gly Gly Ser
    130                 135                 140

Val Lys Met Ser Cys Lys Ala Ser Gly Tyr Thr Phe Thr Ser Tyr Val
145                 150                 155                 160

Met His Trp Val Arg Gln Lys Pro Gly Gln Gly Leu Glu Trp Ile Gly
            165                 170                 175

Tyr Ile Asn Pro Tyr Asn Asp Gly Thr Lys Tyr Asn Glu Lys Phe Lys
            180                 185                 190

Gly Arg Ala Thr Leu Thr Ser Asp Lys Ser Ser Ser Thr Ala Tyr Met
            195                 200                 205

Glu Leu Ser Ser Leu Arg Ser Glu Asp Ser Ala Val Tyr Tyr Cys Ala
    210                 215                 220

Arg Gly Thr Tyr Tyr Tyr Gly Ser Arg Val Phe Asp Tyr Trp Gly Gln
225                 230                 235                 240

Gly Thr Thr Val Thr Val Ser Ser Gly Gly Gly Ser Glu Val Gln
            245                 250                 255

Leu Val Glu Ser Gly Gly Gly Leu Val Gln Pro Gly Gly Ser Leu Arg
            260                 265                 270

Leu Ser Cys Ala Ala Ser Gly Phe Thr Phe Asn Thr Tyr Ala Met Asn
            275                 280                 285

Trp Val Arg Gln Ala Pro Gly Lys Gly Leu Glu Trp Val Ala Arg Ile
    290                 295                 300

Arg Ser Lys Tyr Asn Asn Tyr Ala Thr Tyr Tyr Ala Asp Ser Val Lys
305                 310                 315                 320

Asp Arg Phe Thr Ile Ser Arg Asp Asp Ser Lys Asn Thr Leu Tyr Leu
            325                 330                 335

Gln Met Asn Ser Leu Arg Ala Glu Asp Thr Ala Val Tyr Tyr Cys Val
            340                 345                 350

Arg His Gly Asn Phe Gly Asn Ser Tyr Val Ser Trp Phe Ala Tyr Trp
            355                 360                 365

Gly Gln Gly Thr Met Val Thr Val Ser Ser Ala Ser Thr Lys Gly Pro
```

-continued

```
        370               375               380

Ser Val Phe Pro Leu Ala Pro Ser Ser Lys Ser Thr Ser Gly Gly Thr
385               390               395               400

Ala Ala Leu Gly Cys Leu Val Lys Asp Tyr Phe Pro Glu Pro Val Thr
              405               410               415

Val Ser Trp Asn Ser Gly Ala Leu Thr Ser Gly Val His Thr Phe Pro
              420               425               430

Ala Val Leu Gln Ser Ser Gly Leu Tyr Ser Leu Ser Ser Val Val Thr
              435               440               445

Val Pro Ser Ser Ser Leu Gly Thr Gln Thr Tyr Ile Cys Asn Val Asn
      450               455               460

His Lys Pro Ser Asn Thr Lys Val Asp Lys Lys Val Glu Pro Lys Ser
465               470               475               480

Cys Pro Pro Cys Ser
              485

<210> SEQ ID NO 61
<211> LENGTH: 471
<212> TYPE: PRT
<213> ORGANISM: Artificial Sequence
<220> FEATURE:
<223> OTHER INFORMATION: Synthetic Construct

<400> SEQUENCE: 61

Asp Val Val Met Thr Gln Ser Pro Ser Ser Ile Pro Val Thr Leu Gly
1               5               10               15

Glu Ser Val Ser Ile Ser Cys Arg Ser Ser Lys Ser Leu Gln Asn Val
              20               25               30

Asn Gly Asn Thr Tyr Leu Tyr Trp Phe Gln Gln Arg Pro Gly Gln Ser
        35               40               45

Pro Gln Leu Leu Ile Tyr Arg Met Ser Asn Leu Asn Ser Gly Val Pro
      50               55               60

Asp Arg Phe Ser Gly Ser Gly Ser Gly Thr Asp Phe Thr Leu Arg Ile
65               70               75               80

Ser Gly Val Glu Pro Glu Asp Val Gly Val Tyr Tyr Cys Met Gln His
              85               90               95

Leu Glu Tyr Pro Ile Thr Phe Gly Ala Gly Thr Lys Leu Glu Ile Lys
              100               105               110

Gly Gly Gly Gly Ser Gly Gly Gly Gly Ser Gly Gly Gly Gly Ser Gln
              115               120               125

Val Gln Leu Val Gln Ser Gly Pro Glu Leu Ile Lys Pro Gly Gly Ser
      130               135               140

Val Lys Met Ser Cys Lys Ala Ser Gly Tyr Thr Phe Thr Ser Tyr Val
145               150               155               160

Met His Trp Val Arg Gln Lys Pro Gly Gln Gly Leu Glu Trp Ile Gly
              165               170               175

Tyr Ile Asn Pro Tyr Asn Asp Gly Thr Lys Tyr Asn Glu Lys Phe Lys
              180               185               190

Gly Arg Ala Thr Leu Thr Ser Asp Lys Ser Ser Ser Thr Ala Tyr Met
              195               200               205

Glu Leu Ser Ser Leu Arg Ser Glu Asp Ser Ala Val Tyr Tyr Cys Ala
      210               215               220

Arg Gly Thr Tyr Tyr Tyr Gly Ser Arg Val Phe Asp Tyr Trp Gly Gln
225               230               235               240

Gly Thr Thr Val Thr Val Ser Ser Gly Gly Gly Gly Ser Gln Ala Val
```

-continued

```
                    245              250              255

Val Thr Gln Glu Pro Ser Leu Thr Val Ser Pro Gly Gly Thr Val Thr
            260              265              270

Leu Thr Cys Arg Ser Ser Thr Gly Ala Val Thr Thr Ser Asn Tyr Ala
        275              280              285

Asn Trp Val Gln Gln Lys Pro Gly Gln Ala Pro Arg Gly Leu Ile Gly
    290              295              300

Gly Thr Asn Lys Arg Ala Pro Gly Thr Pro Ala Arg Phe Ser Gly Ser
305              310              315              320

Leu Leu Gly Gly Lys Ala Ala Leu Thr Leu Ser Gly Val Gln Pro Glu
            325              330              335

Asp Glu Ala Glu Tyr Tyr Cys Ala Leu Trp Tyr Ser Asn Leu Trp Val
            340              345              350

Phe Gly Gly Gly Thr Lys Leu Thr Val Leu Gly Gln Pro Lys Ala Ala
        355              360              365

Pro Ser Val Thr Leu Phe Pro Pro Ser Ser Glu Glu Leu Gln Ala Asn
    370              375              380

Lys Ala Thr Leu Val Cys Leu Ile Ser Asp Phe Tyr Pro Gly Ala Val
385              390              395              400

Thr Val Ala Trp Lys Ala Asp Ser Ser Pro Val Lys Ala Gly Val Glu
            405              410              415

Thr Thr Thr Pro Ser Lys Gln Ser Asn Asn Lys Tyr Ala Ala Ser Ser
            420              425              430

Tyr Leu Ser Leu Thr Pro Glu Gln Trp Lys Ser His Arg Ser Tyr Ser
        435              440              445

Cys Gln Val Thr His Glu Gly Ser Thr Val Glu Lys Thr Val Ala Pro
    450              455              460

Thr Glu Cys Pro Pro Cys Ser
465              470
```

MULTISPECIFIC ANTIGEN BINDING PROTEINS CAPABLE OF BINDING CD19 AND CD3, AND USE THEREOF

CROSS REFERENCE TO RELATED APPLICATIONS

This application is a national stage application under 35 U.S.C. § 371 of International Application No. PCT/CN2019/127433, filed internationally on Dec. 23, 2019, which claims priority benefit of International Application No. PCT/CN2018/123108, filed on Dec. 24, 2018, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 221992000400SEQLIST.TXT, date recorded: May 13, 2021, size: 54 KB).

FIELD OF THE INVENTION

The present invention relates to multispecific antigen binding proteins (MSAPs) that specifically bind to CD3 and CD19. Further provided herein are pharmaceutical compositions comprising the MSAPs, methods of treating cancer using the MSAPs, and kits comprising the MSAPs.

BACKGROUND OF THE INVENTION

Some antigens are over-expressed, mutagenized, or selectively mutagenized in tumor tissues. Therefore, antibodies targeting specific antigens on the surface of cancer cells can be used as cancer therapeutics. The B-lymphocyte antigen CD19 is also known as CD19 molecule (cluster of differentiation 19), B-lymphocyte surface antigen B4, T-cell surface antigen Leu-12 and CVID3. CD19 is expressed in both normal and malignant B lymphocytes and is considered a B-cell tumor-associated antigen. It can be used as biomarker for B lymphocyte development, lymphoma diagnosis, and a target for leukemia immunotherapies.

CD3, comprising three different polypeptide chains ($\varepsilon$, $\delta$ and $\gamma$ chains), is an antigen expressed by T cells. The three CD3 polypeptide chains associate with the T-cell receptor (TCR) and the $\zeta$-chain to form the TCR complex, which has the function of activating signaling cascades in T cells. Currently, many therapeutic strategies target the TCR signal transduction to treat diseases using anti-human CD3 monoclonal antibodies. The CD3 specific antibody OKT3 is the first monoclonal antibody approved for human therapeutic use, and is clinically used as an immunomodulator for the treatment of allogenic transplant rejections.

Although bispecific antibodies have been shown to have potential in effectively killing cancer cells, severe adverse effects, including systemic immune activation, immunogenicity (anti-drug antibody effect), and the generally poor manufacturability of these molecules, have greatly limited the widespread application of this type of drugs. For example, one drawback of CD19×CD3 bispecific scFv-scFv (single-chain variable fragment) fusion protein (Blinatumomab) is that this drug needs to be administered intravenously (i.v.) on a daily basis due to its short half-life and incompatibility with subcutaneous administration; yet, neurological effects such as disorientation, confusion, speech and language impairment, tremor or convulsion still occurred during clinical trials (Bargou et al. Science 321 (5891): 974-797, 2008).

The drawbacks of current formats of bispecific antibodies remain great challenges for their widespread application in the treatment of cancer patients with good efficacy and safety. Therefore, there is an urgent need in the field for the development of new bispecific antibodies or treatment regimen with improved efficacy, stability, safety and manufacturability.

BRIEF SUMMARY OF THE INVENTION

The present invention provides multispecific antigen binding proteins ("MSAPs", such as bispecific antigen binding proteins, "BSAPs") that specifically bind to CD3 and CD19, pharmaceutical compositions comprising the MSAPs, and methods of treating cancer using the MSAPs.

In one aspect of the present invention, there is provided a MSAP (such as BSAP) comprising: I. an anti-CD3 Fab fragment that specifically binds to CD3, wherein the anti-CD3 Fab fragment comprises: (a) an immunoglobulin (Ig) heavy chain variable region (VH) and an Ig heavy chain constant region (CH1); and (b) an Ig light chain variable region (VL) and an Ig light chain constant region (CL); optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment. In some embodiments, the anti-CD19 antigen binding fragment (e.g., scFv) is fused to the N-terminus of the VH of the anti-CD3 Fab fragment. In some embodiments, the anti-CD19 antigen binding fragment (e.g., scFv) is fused to the N-terminus of the VL of the anti-CD3 Fab fragment. In some embodiments, the MSAP (such as BSAP) comprises a first anti-CD19 antigen binding fragment (e.g., scFv) and a second anti-CD19 antigen binding fragment (e.g., scFv), wherein the first anti-CD19 antigen binding fragment is fused to the N-terminus of the VH of the anti-CD3 Fab fragment, and wherein the second anti-CD19 antigen binding fragment is fused to the N-terminus of the VL of the anti-CD3 Fab fragment.

In some embodiments according to any of the MSAPs (such as BSAPs) described above, the anti-CD3 Fab fragment specifically binds to the N-terminus of CD38, such as an epitope within amino acids 1-27 of CD3E. In some embodiments, the VH of the anti-CD3 Fab fragment comprises a heavy chain hypervariable region H1 (HVR-H1) comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or the VL of the anti-CD3 Fab fragment comprises a light chain hypervariable region L1 (HVR-L1) comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by a disulfide bond. In some embodiments, the CH1 and the CL of the anti-CD3 Fab fragment are connected by about 1 to about 5 disulfide bonds, such as about 2 disulfide bonds. In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond.

In some embodiments according to any of the MSAPs (such as BSAPs) described above, the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH, wherein the VH of the anti-CD19 antigen binding fragment comprises an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or the anti-CD19 antigen binding fragment (e.g., scFv) comprises a VL, wherein the VL of the anti-CD19 antigen binding fragment comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:49. In some embodiments, the anti-CD19 antigen binding fragment (e.g., scFv) comprises a VH comprising the amino acid sequence of SEQ ID NO: 7, and/or a VL comprising the amino acid sequence of SEQ ID NO:8 or 50. In some embodiments, the VH of the anti-CD19 antigen binding fragment (e.g., scFv) comprises the amino acid sequence of SEQ ID NO:7; and/or the VL of the anti-CD19 antigen binding fragment (e.g., scFv) comprises the amino acid sequence of SEQ ID NO:50.

In some embodiments according to any of the MSAPs (such as BSAPs) described above, the anti-CD19 antigen binding fragment is a single chain variable fragment (scFv). In some embodiments, the anti-CD19 scFv comprises the amino acid sequence of SEQ ID NO:51 or 59. In some embodiments, the anti-CD19 scFv comprises the amino acid sequence of SEQ ID NO: 51. In some embodiments, the MSAP (such as BSAP) comprises a first anti-CD19 scFv and a second anti-CD19 scFv. In some embodiments, the first and the second anti-CD19 scFvs have the same amino acid sequence. In some embodiments, the first and the second anti-CD19 scFvs have different amino acid sequences.

In some embodiments according to any of the MSAPs (such as BSAPs) described above, the linker comprises about 2 to about 30 amino acid residues (such as about 2 to about 15 amino acid residues) selected from the group consisting of glycine, serine, arginine, and alanine. In some embodiments, the linker is selected from the group consisting of SEQ ID NOs: 20-22, 29, and 31-44, such as SEQ ID NO:44.

In some embodiments according to any of the MSAPs (such as BSAPs) described above, the MSAP comprises a first polypeptide and a second polypeptide, wherein the first polypeptide comprises the amino acid sequence of SEQ ID NO:53 or 60, and wherein the second polypeptide comprises the amino acid sequence of SEQ ID NO:54 or 61. In some embodiments, the MSAP (e.g., BSAP) comprises a first polypeptide and a second polypeptide, wherein the first polypeptide comprises the amino acid sequence of SEQ ID NO:53, and wherein the second polypeptide comprises the amino acid sequence of SEQ ID NO:54. In some embodiments, the MSAP (e.g., BSAP) comprises a first polypeptide and a second polypeptide, wherein the first polypeptide comprises the amino acid sequence of SEQ ID NO:60, and wherein the second polypeptide comprises the amino acid sequence of SEQ ID NO:61.

In some embodiments according to any of the MSAPs (such as BSAPs) described above, the MSAP comprises a first polypeptide and a second polypeptide, wherein the first polypeptide comprises the amino acid sequence of SEQ ID NO:53 or 60, and wherein the second polypeptide comprises the amino acid sequence of SEQ ID NO:58. In some embodiments, the MSAP (e.g., BSAP) comprises a first polypeptide and a second polypeptide, wherein the first polypeptide comprises the amino acid sequence of SEQ ID NO:53, and wherein the second polypeptide comprises the amino acid sequence of SEQ ID NO:58. In some embodiments, the MSAP (e.g., BSAP) comprises a first polypeptide and a second polypeptide, wherein the first polypeptide comprises the amino acid sequence of SEQ ID NO:60, and wherein the second polypeptide comprises the amino acid sequence of SEQ ID NO:58.

In some embodiments according to any of the MSAPs (such as BSAPs) described above, the MSAP (such as BSAP) comprises a first polypeptide and a second polypeptide, wherein the first polypeptide comprises the amino acid sequence of SEQ ID NO:57, and wherein the second polypeptide comprises the amino acid sequence of SEQ ID NO:54 or 61. In some embodiments, the MSAP (e.g., BSAP) comprises a first polypeptide and a second polypeptide, wherein the first polypeptide comprises the amino acid sequence of SEQ ID NO:57, and wherein the second polypeptide comprises the amino acid sequence of SEQ ID NO:54. In some embodiments, the MSAP (e.g., BSAP) comprises a first polypeptide and a second polypeptide, wherein the first polypeptide comprises the amino acid sequence of SEQ ID NO:57, and wherein the second polypeptide comprises the amino acid sequence of SEQ ID NO:61.

Further provided are isolated nucleic acid molecules that encode the any of the MSAPs (such as BSAPs) described above, expression vectors carrying the isolated nucleic acid molecules, isolated host cells comprising the expression vectors, and methods of producing any of the MSAPs described above, comprising culturing the isolated host cells and recovering the MSAPs from the cell culture.

Also provided herein are uses, compositions (such as pharmaceutical compositions), kits and articles of manufactures comprising any of the MSAPs (such as BSAPs) described above. In some embodiments, there is provided a composition (such as pharmaceutical composition) comprising any of the MSAPs (such as BSAPs) described above, and optionally a pharmaceutically acceptable carrier.

Use of any of the MSAPs (such as BSAPs) described above in the preparation of a medicament for treating a cancer is further provided herein. In some embodiments, there is provided a method of treating a cancer (e.g., DLBCL or ALL) in an individual in need thereof, comprising administering to the individual an effective amount of any of the MSAPs (such as BSAPs) described above or a composition (such as pharmaceutical composition) thereof. In some embodiments, the MSAP (such as BSAP) or the composition (such as pharmaceutical composition) is administered intravenously. In some embodiments, the individual is a human. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the cancer is DLBCL. In some embodiments, the cancer is ALL.

These and other aspects and advantages of the present invention will become apparent from the subsequent detailed description and the appended claims. It is to be understood that one, some, or all of the properties of the various embodiments described herein may be combined to form other embodiments of the present invention.

The disclosures of all publications, patents, patent applications and published patent applications referred to herein are hereby incorporated herein by reference in their entirety.

DETAILED DESCRIPTION OF THE INVENTION

Figure 1A:
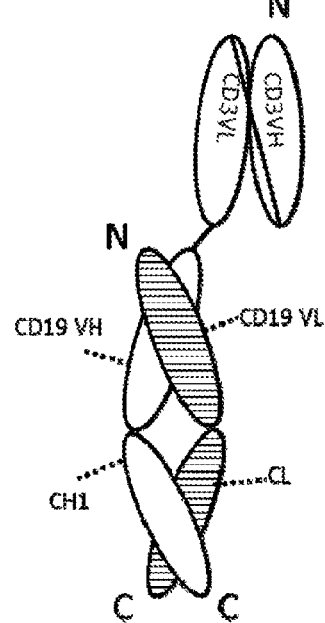
FIG. 1A depicts the structure of an exemplary CD19×CD3 MSAP ITAB2009.

The present invention provides a multispecific antigen binding protein (MSAP) comprising an anti-CD3 Fab fragment that specifically binds to CD3 and an anti-CD19 antigen binding fragment (e.g., scFv) that specifically binds to CD19 (hereinafter referred to as "CD3×CD19 MSAP"). In some embodiments, the CD3×CD19 MSAP (such as BSAP) comprises a first anti-CD19 scFv and a second anti-CD19 scFv, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment. In some embodiments, the two anti-CD19 scFvs are the same. The present invention also provides methods of treating cancer using the CD3×CD19 MSAPs (such as BSAP) described herein, particularly for hematological malignancies.

Current anti-cancer bispecific antibodies suffer from several drawbacks, such as poor manufacturability, aggregation, short half-life, severe adverse effects (such as systemic immune activation, immunogenicity (anti-drug antibody response)), long infusion time, and inability of retaining in tumor tissue, which present great challenges for widespread application of these anti-cancer bispecific antibodies in cancer treatment with good efficacy and safety. For example, Blinatumomab (BLINCYTO®, anti-CD3/anti-CD19 bispecific scFv-scFv) was approved in the United States in 2014 as second-line treatment for Philadelphia chromosome-negative relapsed or refractory acute lymphoblastic leukemia (ALL). However, due to its short half-life and incompatibility with subcutaneous administration, Blinatumomab needs to be administered intravenously (i.v.) on a daily basis; yet, neurological effects such as disorientation, confusion, speech and language impairment, tremor or convulsion still occurred during clinical trials (Bargou et al. Science 321 (5891): 974-797, 2008).

After extensive investigation, inventors of the present application unexpectedly discovered a CD3×CD19 MSAP (such as BSAP) format, which is fusing an anti-CD19 antigen binding fragment (e.g., scFv) at the N-terminus of an anti-CD3 Fab fragment. The CD3×CD19 MSAPs (such as BSAPs) described herein were found to have several advantages compared to other multispecific proteins known in the art. First, the CD3×CD19 MSAPs (such as BSAPs) described herein have enhanced cytotoxic activities against cancer cells, especially for low CD19-expressing tumor, such as B-cell lymphoma and acute lymphocytic leukemia (ALL). Second, the CD3×CD19 MSAPs (such as BSAPs) described herein cross-react with non-human primates, such as cynomolgus monkeys, which may facilitate toxicological research on non-human primates (e.g., cynomolgus monkeys) for the benefit of human clinical study prediction. Third, the CD3×CD19 MSAPs (such as BSAPs) described herein have extended half-life may enable lower dosing frequency and shorter infusion time, providing more convenience to the patients.

Accordingly, in one aspect, the present invention provides a MSAP (such as BSAP) comprising: I. an anti-CD3 Fab fragment that specifically binds to CD3, wherein the anti-CD3 Fab fragment comprises: (a) an immunoglobulin (Ig) heavy chain variable region (VH) and an Ig heavy chain constant region (CH1); and (b) an Ig light chain variable region (VL) and an Ig light chain constant region (CL); II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv). In another aspect, the present invention provides a MSAP (such as BSAP) comprising: I. an anti-CD3 Fab fragment that specifically binds to CD3, wherein the anti-CD3 Fab fragment comprises: (a) an immunoglobulin (Ig) heavy chain variable region (VH) and an Ig heavy chain constant region (CH1); and (b) an Ig light chain variable region (VL) and an Ig light chain constant region (CL); wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv).

Also provided are pharmaceutical compositions and kits comprising the CD3×CD19 MSAPs (such as BSAPs) described herein, and methods of use thereof for treating cancers.

I. Definitions

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al., Short Protocols in Molecular Biology, 3rd ed., John Wiley & Sons, 1995; Sambrook and Russell, Molecular Cloning: A Laboratory Manual (3rd Edition, 2001); Maniatis et al., Molecular Cloning: A Laboratory Manual (1982); DNA Cloning: A Practical Approach, vol. I&II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals.

As used herein, an "effective amount" refers to an amount of an agent or drug effective to treat a disease or disorder in a subject. In the case of cancer, the effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, an "individual" or a "subject" refers to a mammal, including, but not limited to, human, bovine, horse, feline, canine, rodent, or primate. In some embodiments, the individual is a human.

The term "antibody" is used in the broadest sense and specifically covers monoclonal antibodies (including full length monoclonal antibodies), multispecific antibodies (e.g., bispecific antibodies), and antibody fragments so long as they exhibit the desired biological activity or function. As used herein, the terms "immunoglobulin" (Ig) and "antibody" are used interchangeably.

The terms "native antibody", "full length antibody," "intact antibody" and "whole antibody" are used herein interchangeably to refer to an antibody in its substantially intact form, not antibody fragments as defined below. The terms particularly refer to an antibody with heavy chains that contain an Fc region. Native antibodies are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs, also referred to as CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. Cellular and Mol. Immunology, 4th ed. (W.B. Saunders, Co., 2000). An antibody may be part of a larger fusion molecule, formed by covalent or non-covalent association of the antibody with one or more other proteins or peptides.

"Antibody fragments" comprise a portion of an intact antibody, preferably comprising the antigen binding region thereof. In some embodiments, the antibody fragment described herein is an antigen binding fragment. Examples of antibody fragments or antigen binding fragments include Fab, Fab', F(ab')$_2$, and Fv fragments (such as single-chain variable fragment, scFv); diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment has two polypeptide chains, containing the heavy- and light-chain variable domains (VH, VL), and also containing the constant domain of the light chain (CL) and the first constant domain (CH1) of the heavy chain. We herein refer to "Fd" as the heavy chain polypeptide portion of a Fab fragment, which comprises the VH and CH1 domains. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, The Pharmacology of Monoclonal Antibodies. Springer Berlin Heidelberg, 1994. 269-315.

The "Fc" fragment comprises the carboxy-terminal portions of both heavy chains held together by di-sulfides. The effector functions of antibodies are determined by sequences in the Fc region, which region is also the part recognized by Fc receptors (FcR) found on certain types of cells.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In some embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature 256:495-97 (1975); Hongo et al., Hybridoma 14 (3): 253-260 (1995), Harlow et al., Antibodies: A Laboratory Manual, (Cold Spring Harbor Laboratory Press, 2nd ed. 1988); Hammer-ling et al., Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature 352:624-628 (1991); Marks et al., J. Mol. Biol. 222:581-597 (1992); Sidhu et al., J. Mol. Biol. 338 (2): 299-310 (2004); Lee et al., J. Mol. Biol. 340 (5): 1073-1093 (2004); Fellouse, Proc. Natl. Acad. Sci. USA 101 (34): 12467-12472 (2004); and Lee et al., J. Immunol. Methods 284 (1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90:2551 (1993); Jakobovits et al., Nature 362:255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661,016; Marks et al., Bio/Technology 10:779-783 (1992); Lonberg et al., Nature 368:856-859 (1994); Morrison, Nature 368:812-813 (1994); Fishwild et al., Nature Biotechnol. 14:845-851 (1996); Neuberger, Nature Biotechnol. 14:826 (1996); and Lonberg and Huszar, Intern. Rev. Immunol. 13:65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol. 227:381 (1991); Marks et al., J. Mol. Biol. 222:581 (1991). Also available for the preparation of human monoclonal antibodies are methods described in Cole et al., Monoclonal Antibodies and Cancer Therapy, Alan R. Liss, 77 (1985); Boerner et al., J. Immunol. 147 (1): 86-95 (1991). See also van Dijk and van de Winkel, Curr. Opin. Pharmacol. 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). HVR is also referred to as "CDR" or "complementarity determining region".

The structures and locations of immunoglobulin variable regions may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

"Framework" or "FR" residues are those variable domain residues other than the HVR residues as herein defined.

The term "covalently linked" as used herein, refers to a direct linkage through one or more chemical bonds or an indirect linkage through one or more linkers. Any suitable chemical bond can be used to create a direct linkage, including but not limited to, a covalent bond such as a peptide bond and a disulfide bond, or a non-covalent bond such as a hydrogen bond, a hydrophobic bond, an ionic bond, or a van der Waals bond.

"Covalent bond" as used herein refers to a stable bond between two atoms sharing one or more electrons. Examples of covalent bonds include, but are not limited to, peptide bonds and disulfide bonds. As used herein, "peptide bond" refers to a covalent bond formed between a carboxyl group of an amino acid and an amine group of an adjacent amino acid. A "disulfide bond" as used herein refers to a covalent bond formed between two sulfur atoms, such as a combination of a heavy chain fragment CH1 and a light chain fragment CL by one or more disulfide bonds. One or more disulfide bonds may be formed between the two fragments by linking the thiol groups in the two fragments. In some embodiments, one or more disulfide bonds can be formed between one or more cysteines of the heavy chain fragment and the light chain fragment, respectively. Disulfide bonds can be formed by oxidation of two thiol groups. In some embodiments, the covalent linkage is directly linked by a covalent bond. In some embodiments, the covalent linkage is directly linked by a peptide bond or a disulfide bond.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In some embodiments, an antibody that specifically binds to a target has a dissociation constant ($K_d$) of $\leq 1$ µM, $\leq 100$ nM, $\leq 10$ nM, $\leq 1$ nM, or $\leq 0.1$ nM. In some embodiments, an antibody specifically binds to an epitope on a protein that is conserved among the protein from different species. In another embodiment, specific binding can include, but does not require exclusive binding.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGA-LIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table A. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |

TABLE A-continued

| Original Residue | Exemplary Substitutions |
| --- | --- |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

As used herein, a "multispecific antigen binding protein" (MSAP) refers to a protein having a Fab fragment covalently linked to one or more antigen binding fragments that have different characteristics compared to the Fab fragment. The characteristics may be biological characteristics, such as in vitro or in vivo activity. The characteristics may also be simple chemical or physical properties, such as binding to a target molecule, catalytic reactions, and the like. The Fab fragment and the one or more antigen binding fragments may be directly connected by a single peptide bond, or connected via a peptide linker, but to each other in an in-frame manner. The terms "multispecific antigen binding protein" and "MSAP" are used herein interchangeably to refer to an antigen binding protein that has polyepitopic specificity.

The term "multispecific" as used in conjunction with an antibody or antigen binding protein (such as a multispecific antigen binding protein, MSAP) refers to an antibody or antigen binding protein having polyepitopic specificity (i.e., is capable of specifically binding to two, three, or more, different epitopes on one biological molecule or is capable of specifically binding to epitopes on two, three, or more, different biological molecules). Unless otherwise indicated, the order in which the antigens bound by a multispecific antibody or MSAP are listed in a multispecific antibody or MSAP name is arbitrary. That is, the terms "anti-CD3/CD19," "anti-CD19/CD3," "CD19×CD3" and "CD3×CD19" may be used interchangeably to refer to multispecific antibodies (such as MSAP) that specifically bind to both CD3 and CD19 (e.g., different CD19 epitopes). In some embodiments, an MSAP is a BSAP.

The term "bispecific" as used in conjunction with an antibody or antigen binding protein (such as a bispecific antigen binding protein, BSAP) refers to an antibody or antigen binding protein capable of specifically binding to two different epitopes on one biological molecule, or capable of specifically binding to epitopes on two different biological molecules. Unless otherwise indicated, the order in which the antigens bound by a bispecific antibody or BSAP are listed in a bispecific antibody or BSAP name is arbitrary. That is, the terms "anti-CD3/CD19," "anti-CD19/CD3," "CD19×CD3" and "CD3×CD19" may be used interchangeably to refer to bispecific antibodies (such as BSAP) that specifically bind to both CD3 and CD19. In some embodiments, the BSAP is bivalent. In some embodiments, the BSAP is multivalent (e.g., trivalent).

As used herein, the "C terminus" of a polypeptide refers to the last amino acid residue of the polypeptide which donates its amine group to form a peptide bond with the carboxyl group of its adjacent amino acid residue. "N terminus" of a polypeptide as used herein refers to the first amino acid of the polypeptide which donates its carboxyl group to form a peptide bond with the amine group of its adjacent amino acid residue.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "cell" includes the primary subject cell and its progeny.

The term "cytokine storm," also known as a "cytokine cascade" or "hypercytokinemia," is a potentially fatal immune reaction typically consisting of a positive feedback loop between cytokines and immune cells, with highly elevated levels of various cytokines (e.g. INF-γ, IL-10, IL-6, CCL2, etc.).

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. CD3×CD19 Multispecific Antigen Binding Proteins (CD3×CD19 MSAPs)

Figure 1B:
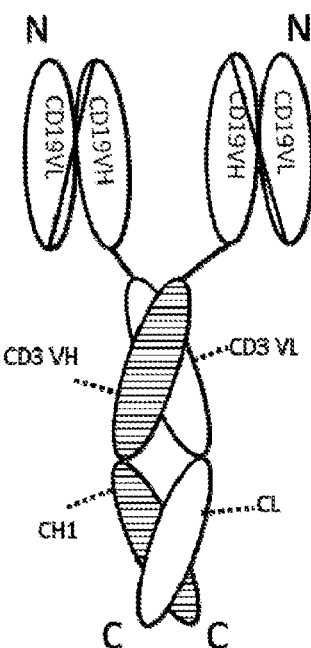
FIG. 1B depicts the structure of an exemplary CD19×CD3 MSAP ITAB2007.

The present invention provides a multispecific antigen binding protein (MSAP) comprising an anti-CD3 Fab fragment that specifically binds to CD3 (hereinafter referred to as "anti-CD3 Fab fragment") and an anti-CD19 antigen binding fragment (e.g., scFv) that specifically binds to CD19 (hereinafter referred to as "anti-CD19 antigen binding fragment", e.g., anti-CD19 scFv) fused together via an optional linker, hereinafter referred to as "CD3×CD19 MSAP." In some embodiments, the anti-CD3 Fab fragment comprises (a) an immunoglobulin (Ig) heavy chain variable region (VH) and an Ig heavy chain constant region (CH1); and (b) an Ig light chain variable region (VL) and an Ig light chain constant region (CL). In some embodiments, the anti-CD3 Fab fragment comprises (a) an immunoglobulin (Ig) heavy chain variable region (VH) and an Ig heavy chain constant region (CH1); and (b) an Ig light chain variable region (VL) and an Ig light chain constant region (CL); wherein the CH1 and the CL of the anti-CD3 Fab fragment are connected by a disulfide bond. In some embodiments, the anti-CD19 antigen binding fragment (e.g., scFv) is fused to the N-terminus of the VH of the anti-CD3 Fab fragment. In some embodiments, the anti-CD19 antigen binding fragment (e.g., scFv) is fused to the N-terminus of the VL of the anti-CD3 Fab fragment. In some embodiments, the CD3×CD19 MSAP (such as BSAP) comprises a first anti-CD19 antigen binding fragment (e.g., scFv) and a second anti-CD19 antigen binding fragment (e.g., scFv), wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment. In some embodiments, the CD3× CD19 MSAP is trivalent and trispecific, i.e., the two anti-CD19 antigen binding fragments (e.g., scFvs) specifically bind to different epitopes of CD19, hereinafter referred to as "CD3×CD19 trispecific antigen binding protein" or "CD3× CD19 TSAP". In some embodiments, the CD3×CD19 MSAP is trivalent and bispecific, i.e., the two anti-CD19 antigen binding fragments (e.g., scFvs) specifically bind to the same CD19 epitope, hereinafter referred to as "trivalent CD3×CD19 BSAP". In some embodiments, the CD3×CD19 MSAP is bivalent and bispecific, hereinafter referred to as "bivalent CD3×CD19 BSAP". An exemplary CD3×CD19 MSAP is shown in FIG. 1B.

The CD3×CD19 MSAP (such as BSAP) of the present invention has significant advantages including but not limited to: 1) demonstrated enhanced cancer cell killing efficacy; 2) demonstrated superior in vivo therapeutic effects on burkitt's lymphoma and precursor B-cell (preB) acute lymphoblastic leukemia (ALL) in animal models; and 3) cross-reactivity with non-human primates, such as cynomolgus monkeys, which may facilitate toxicological research on non-human primates (e.g., cynomolgus monkeys) for the benefit of human clinical study prediction.

Thus, in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv). In some embodiments, the CH1 and the CL of the anti-CD3 Fab fragment are connected by a disulfide bond. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv). In some embodiments, the anti-CD19 antigen binding fragment (e.g., scFv) is fused to the N-terminus of the VH of the anti-CD3 Fab fragment. In some embodiments, the anti-CD19 antigen binding fragment (e.g., scFv) is fused to the N-terminus of the VL of the anti-CD3 Fab fragment. In some embodiments, the MSAP (such as BSAP) comprises a first anti-CD19 antigen binding fragment (e.g., scFv) and a second anti-CD19 antigen binding fragment (e.g., scFv), wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises a heavy chain hypervariable region H1 (HVR-H1) comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises a light chain hypervariable region L1 (HVR-L1) comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO: 45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 antigen binding fragment (e.g., scFv) comprises a VH comprising the amino acid sequence of SEQ ID NO:7, and/or a VL comprising the amino acid sequence of SEQ ID NO:50. In some embodiments, the anti-CD19 antigen binding fragment is an scFv. In some embodiments, the anti-CD19 scFv comprises the amino acid sequence of SEQ ID NO: 51 or 59. In some embodiments, the anti-CD19 scFv comprises the amino acid sequence of SEQ ID NO:51. In some embodiments, the MSAP (such as BSAP) comprises two anti-CD19 scFvs having the same amino acid sequence. In some embodiments, the MSAP comprises two anti-CD19 scFvs having different amino acid sequences. In some embodiments, the linker comprises about 2 to about 30 amino acid residues selected from the group consisting of glycine, serine, arginine, and alanine. In some embodiments, the linker comprises about 2 to about 15 amino acid residues. In some embodiments, the linker is selected from the group consisting of SEQ ID NOs: 20-22, 29, and 31-44 (e.g., SEQ ID NO:44). In some embodiments, the MSAP (e.g., BSAP) comprises a first polypeptide and a second polypeptide, wherein the first polypeptide comprises the amino acid sequence of SEQ ID NO:53 or 60, and wherein the second polypeptide comprises the amino acid sequence of SEQ ID NO:54 or 61. In some embodiments, the MSAP (e.g., BSAP) comprises a first polypeptide and a second polypeptide, wherein the first polypeptide comprises the amino acid sequence of SEQ ID NO:53, and wherein the second polypeptide comprises the amino acid sequence of SEQ ID NO:54. In some embodiments, the MSAP (e.g., BSAP) comprises a first polypeptide and a second polypeptide, wherein the first polypeptide comprises the amino acid sequence of SEQ ID NO:60, and wherein the second polypeptide comprises the amino acid sequence of SEQ ID NO:61. In some embodiments, the MSAP (e.g., BSAP) comprises a first polypeptide comprising the amino acid sequence of SEQ ID NO: 53, and a second polypeptide comprising the amino acid sequence of SEQ ID NO:58. In some embodiments, the MSAP (e.g., BSAP) comprises a first polypeptide comprising the amino acid sequence of SEQ ID NO:60, and a second polypeptide comprising the amino acid sequence of SEQ ID NO:58. In some embodiments, the MSAP (e.g., BSAP) comprises a first polypeptide comprising the amino acid sequence of SEQ ID NO:57, and a second polypeptide comprising the amino acid sequence of SEQ ID NO:54. In some embodiments, the MSAP (e.g., BSAP) comprises a first polypeptide comprising the amino acid sequence of SEQ ID NO:57, and a second polypeptide comprising the amino acid sequence of SEQ ID NO:61.

In some embodiments, the anti-CD19 antigen binding fragment (e.g., scFv) is fused to the N-terminus of the VH of the anti-CD3 Fab fragment.

Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 scFv that specifically binds to CD19; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the anti-CD3 Fab fragment specifically binds to the N-terminus of CD38 (e.g., an epitope within amino acids 1-27 of CD3E). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO: 45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (e.g., BSAP) comprises a first polypeptide comprising the amino acid sequence of SEQ ID NO:53, and a second polypeptide comprising the amino acid sequence of SEQ ID NO: 58. In some embodiments, the MSAP (e.g., BSAP) comprises a first polypeptide comprising the amino acid sequence of SEQ ID NO:60, and a second polypeptide comprising the amino acid sequence of SEQ ID NO:58.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO:10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment (e.g., scFv) comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the anti-CD19 antigen binding fragment (e.g., scFv) comprises a VL, wherein the VL of the anti-CD19 antigen binding fragment (e.g., scFv) comprises an HVR-L1 comprising the amino acid sequence of SEQ ID NO: 47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO: 14; II. an anti-CD19 scFv that specifically binds to CD19, wherein the anti-CD19 scFv comprises a VH, wherein the VH of the anti-CD19 scFv comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the anti-CD19 scFv comprises a VL, wherein the VL of the anti-CD19 scFv comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO:16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. Thus in some embodiments, there is provided a MSAP (such as BSAP)

comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises the amino acid sequence of SEQ ID NO:51 or 59; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53, and a second polypeptide comprising the amino acid sequence of SEQ ID NO:58. In some embodiments, the MSAP (e.g., BSAP) comprises a first polypeptide comprising the amino acid sequence of SEQ ID NO:60, and a second polypeptide comprising the amino acid sequence of SEQ ID NO:58.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO:14; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment (e.g., scFv) comprises the amino acid sequence of SEQ ID NO:7; and/or wherein the anti-CD19 antigen binding fragment (e.g., scFv) comprises a VL, wherein the VL of the anti-CD19 antigen binding fragment (e.g., scFv) comprises the amino acid sequence of SEQ ID NO:8 or 50; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO:12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises a VH, wherein the VH of the anti-CD19 scFv comprises the amino acid sequence of SEQ ID NO:7; and/or wherein the anti-CD19 scFv comprises a VL, wherein the VL of the anti-CD19 scFv comprises the amino acid sequence of SEQ ID NO:8 or 50; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises the amino acid sequence of SEQ ID NO:15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises the amino acid sequence of SEQ ID NO:51 or 59; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO: 44). In some embodiments, the MSAP (such as BSAP) comprises a first polypeptide comprising the amino acid sequence of SEQ ID NO:53, and a second polypeptide comprising the amino acid sequence of SEQ ID NO:58. In some embodiments, the MSAP (e.g., BSAP) comprises a first polypeptide comprising the amino acid sequence of SEQ ID NO:60, and a second polypeptide comprising the amino acid sequence of SEQ ID NO:58.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment (e.g., scFv) comprises an HVR-H1 comprising the amino acid sequence of SEQ ID NO: 1, an HVR-H2 comprising the amino acid sequence of SEQ ID NO: 2, and an HVR-H3 comprising the amino acid sequence of SEQ ID NO:3; and/or wherein the anti-CD19 antigen binding fragment (e.g., scFv) comprises a VL, wherein the VL of the anti-CD19 antigen binding fragment (e.g., scFv) comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a MSAP (such as BSAP) comprising: I. an anti-CD3 Fab fragment that specifically binds to CD3, optionally wherein the anti-CD3 Fab fragment comprises: (a) an Ig VH and an Ig CH1; and (b) an Ig VL and an Ig CL; wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 scFv that specifically binds to CD19, wherein the anti-CD19 scFv comprises a VH, wherein the VH of the anti-CD19 scFv comprises an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or wherein the anti-CD19 scFv comprises a VL, wherein the VL of the anti-CD19 scFv comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the anti-CD3 Fab fragment specifically binds to the N-terminus of CD3 (e.g., an epitope within amino acids 1-27 of CD38). In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO:18; and/or the CL of the anti-CD3 Fab fragment comprises the amino acid sequence of SEQ ID NO: 52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 scFv that specifically binds to CD19, wherein the anti-CD19 scFv comprises the amino acid sequence of SEQ ID NO:51 or 59; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53, and a second polypeptide comprising the amino acid sequence of SEQ ID NO:58. In some embodiments, the MSAP (e.g., BSAP) comprises a first polypeptide comprising the amino acid sequence of SEQ ID NO:60, and a second polypeptide comprising the amino acid sequence of SEQ ID NO:58.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment comprises the amino acid sequence of SEQ ID NO:7; and/or wherein the anti-CD19 antigen binding fragment (e.g., scFv) comprises a VL, wherein the VL of the anti-CD19 antigen binding fragment comprises the amino acid sequence of SEQ ID NO: 8 or 50; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO:15; and/or wherein the VL of the anti-CD3 Fab fragment comprises the amino acid sequence of SEQ ID NO: 16; II. an anti-CD19 scFv that specifically binds to CD19, wherein the VH of the anti-CD19 scFv comprises the amino acid sequence of SEQ ID NO:7; and/or wherein the VL of the anti-CD19 scFv comprises the amino acid sequence of SEQ ID NO:8 or 50; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53, and a second polypeptide comprising the amino acid sequence of SEQ ID NO: 58. In some embodiments, the MSAP (e.g., BSAP) comprises a first polypeptide comprising the amino acid sequence of SEQ ID NO:60, and a second polypeptide comprising the amino acid sequence of SEQ ID NO:58.

In some embodiments, there is provided a MSAP (such as BSAP) comprising a first polypeptide and a second polypeptide, wherein the first polypeptide comprises the amino acid sequence of SEQ ID NO:53, and wherein the second polypeptide comprises the amino acid sequence of SEQ ID NO:58. In some embodiments, there is provided a MSAP (such as BSAP) comprising a first polypeptide and a second polypeptide, wherein the first polypeptide comprises the amino acid sequence of SEQ ID NO:60, and wherein the second polypeptide comprises the amino acid sequence of SEQ ID NO:58.

In some embodiments, the anti-CD19 antigen binding fragment (e.g., scFv) is fused to the N-terminus of the VL of the anti-CD3 Fab fragment.

Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 scFv that specifically binds to CD19; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the anti-CD3 Fab fragment specifically binds to the N-terminus of CD3 (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO: 45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:57, and a second polypeptide comprising the amino acid sequence of SEQ ID NO: 54. In some embodiments, the MSAP (e.g., BSAP) comprises a first polypeptide comprising the amino acid sequence of SEQ ID NO:57, and a second polypeptide comprising the amino acid sequence of SEQ ID NO:61.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond;

wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO: 14; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment (e.g., scFv) comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the anti-CD19 antigen binding fragment (e.g., scFv) comprises a VL, wherein the VL of the anti-CD19 antigen binding fragment (e.g., scFv) comprises an HVR-L1 comprising the amino acid sequence of SEQ ID NO: 47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a MSAP (such as BSAP) comprising: I. an anti-CD3 Fab fragment that specifically binds to CD3, optionally wherein the anti-CD3 Fab fragment comprises: (a) an Ig VH and an Ig CH1; and (b) an Ig VL and an Ig CL; wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO: 14; II. an anti-CD19 scFv that specifically binds to CD19, wherein the anti-CD19 scFv comprises a VH, wherein the VH of the anti-CD19 scFv comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the anti-CD19 scFv comprises a VL, wherein the VL of the anti-CD19 scFv comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO:12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises the amino acid sequence of SEQ ID NO:51 or 59; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:57, and a second polypeptide comprising the amino acid sequence of SEQ ID NO:54. In some embodiments, the MSAP (e.g., BSAP) comprises a first polypeptide comprising the amino acid sequence of SEQ ID NO:57, and a second polypeptide comprising the amino acid sequence of SEQ ID NO:61.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO:14; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment (e.g., scFv) comprises the amino acid sequence of SEQ ID NO:7; and/or wherein the anti-CD19 antigen binding fragment (e.g., scFv) comprises a VL, wherein the VL of the anti-CD19 antigen binding fragment (e.g., scFv) comprises the amino acid sequence of SEQ ID NO:8 or 50; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO:10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises a VH, wherein the VH of the anti-CD19 scFv comprises the amino acid sequence of SEQ ID NO:7; and/or wherein the anti-CD19 scFv comprises a VL, wherein the VL of the anti-CD19 scFv comprises the amino acid sequence of SEQ ID NO:8 or 50; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the anti-CD3 Fab fragment specifically binds to the N-terminus of CD3E (e.g., an epitope within amino acids 1-27 of CD38). In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises the amino acid sequence of SEQ ID NO:51 or 59; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO: 44). In some embodiments, the MSAP (such as BSAP) comprises a first polypeptide comprising the amino acid sequence of SEQ ID NO:57, and a second polypeptide comprising the amino acid sequence of SEQ ID NO:54. In some embodiments, the MSAP (e.g., BSAP) comprises a first polypeptide comprising the amino acid sequence of SEQ ID NO:57, and a second polypeptide comprising the amino acid sequence of SEQ ID NO:61.

In some embodiments, there is provided a MSAP (such as BSAP) comprising: I. an anti-CD3 Fab fragment that specifically binds to CD3, optionally wherein the anti-CD3 Fab fragment comprises: (a) an Ig VH and an Ig CH1; and (b) an Ig VL and an Ig CL; wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment (e.g., scFv) comprises an HVR-H1 comprising the amino acid sequence of SEQ ID NO:1, an HVR-H2 comprising the amino acid sequence of SEQ ID NO: 2, and an HVR-H3 comprising the amino acid sequence of SEQ ID NO:3; and/or wherein the anti-CD19 antigen binding fragment (e.g., scFv) comprises a VL, wherein the VL of the anti-CD19 antigen binding fragment (e.g., scFv) comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 scFv that specifically binds to CD19, wherein the anti-CD19 scFv comprises a VH, wherein the VH of the anti-CD19 scFv comprises an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or wherein the anti-CD19 scFv comprises a VL, wherein the VL of the anti-CD19 scFv comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the anti-CD3 Fab fragment specifically binds to the N-terminus of CD38 (e.g., an epitope within amino acids 1-27 of CD38). In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO:18; and/or the CL of the anti-CD3 Fab fragment comprises the amino acid sequence of SEQ ID NO: 52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 scFv that specifically binds to CD19, wherein the anti-CD19 scFv comprises the amino acid sequence of SEQ ID NO:51 or 59; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:57, and a second polypeptide comprising the amino acid sequence of SEQ ID NO:54. In some embodiments, the MSAP (e.g., BSAP) comprises a first polypeptide comprising the amino acid sequence of SEQ ID NO:57, and a second polypeptide comprising the amino acid sequence of SEQ ID NO:61.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 antigen binding fragment (e.g., scFv) that specifically binds to CD19, wherein the anti-CD19 antigen binding fragment (e.g., scFv) comprises a VH, wherein the VH of the anti-CD19 antigen binding fragment comprises the amino acid sequence of SEQ ID NO:7; and/or wherein the anti-CD19 antigen binding fragment (e.g., scFv) comprises a VL, wherein the VL of the anti-CD19 antigen binding fragment comprises the amino acid sequence of SEQ ID NO: 8 or 50; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. an anti-CD19 scFv that specifically binds to CD19, wherein the VH of the anti-CD19 scFv comprises the amino acid sequence of SEQ ID NO:7; and/or wherein the VL of the anti-CD19 scFv comprises the amino acid sequence of SEQ ID NO:8 or 50; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:57, and a second polypeptide comprising the amino acid sequence of SEQ ID NO: 54. In some embodiments, the MSAP (e.g., BSAP) comprises a first polypeptide comprising the amino acid sequence of SEQ ID NO:57, and a second polypeptide comprising the amino acid sequence of SEQ ID NO:61.

In some embodiments, there is provided a MSAP (such as BSAP) comprising a first polypeptide and a second polypeptide, wherein the first polypeptide comprises the amino acid sequence of SEQ ID NO:57, and wherein the second polypeptide comprises the amino acid sequence of SEQ ID NO:54. In some embodiments, there is provided a MSAP (such as BSAP) comprising a first polypeptide and a second polypeptide, wherein the first polypeptide comprises the amino acid sequence of SEQ ID NO:57, and wherein the second polypeptide comprises the amino acid sequence of SEQ ID NO:61.

In some embodiments, the MSAP (such as BSAP) comprises a first anti-CD19 antigen binding fragment (e.g., scFv) and a second anti-CD19 antigen binding fragment (e.g., scFv), wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment.

Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the anti-CD3 Fab fragment specifically binds to the N-terminus of CD38 (e.g., an epitope within amino acids 1-27 of CD3E). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the first and/or the second anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO: 3; and/or a VL comprising: an HVR-L1 comprising the amino acid sequence of SEQ ID NO: 47, an HVR-L2 comprising the amino acid sequence of SEQ ID NO:48, and an HVR-L3 comprising the amino acid sequence of SEQ ID NO:6 or 49. In some embodiments, the first and/or the second anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the first and/or the second anti-CD19 scFv comprises the amino acid sequence of SEQ ID NO:51 or 59. In some embodiments, the first and the second anti-CD19 antigen binding fragments (e.g., scFvs) are identical in sequence. In some embodiments, the first and the second anti-CD19 antigen binding fragments (e.g., scFvs) have different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and/or the second linker comprises about 2 to about 30 (e.g., about 2 to about 15) amino acid residues selected from the group consisting of glycine, serine, arginine, and alanine. In some embodiments, the first and/or the second linker are selected from the group consisting of SEQ ID NOs: 20-22, 29, and 31-44 (e.g., SEQ ID NO:44). In some embodiments, the first and the second linkers are identical in sequence. In some embodiments, the first and the second linkers have different sequences. In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO:10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; wherein the first and/or the second anti-CD19 antigen binding fragment (e.g., scFv) comprises a VH, wherein the VH of the first and/or the second anti-CD19 antigen binding fragment (e.g., scFv) comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the first and/or the second anti-CD19 antigen binding fragment (e.g., scFv) comprises a VL, wherein the VL of the first and/or the second anti-CD19 antigen binding fragment (e.g., scFv) comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO: 6 or 49; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the VH of the first and/or the second anti-CD19 scFv comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the VL of the first and/or the second anti-CD19 scFv comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the anti-CD3 Fab fragment specifically binds to the N-terminus of CD38 (e.g., an epitope within amino acids 1-27 of CD3). In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the first and/or the second anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the first and/or the second anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the first and/or the second anti-CD19 scFv comprises the amino acid sequence of SEQ ID NO:51 or 59; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the first and the second anti-CD19 antigen binding fragments (e.g., scFvs) are identical in sequence. In some embodiments, the first and the second anti-CD19 antigen binding fragments (e.g., scFvs) have different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and/or the second linker comprises about 2 to about 30 (e.g., about 2 to about 15) amino acid residues selected from the group consisting of glycine, serine, arginine, and alanine. In some embodiments, the first and/or the second linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; wherein the first and/or the second anti-CD19 antigen binding fragment (e.g., scFv) comprises a VH, wherein the VH of the first and/or the second anti-CD19 antigen binding fragment (e.g., scFv) comprises the amino acid sequence of SEQ ID NO:7; and/or wherein the first and/or the second anti-CD19 antigen binding fragment (e.g., scFv) comprises a VL, wherein the VL of the first and/or the second anti-CD19 antigen binding fragment (e.g., scFv) comprises the amino acid sequence of SEQ ID NO:8 or 50; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO:14; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the VH of the first and/or the second anti-CD19 scFv comprises the amino acid sequence of SEQ ID NO: 7; and/or wherein the VL of the first and/or the second anti-CD19 scFv comprises the amino acid sequence of SEQ ID NO:8 or 50; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the first and/or the second anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the first and/or the second anti-CD19 scFv comprises the amino acid sequence of SEQ ID NO:51 or 59; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the first and the second anti-CD19 antigen binding fragments (e.g., scFvs) are identical in sequence. In some embodiments, the first and the second anti-CD19 antigen binding fragments (e.g., scFvs) have different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and/or the second linker comprises about 2 to about 30 (e.g., about 2 to about 15) amino acid residues selected from the group consisting of glycine, serine, arginine, and alanine. In some embodiments, the first and/or the second linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; wherein the first and/or the second anti-CD19 antigen binding fragment (e.g., scFv) comprises a VH, wherein the VH of the first and/or the second anti-CD19 antigen binding fragment (e.g., scFv) comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the first and/or the second anti-CD19 antigen binding fragment (e.g., scFv) comprises a VL, wherein the VL of the first and/or the second anti-CD19 antigen binding fragment (e.g., scFv) comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the VH of the first and/or the second anti-CD19 scFv comprises an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or wherein the VL of the first and/or the second anti-CD19 scFv comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the anti-CD3 Fab fragment specifically binds to the N-terminus of CD38 (e.g., an epitope within amino acids 1-27 of CD3E). In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the first and/or the second anti-CD19 antigen binding fragment (e.g., scFv) comprises a VH comprising the amino acid sequence of SEQ ID NO:7, and/or a VL comprising the amino acid sequence of SEQ ID NO: 8 or 50. In some embodiments, the first and/or the second anti-CD19 scFv comprises the amino acid sequence of SEQ ID NO:51 or 59. Thus in some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the first and/or the second anti-CD19 scFv comprises the amino acid sequence of SEQ ID NO: 51 or 59; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the first and the second anti-CD19 antigen binding fragments (e.g., scFvs) are identical in sequence. In some different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and/or the second linker comprises about 2 to about 30 (e.g., about 2 to about 15) amino acid residues selected from the group consisting of glycine, serine, arginine, and alanine. In some embodiments, the first and/or the second linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO: 54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61.

In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; wherein the first and/or the second anti-CD19 antigen binding fragment (e.g., scFv) comprises a VH, wherein the VH of the first and/or the second anti-CD19 antigen binding fragment (e.g., scFv) comprises the amino acid sequence of SEQ ID NO:7; and/or wherein the first and/or the second anti-CD19 antigen binding fragment (e.g., scFv) comprises a VL, wherein the VL of the first and/or the second anti-CD19 antigen binding fragment (e.g., scFv) comprises the amino acid sequence of SEQ ID NO:8 or 50; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, there is provided a MSAP (such as BSAP) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises the amino acid sequence of SEQ ID NO: 15; and/or wherein the VL of the anti-CD3 Fab fragment comprises the amino acid sequence of SEQ ID NO: 16; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the VH of the first and/or the second anti-CD19 scFv comprises the amino acid sequence of SEQ ID NO:7; and/or wherein the VL of the first and/or the second anti-CD19 scFv comprises the amino acid sequence of SEQ ID NO:8 or 50; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the first and/or the second anti-CD19 scFv comprises the amino acid sequence of SEQ ID NO:51 or 59. In some embodiments, the first and the second anti-CD19 antigen binding fragments (e.g., scFvs) are identical in sequence. In some embodiments, the first and the second anti-CD19 antigen binding fragments (e.g., scFvs) have different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs)

bind to different CD19 epitopes. In some embodiments, the first and/or the second linker comprises about 2 to about 30 (e.g., about 2 to about 15) amino acid residues selected from the group consisting of glycine, serine, arginine, and alanine. In some embodiments, the first and/or the second linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61.

In some embodiments, there is provided a MSAP (such as BSAP) comprising a first polypeptide and a second polypeptide, wherein the first polypeptide comprises the amino acid sequence of SEQ ID NO:53 or 60, and wherein the second polypeptide comprises the amino acid sequence of SEQ ID NO:54 or 61. In some embodiments, there is provided a MSAP (such as BSAP) comprising a first polypeptide and a second polypeptide, wherein the first polypeptide comprises the amino acid sequence of SEQ ID NO:53, and wherein the second polypeptide comprises the amino acid sequence of SEQ ID NO:54. In some embodiments, there is provided a MSAP (such as BSAP) comprising a first polypeptide and a second polypeptide, wherein the first polypeptide comprises the amino acid sequence of SEQ ID NO:60, and wherein the second polypeptide comprises the amino acid sequence of SEQ ID NO:61.

The invention further provides fusion proteins comprising any of the CD3×CD19 MSAPs (such as BSAPs) described herein, CD3×CD19 MSAP conjugates (e.g., small molecule drug conjugates), or isolated cells expressing any of the CD3×CD19 MSAPs described herein.

Anti-CD3 Fab Fragment

The anti-CD3 Fab fragment of the CD3×CD19 MSAPs (such as BSAPs) described herein specifically binds to CD3, such as human CD3. "CD3" is known in the art as a multi-protein complex of six chains (see, Abbas and Lichtman, 2003; Janeway et al., p 172 and 178, 1999). In mammals, the T cell receptor (TCR) complex comprises a CD3 gamma chain, a CD3 delta chain, two CD3 epsilon chains, and a homodimer of CD3 zeta chains. The CD3 gamma, CD3 delta, and CD3 epsilon chains are highly related cell surface proteins of the immunoglobulin superfamily containing a single immunoglobulin domain. The transmembrane regions of the CD3 gamma, CD3 delta, and CD3 epsilon chains are negatively charged, which is a characteristic that allows these chains to associate with the positively charged TCR chains. The intracellular tails of the CD3 gamma, CD3 delta, and CD3 epsilon chains each contain a single conserved motif known as an immunoreceptor tyrosine-based activation motif or ITAM, whereas each CD3 zeta chain has three. Without being bound by theory, it is believed the ITAMs are important for the signaling capacity of a TCR complex. CD3 as used herein may be from various animal species, including human, primate, mouse, rat, or other mammals.

In some embodiments, the CD3×CD19 MSAPs (such as BSAPs) described herein have an increased in vivo half-life compared to the anti-CD3 Fab fragment alone. In some embodiments, the CD3×CD19 MSAP (such as BSAP) has a half-life of at least about 1.5, 2, 3, 4, 5, 6, 7, 8, 9, 10, or more times the individual anti-CD3 Fab fragment.

In some embodiments, the anti-CD3 Fab fragment of the CD3×CD19 MSAP (such as BSAP) binds to CD3 with an equilibrium binding constant ($K_d$)≤1 μM, such as ≤100 nM, preferably ≤10 nM, more preferably ≤1 nM. For example, the $K_d$ value of the anti-CD3 Fab fragment is between about ≤1 nM and about 1 pM. In some embodiments, the anti-CD3 Fab fragment binds to human CD3 with a $K_d$ of about $0.1 \times 10^{-9}$ M to about $1 \times 10^{-7}$ M, such as about $5.99 \times 10^{-9}$ M. In some embodiments, the anti-CD3 Fab fragment binds to a monkey (e.g., cynomolgus) CD3 with a $K_d$ of about $0.1 \times 10^{-9}$ M to about $1 \times 10^{-7}$ M, such as about $1.88 \times 10^{-8}$ M.

In some embodiments, the anti-CD3 Fab fragment of the CD3×CD19 MSAP (such as BSAP) specifically binds to an individual CD3 chain, such as CD3 gamma chain, CD3 delta chain, or CD3 epsilon chain. In some embodiments, the anti-CD3 Fab fragment specifically binds to a complex formed from two or more individual CD3 chains (e.g., a complex of more than one CD3 epsilon chains, a complex of a CD3 gamma and CD3 epsilon chain, a complex of a CD3 delta and CD3 epsilon chain). In some embodiments, the anti-CD3 Fab fragment specifically binds to a CD3 epsilon chain. In some embodiments, the anti-CD3 Fab fragment specifically binds to the N-terminus of CD3 epsilon. In some embodiments, the anti-CD3 Fab fragment specifically binds to an epitope within amino acids 1-27 of CD3 epsilon.

The anti-CD3 Fab fragments can be generated by a variety of methods known in the art (see, e.g., U.S. Pat. Nos. 6,291,161; 6,291,158). Sources of anti-CD3 Fabs include monoclonal antibody or antigen-binding fragments thereof from various species, including human, camelid (from camels, dromedaries, or llamas; Hamers-Casterman et al. (1993) Nature, 363:446 and Nguyen et al. (1998) J. Mol. Biol., 275:413), shark (Roux et al. (1998) Proc. Nat'l. Acad. Sci. (USA) 95:11804), fish (Nguyen et al. (2002) Immunogenetics, 54:39), rodent, avian, or ovine. In some embodiments, the anti-CD3 Fab fragment is derived from a human or humanized antibody. In some embodiments, the anti-CD3 Fab fragment is chimeric. In some embodiments, the anti-CD3 Fab fragment is derived from a fully human antibody, for example, developed using phage-display, yeast-display, or transgenic mice bearing human Ig genes.

In some embodiments, the anti-CD3 Fab fragment specifically binds to both human and non-human primates (such as cynomolgus monkey) CD3. Exemplary anti-human CD3 antibody with cross reactivity to monkey CD3 include, but are not limited to, SP34 mouse monoclonal antibody, (see, for example, Pressano, S. The EMBO J. 4:337-344, 1985; Alarcon, B. EMBO J. 10:903-912, 1991; Salmeron A. et al., J. Immunol. 147:3047-52, 1991; Yoshino N. et al., Exp. Anim 49:97-110, 2000; Conrad M L. et al., Cytometry 71A: 925-33, 2007; and Yang et al., J. Immunol. 137:1097-1100: 1986). CD3×CD19 MSAPs (such as BSAPs) having anti-CD3 Fab fragments with cross-reactivity to monkey CD3 may facilitate toxicity studies in non-human primates, which can provide more relevant safety assessments for human clinical trial candidates, without having to perform toxicity studies in chimpanzees or using surrogate molecules.

In some embodiments, the anti-CD3 Fab fragment is derived from an anti-CD3 antibody that does not have cross-reactivity to non-human primates. Exemplary anti-CD3 antibodies include the Cris-7 monoclonal antibody (Reinherz, E. L. et al. (eds.), Leukocyte typing II, Springer Verlag, New York, (1986)), BC3 monoclonal antibody (Anasetti et al. (1990) J. Exp. Med. 172:1691), OKT3 (Ortho multicenter Transplant Study Group (1985) N. Engl. J. Med.

313:337) and derivatives thereof such as OKT3 ala-ala (Herold et al. (2003) J. Clin. Invest. 11:409), visilizumab (Carpenter et al. (2002) Blood 99:2712), and 145-2C11 monoclonal antibody (Hirsch et al. (1988) J. Immunol. 140:3766). Further CD3 binding molecules contemplated herein include UCHT-1 (Beverley, P C and Callard, R. E. (1981) Eur. J. Immunol. 11:329-334) and CD3 binding molecules described in WO2004/106380; WO2010/037838; WO2008/119567; WO2007/042261; WO2010/0150918.

In some embodiments, the anti-CD3 Fab fragment comprises one constant (CH1) and one variable (VH) region of an immunoglobulin (Ig) heavy chain, and one constant (CL) and one variable (VL) region of an Ig light chain. In some embodiments, the CH1 and VH heterodimerize with the VL and CL, and are covalently linked by a disulfide bond between the heavy and light chain constant regions. In some embodiments, the anti-CD3 Fab fragment has the basic structure NH$_2$-VL-CL-S-S-CH1-VH-NH$_2$. In some embodiments, the CH1 and the CL of the anti-CD3 Fab fragment are connected by one or more disulfide bonds. In some embodiments, the number of disulfide bonds between CH1 and CL of the anti-CD3 Fab fragment is at least one, such as 2, 3, 4, or more. In some embodiments, cysteine residues are engineered in the anti-CD3 Fab fragment (such as in the CH1 and CL regions) to introduce disulfide bonds.

In some embodiments, the anti-CD3 Fab fragment of the CD3×CD19 MSAP (such as BSAP) does not comprise a disulfide bond. For example, the heavy and light chains may be engineered in such a way so as to stably interact without the need for disulfide bonds. In some embodiments, the heavy chain or light chain can be engineered to remove a cysteine residue, and wherein the heavy and light chains still stably interact and function as a Fab. In some embodiments, mutations are made to facilitate stable interactions between the heavy and light chains. For example, a "knobs into holes" engineering strategy can be used to facilitate dimerization between the heavy and light chains of a Fab (see e.g., 1996 Protein Engineering, 9:617-621). Also contemplated for use herein are variant Fab fragments designed for a particular purpose, for example, amino acid changes in the constant domains of CH1 and/or CL, and removal of a disulfide bond or addition of tags for purification, etc.

In some embodiments, the configuration of the variable and constant regions within the anti-CD3 Fab fragment may be different from what is found in a native anti-CD3 Fab. In some embodiments, the orientation of the variable and constant regions may be VH-CL in one chain, and VL-CH1 in another chain (see, for example, Shaefer et al. (2011), PNAS, 108:111870-92).

In some embodiments, the anti-CD3 Fab fragments of the CD3×CD19 MSAP (such as BSAP) are derived from monoclonal antibodies. Suitable monoclonal antibodies may be of any type, including IgA, IgM, IgD, IgG, IgE and subtypes thereof, such as IgG1, IgG2, IgG3, and IgG4. The light chain domains may be derived from the kappa or lambda chain. In some embodiments, the anti-CD3 Fab fragment is designed recombinantly.

In some embodiments, the anti-CD3 Fab fragment comprises a human immunoglobulin CH1. In some embodiments, the human immunoglobulin CH1 comprises the amino acid sequence of SEQ ID NO: 18. In some embodiment, the anti-CD3 Fab fragment comprises a human lambda light chain constant region. In one embodiment, the human lambda light chain constant region comprises the amino acid sequence of SEQ ID NO:52. In some embodiments, the CH1 and the CL of the anti-CD3 Fab fragment are connected by about 1 to about 5 (such as 1, 2, 3, 4, or 5)

disulfide bonds. In some embodiments, the CH1 and the CL of the anti-CD3 Fab fragment are connected by about 2 disulfide bonds. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond.

SEQ ID NO:18 (human CH1) ASTKGPSVF-PLAPSSKSTSGGTAALGCLVKDYFPEPVTVS-WNSGALTSGVHTFPAVLQSS GLYSLSSVVTV-PSSSLGTQTYICNVNHKPSNTKVDKKVEPKS
    SEQ ID NO:52 (human lambda CL) GQP-KAAPSVTLFPPSSEELQANKATLVCLISDFYP-GAVTVAWKADSSPVKAGVETTTPS KQSNNKYAASSYLSLTPEQWKSHRSYS-CQVTHEGSTVEKTVAPTE The anti-CD3 Fab fragment of the CD3×CD19 MSAP (such as BSAP) specifically binds to CD3 via an antigen-binding site formed between the heavy chain variable region (VH) and the light chain variable region (VL). The antigen-binding site comprises at least one (such as 1, 2, or 3) HVR of an immunoglobulin heavy chain and/or at least one (such as 1, 2, or 3) HVR of an immunoglobulin light chain. In some embodiments, the CD3×CD19 MSAP (such as BSAP) comprises 1, 2, 3, 4, 5, or all 6 HVRs of a VH and VL sequence of a full-length antibody that specifically binds to CD3.

In some embodiments, the anti-CD3 Fab fragment is derived from SP34. In some embodiments, the anti-CD3 Fab fragment is a CD3 Fab fragment described in U.S. Pat. No. 8,846,042. In some embodiments, the anti-CD3 Fab fragment comprises a VH comprising one, two or three HVRs (or CDRs) from SEQ ID NO: 15, and/or a VL comprising one, two or three HVRs (or CDRs) from SEQ ID NO:16. In some embodiments, the anti-CD3 Fab fragment comprises a VH comprising three HVRs from SEQ ID NO:15, and/or a VL comprising three HVRs from SEQ ID NO:16. In some embodiments, the anti-CD3 Fab fragment comprises a VH comprising one, two or three HVRs selected from SEQ ID NOs: 9-11, and/or a VL comprising one, two or three HVRs selected from SEQ ID NOs: 12-14. In some embodiments, the anti-CD3 Fab fragment comprises a VH comprising: an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or a VL comprising: an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO:14. In some embodiments, the anti-CD3 Fab fragment comprises a VH comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the amino acid sequence of SEQ ID NO:15. In some embodiments, the anti-CD3 Fab fragment comprises a VL comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the amino acid sequence of SEQ ID NO: 16. In some embodiments, a VH or VL sequence having at least 90%, 91%, 92%, 93%, 94%, 95%, 96%, 97%, 98%, or 99% identity contains substitutions (e.g., conservative substitutions), insertions, or deletions relative to the reference sequence, but the anti-CD3 Fab fragment comprising that sequence retains the ability to bind to CD3. In some embodiments, one or two amino acids have been substituted, inserted and/or deleted in any one or more of the HVRs. In some embodiments, substitutions, insertions, or deletions occur in regions outside the HVRs (i.e., in the framework regions, "FRs"). In some embodiments, the anti-CD3 Fab fragment comprises a VH comprising the amino acid sequence of SEQ ID NO:15, and/or a VL comprising the amino acid sequence of SEQ ID NO:16. In some embodiments, the anti-CD3 Fab fragment comprises a heavy chain polypeptide comprising the amino acid sequence of SEQ ID NO:57; and/or a light chain polypeptide comprising the amino acid sequence of SEQ ID NO:58.

```
(anti-CD3 HVR-H1)
                                      SEQ ID NO: 9
TYAMN (anti-CD3 HVR-H2)
                                      SEQ ID NO: 10
RIRSKYNNYATYYADSVKD (anti-CD3 HVR-H3)
                                      SEQ ID NO: 11
HGNFGNSYVSWFAY (anti-CD3 HVR-L1)
                                      SEQ ID NO: 12
RSSTGAVTTSNYAN (anti-CD3 HVR-L2)
                                      SEQ ID NO: 13
GTNKRAP (anti-CD3 HVR-L3)
                                      SEQ ID NO: 14
ALWYSNLWV (anti-CD3 VH; HVRs are underlined)
                                      SEQ ID NO: 15
EVQLVESGGGLVQPGGSLRLSCAASGFTFNTYAMNWVRQAPGKGLEWVAR

IRSKYNNYATYYADSVKDRFTISRDDSKNTLYLQMNSLRAEDTAVYYCVR

HGNFGNSYVSWFAYWGQGTMVTVSS (anti-CD3 VL; HVRs are underlined)
                                      SEQ ID NO: 16
QAVVTQEPSLTVSPGGTVTLTCRSSTGAVTTSNYANWVQQKPGQAPRGLI

GGTNKRAPGTPARFSGSLLGGKAALTLSGVQPEDEAEYYCALWYSNLWVF

GGGTKLTVL (anti-CD3 Fab fragment Fd polypeptide; HVRs are
underlined)
                                      SEQ ID NO: 57
EVQLVESGGGLVQPGGSLRLSCAASGFTFNTYAMNWVRQAPGKGLEWVAR

IRSKYNNYATYYADSVKDRFTISRDDSKNTLYLQMNSLRAEDTAVYYCVR

HGNFGNSYVSWFAYWGQGTMVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCPPCS
```

-continued

```
(anti-CD3 Fab fragment light chain polypeptide;
HVRs are underlined)
                                      SEQ ID NO: 58
QAVVTQEPSLTVSPGGTVTLTCRSSTGAVTTSNYANWVQQKPGQAPRGLI

GGTNKRAPGTPARFSGSLLGGKAALTLSGVQPEDEAEYYCALWYSNLWVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECPPCS
```

In some embodiments, a specific VH and/or VL of an anti-CD3 Fab fragment may be used to screen a library of the complementary variable region to identify VH/VL with desirable properties, such as increased affinity for CD3. Such methods are described, for example, in Portolano et al., J. Immunol. (1993) 150:880-887; Clarkson et al., Nature (1991) 352:624-628; and Klimka et al., British Journal of Cancer (2000) 83:252-260; Beiboer et al., J. Mol. Biol. (2000) 296:833-849; and Rader et al., PNAS (1998) 95:8910-8915.

Anti-CD19 Antigen Binding Fragment

The CD3×CD19 MSAPs (such as BSAPs) described herein comprises one or two anti-CD19 antigen binding fragments (e.g., scFv) that specifically bind to CD19. In some embodiments, the anti-CD19 antigen binding fragment (e.g., scFv) is fused at the N-terminus of the anti-CD3 Fab fragment, e.g., at the N-terminus of the VH of the anti-CD3 Fab fragment and/or at the N-terminus of the VL of the anti-CD3 Fab fragment.

The B-lymphocyte antigen CD19 is also known as CD19 molecule (cluster of differentiation 19), B-lymphocyte surface antigen B4, T-cell surface antigen Leu-12 and CVID3. In humans, CD19 is expressed in all B lineage cells, except for plasma cells, and in follicular dendritic cells. CD19 has two major roles: 1) acting as an adaptor protein to recruit cytoplasmic signaling proteins to the membrane; and 2) functioning within the CD19/CD21 complex to decrease the threshold for B cell receptor signaling pathways. CD19 is expressed in both normal B lymphocytes and malignant B lymphocytes, and is considered a B-cell tumor-associated antigen. For example, CD19 can serve as a biomarker for B lymphocyte development, a cancer diagnosis marker, or a target for immunotherapy, such as for B cell lymphomas, mantle cell lymphoma (MCL), acute lymphoblastic leukemia (ALL), and chronic lymphocytic leukemia (CLL).

In some embodiments, the anti-CD19 antigen binding fragment (e.g., scFv) can specifically binds to CD19 on a cell surface. In some embodiments, the cell is a cancer cell. In some embodiments, the cancer cell is in a solid tumor. In some embodiments, the cancer cell is a metastatic cancer cell, such as a hematologic cancer, e.g., ALL, CLL, MCL, B cell lymphoma, and the like.

In some embodiments, the CD3×CD19 MSAPs (such as BSAPs) described herein have an increased in vivo half-life compared to the anti-CD19 antigen binding fragment (e.g., scFv) alone. In some embodiments, the CD3×CD19 MSAP (such as BSAP) has a half-life of at least about 1.5, 2, 3, 4, 5, 6, 7, 8, 9, 10, or more times the individual anti-CD19 antigen binding fragment (e.g., scFv).

In some embodiments, the anti-CD19 antigen binding fragment (e.g., scFv) of the CD3×CD19 MSAP (such as BSAP) binds to CD19 with an equilibrium binding constant $(K_d) \leq 1$ µM, such as $\leq 100$ nM, preferably $\leq 10$ nM, more preferably $\leq 1$ nM. For example, the $K_d$ value of the anti- CD19 antigen binding fragment (e.g., scFv) is between about $\leq 1$ nM and about 1 pM. In some embodiments, the anti-CD19 antigen binding fragment (e.g., scFv) binds to human CD19 with a $K_d$ of about $0.01 \times 10^{-9}$ M to about $1 \times 10^{-7}$ M, such as about $8.91 \times 10^{-10}$ M. In some embodiments, the anti-CD19 antigen binding fragment (e.g., scFv) binds to a monkey (e.g., cynomolgus) CD19 with a $K_d$ of about $0.1 \times 10^{-9}$ M to about $1 \times 10^{-7}$ M, such as about $8.91 \times 10^{-9}$ M.

The anti-CD19 antigen binding fragment (e.g., scFv) in the CD3×CD19 MSAP (such as BSAP) not only provides additional binding specificities and enhanced properties (e.g., increased serum half-life, or activation of immune activation cascades), but also creates steric hindrance to significantly reduce the binding affinity of the anti-CD3 Fab fragment to CD3 due to fusion to the N terminus of the VH and/or VL chains. This is in direct contrast to other Fab fusion proteins, such as TRIBODIES™, which fuses additional binding domains at the C terminus of the Fab fragment (see, e.g., Journal of Immunology, 2000, 165:7050-7057). The anti-CD19 antigen binding fragments (e.g., scFvs) are not intended to dimerize, unlike other known fusion proteins, such as those described in WO2008/024188 and WO2009/149185. A further distinguishing characteristic of the CD3×CD19 MSAP (such as BSAP) is that the anti-CD19 antigen binding fragments (e.g., scFvs) reduce the binding affinity of the anti-CD3 Fab fragment to CD3 when the MSAP (such as BSAP) is not bound to CD19 on tumor cells.

The anti-CD19 antigen binding fragments described herein can be of any format and derived from any suitable anti-CD19 antibodies. For example, the anti-CD19 antigen binding fragment can be selected from an scFv, a VH, a VL, an scFv-scFv, an Fv, a Fab, a Fab', a (Fab')2, a minibody, a diabody, a domain antibody variant (dAb), a single domain antibody (sdAb), a camelid antibody (VHH), a fibronectin 3 domain variant, an ankyrin repeat variant, and other antigen-specific binding domains derived from other protein scaffolds. In some embodiments, the anti-CD19 antigen binding fragment is an scFv. In some embodiments, the anti-CD19 antigen binding fragment (e.g., scFv) is humanized. In some embodiments, the anti-CD19 antigen binding fragment (e.g., scFv) is chimeric. In some embodiments, the anti-CD19 antigen binding fragment (e.g., scFv) is derived from a monoclonal antibody of mouse, rat, monkey or rabbit. In some embodiments, the anti-CD19 antigen binding fragment (e.g., scFv) is derived from any monoclonal antibodies selected from B43, MEDI-551, CLB-CD19, 4G7, SJ25-CILT19, Leu-12, HD37, or any other known anti-CD19 antibodies. In some embodiments, the anti-CD19 antigen binding fragment (e.g., scFv) is derived from a fully human antibody, for example, developed using phage-display, yeast-display, or transgenic mice bearing human Ig genes.

In some embodiments, the anti-CD19 antigen binding fragment (e.g., scFv) specifically binds to both human and non-human primates (such as cynomolgus monkey) CD19. CD3×CD19 MSAPs (such as BSAPs) having anti-CD19 antigen binding fragment (e.g., scFv) with cross-reactivity to monkey CD19 may facilitate toxicity studies in non-human primates, which can provide more relevant safety assessments for human clinical trial candidates, without having to perform toxicity studies in chimpanzees or using surrogate molecules.

The anti-CD19 antigen binding fragment (e.g., scFv) of the invention may fully or partially modulate, block, inhibit, reduce, antagonize, neutralize or interfere with the functional activity of CD19. When the functional activity of CD19 is reduced by at least 95% (such as 96%, 97%, 98%, 99% or 100%) in the presence of an anti-CD19 antigen binding fragment (e.g., scFv) compared to not bound by an anti-CD19 antigen binding fragment (e.g., scFv), the anti-CD19 antigen binding fragment (e.g., scFv) is considered capable of fully modulating, blocking, inhibiting, reducing, antagonizing, neutralizing or interfering with the functional activity of CD19. When the functional activity of CD19 is reduced by at least 50% (such as 55%, 60%, 75%, 80%, 85%, or 90%) in the presence of an anti-CD19 antigen binding fragment (e.g., scFv) compared to not bound by an anti-CD19 antigen binding fragment (e.g., scFv), the anti-CD19 antigen binding fragment (e.g., scFv) is considered capable of significantly modulating, blocking, inhibiting, reducing, antagonizing, neutralizing or interfering with the functional activity of CD19. When the functional activity of CD19 is reduced by less than 95% (such as reduced by 10%, 20%, 25%, 30%, 40%, 50%, 60%, 75%, 80%, 85%, or 90%) in the presence of an anti-CD19 antigen binding fragment (e.g., scFv) compared to not bound by an anti-CD19 antigen binding fragment (e.g., scFv), the anti-CD19 antigen binding fragment (e.g., scFv) is considered capable of partially modulating, blocking, inhibiting, reducing, antagonizing, neutralizing or interfering with the functional activity of CD19.

In some embodiments, the anti-CD19 antigen binding fragment (e.g., scFv) comprises a particular sequence or certain variants of these sequences. In some embodiments, the amino acid substitutions in the variant sequences do not substantially reduce the ability of the anti-CD19 antigen binding fragment (e.g., scFv) to bind to CD19. Also contemplated are modifications that substantially improve the binding affinity of the anti-CD19 antigen binding fragment (e.g., scFv) to CD19 or other properties, such as specificity, immunogenicity, antibody-dependent cellular cytotoxicity (ADCC) or Complement-Dependent Cytotoxicity (CDC), and/or cross-reactivity with CD19 variants.

The anti-CD19 antigen binding fragment (e.g., scFv) may comprise at least one (such as 1, 2, or 3) HVR of an immunoglobulin heavy chain and/or at least one (such as 1, 2, or 3) HVR of an immunoglobulin light chain of a full-length antibody that specifically binds to CD19. In some embodiments, the anti-CD19 antigen binding fragment (e.g., scFv) comprises 1, 2, 3, 4, 5, or all 6 HVRs of a VH and VL sequence of a full-length antibody that specifically binds to CD19.

In some embodiments, the anti-CD19 antigen binding fragment is an scFv that specifically binds to CD19 (also referred herein as "anti-CD19 scFv"). In some embodiments, the VH and VL of the anti-CD19 scFv are connected to each other via a peptide linker, such as a flexible linker comprising glycines and/or serines. Any peptide linkers in the "Linkers" subsection below can be used as linking peptide in between VH and VL of the anti-CD19 scFv. In some embodiments, the VH and VL of the anti-CD19 scFv are connected to each other directly. In some embodiments, the anti-CD19 scFv comprises an N'-VH-L-VL-C' fusion polypeptide, wherein L is an optional peptide linker. In some embodiments, the anti-CD19 scFv comprises an N'-VL-L-VH-C' fusion polypeptide, wherein L is an optional peptide linker.

In some embodiments, the anti-CD19 antigen binding fragment (e.g., scFv) comprises a VH and/or a VL. In some embodiments, the anti-CD19 antigen binding fragment (e.g., scFv) comprises a VH comprising one, two or three HVRs (or CDRs) from SEQ ID NO:7, and/or a VL comprising one, two or three HVRs (or CDRs) from SEQ ID NO:8 or 50. In some embodiments, the anti-CD19 antigen binding fragment (e.g., scFv) comprises a VH comprising one, two or three HVRs (or CDRs) from SEQ ID NO:7, and/or a VL comprising one, two or three HVRs (or CDRs) from SEQ ID NO:50. In some embodiments, the anti-CD19 antigen binding fragment (e.g., scFv) comprises a VH comprising three HVRs from SEQ ID NO:7, and/or a VL comprising three HVRs from SEQ ID NO:8 or 50. In some embodiments, the anti-CD19 antigen binding fragment (e.g., scFv) comprises a VH comprising three HVRs from SEQ ID NO:7, and/or a VL comprising three HVRs from SEQ ID NO:50. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO: 2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:49. In some embodiments, the anti-CD19 antigen binding fragment (e.g., scFv) comprises a VH comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:7, and/or a VL comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:8 or 50 (such as SEQ ID NO:50). In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 antigen binding fragment (e.g., scFv) comprises a VH comprising the amino acid sequence of SEQ ID NO:7, and/or a VL comprising the amino acid sequence of SEQ ID NO:50. In some embodiments, the anti-CD19 antigen binding fragment is an scFv. In some embodiments, the anti-CD19 scFv comprises the amino acid sequence of SEQ ID NO:51 or 59. In some embodiments, the anti-CD19 scFv comprises the amino acid sequence of SEQ ID NO: 51.

```
(anti-CD19 HVR-H1)
                                        SEQ ID NO: 1
SYVMH (anti-CD19 HVR-H2)
                                        SEQ ID NO: 2
WIGYINPYNDGTKY
```

-continued

```
(anti-CD19 HVR-H3)
                                     SEQ ID NO: 3
GTYYYGSRVFDY (anti-CD19 HVR-L1-1.3)
                                    SEQ ID NO: 47
RSSKSLQNVNGNTYLY (anti-CD19 HVR-L2-1.3)
                                    SEQ ID NO: 48
RMSNLNS (anti-CD19 HVR-L3-1.3)
                                    SEQ ID NO: 49
MQHLEYPLT (anti-CD19 HVR-L1-1.2)
                                     SEQ ID NO: 4
RSSKSLQNVNGNTYLY (anti-CD19 HVR-L2-1.2)
                                     SEQ ID NO: 5
RMSNLNS (anti-CD19 HVR-L3-1.2)
                                     SEQ ID NO: 6
MQHLEYPIT (anti-CD19 VH; HVRs are underlined)
                                     SEQ ID NO: 7
QVQLVQSGPELIKPGGSVKMSCKASGYTFTSYVMHWVRQKPGQGLEWIGY

INPYNDGTKYNEKFKGRATLTSDKSSSTAYMELSSLRSEDSAVYYCARGT

YYYGSRVFDYWGQGTTVTVSS (anti-CD19 VL1.3; HVRs are underlined)
                                    SEQ ID NO: 50
DVVMTQSPSSIPVTLGESVSISCRSSKSLQNVNGNTYLYWFQQRPGQSPQ

LLIYRMSNLNSGVPDRFSGSGSGTDFTLRISGVEPEDVGVYYCMQHLEYP

LTFGAGTKLEIK (anti-CD19 VL1.2; HVRs are underlined)
                                     SEQ ID NO: 8
DVVMTQSPSSIPVTLGESVSISCRSSKSLQNVNGNTYLYWFQQRPGQSPQ

LLIYRMSNLNSGVPDRFSGSGSGTDFTLRISGVEPEDVGVYYCMQHLEYP

ITFGAGTKLEIK (anti-CD19 scFv (VL-VH) 1.3); HVRs are underlined,
peptide linker is bolded)
                                    SEQ ID NO: 51
DVVMTQSPSSIPVTLGESVSISCRSSKSLQNVNGNTYLYWFQQRPGQSPQ

LLIYRMSNLNSGVPDRFSGSGSGTDFTLRISGVEPEDVGVYYCMQHLEYP

LTFGAGTKLEIKGGGGSGGGGSGGGGSQVQLVQSGPELIKPGGSVKMSCK

ASGYTFTSYVMHWVRQKPGQGLEWIGYINPYNDGTKYNEKFKGRATLTSD

KSSSTAYMELSSLRSEDSAVYYCARGTYYYGSRVFDYWGQGTTVTVSS (anti-CD19 scFv (VL-VH) 1.2); HVRs are underlined,
peptide linker is bolded)
                                    SEQ ID NO: 59
DVVMTQSPSSIPVTLGESVSISCRSSKSLQNVNGNTYLYWFQQRPGQSPQ

LLIYRMSNLNSGVPDRFSGSGSGTDFTLRISGVEPEDVGVYYCMQHLEYP

ITFGAGTKLEIKGGGGSGGGGSGGGGSQVQLVQSGPELIKPGGSVKMSCK

ASGYTFTSYVMHWVRQKPGQGLEWIGYINPYNDGTKYNEKFKGRATLTSD

KSSSTAYMELSSLRSEDSAVYYCARGTYYYGSRVFDYWGQGTTVTVSS
```

Linkers

The CD3×CD19 MSAPs (such as BSAPs) described herein may comprise a linker (such as a peptide linker)

connecting the VH or the VL of the anti-CD3 Fab fragment and the anti-CD19 antigen binding fragment (e.g., scFv). In some embodiments, the CD3×CD19 MSAP (such as BSAP) comprises two anti-CD19 antigen binding fragments (e.g., scFvs). In some embodiments, the linker between the VH of the anti-CD3 Fab fragment and the first anti-CD19 antigen binding fragment (e.g., scFv) is the same as the linker between the VL of the anti-CD3 Fab fragment and the second anti-CD19 antigen binding fragment (e.g., scFv). In some embodiments, the linker between the VH of the anti-CD3 Fab fragment and the first anti-CD19 antigen binding fragment (e.g., scFv) is different from the linker between the VL of the anti-CD3 Fab fragment and the second anti-CD19 antigen binding fragment (e.g., scFv). In some embodiments, the anti-CD19 antigen binding fragment is an scFv. In some embodiments, the anti-CD19 scFv comprises a linker (such as peptide linker) connecting the VH and VL of the anti-CD19 scFv, which may be the same or different from any of the linkers between the VH and VL of the anti-CD3 Fab fragment and the anti-CD19 scFvs.

The linkers can be peptide linkers of any length. In some embodiments, the peptide linker is from about 1 amino acid to about 10 amino acids long, from about 2 amino acids to about 15 amino acids long, from about 3 amino acids to about 12 amino acids long, from about 4 amino acids to about 10 amino acids long, from about 5 amino acids to about 9 amino acids long, from about 6 amino acids to about 8 amino acids long, from about 1 amino acid to about 20 amino acids long, from about 21 amino acids to about 30 amino acids long, from about 1 amino acid to about 30 amino acids long, from about 2 amino acids to about 20 amino acids long, from about 10 amino acids to about 30 amino acids long, from about 2 amino acids to about 19 amino acids long, from about 2 amino acids to about 18 amino acids long, from about 2 amino acids to about 17 amino acids long, from about 2 amino acids to about 16 amino acids long, from about 2 amino acids to about 10 amino acids long, from about 2 amino acids to about 14 amino acids long, from about 2 amino acids to about 13 amino acids long, from about 2 amino acids to about 12 amino acids long, from about 2 amino acids to about 11 amino acids long, from about 2 amino acids to about 9 amino acids long, from about 2 amino acids to about 8 amino acids long, from about 2 amino acids to about 7 amino acids long, from about 2 amino acids to about 6 amino acids long, from about 2 amino acids to about 5 amino acids long, from about 2 amino acids to about 4 amino acids long, or from about 2 amino acids to about 3 amino acids long. In some embodiments, the peptide linker is any of 1, 2, 3, 4, 5, 6, 7, 8, 9, 10, 11, 12, 13, 14, 15, 16, 17, 18, 19 or 20 amino acids long. In some embodiments, the peptide linker is any of 21, 22, 23, 24, 25, 26, 27, 28, 29, or 30 amino acids long. For example, in some embodiments, the peptide linker is about 5 amino acids long. In some embodiments, the N-terminus of the peptide linker is covalently linked to the C-terminus of the anti-CD19 antigen binding fragment (e.g., scFv), and the C terminus of the peptide linker is covalently linked to the N-terminus of the VH or VL of the anti-CD3 Fab fragment.

A peptide linker can have a naturally occurring sequence or a non-naturally occurring sequence. For example, a sequence derived from the hinge region of a heavy chain only antibody can be used as a linker. See, for example, WO1996/34103. In some embodiments, the peptide linker is a human IgG1 or IgG4 hinge. In some embodiments, the peptide linker is a mutated human IgG1 or IgG4 hinge. In some embodiments, the linker is a flexible linker. Exemplary flexible linkers include glycine polymers $(G)_n$ (SEQ ID NO:31), glycine-serine polymers (including, for example, (GS)$_n$ (SEQ ID NO:32), (GSGGS)$_n$ (SEQ ID NO:33), (GGGS)$_n$ (SEQ ID NO: 34), or (GGGGS)$_n$ (SEQ ID NO:35), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11 173-142 (1992)). Exemplary flexible linkers include, but are not limited to Gly-Gly (SEQ ID NO:36), Gly-Gly-Ser-Gly (SEQ ID NO:37), Gly-Gly-Ser-Gly-Gly (SEQ ID NO:38), Gly-Ser-Gly-Ser-Gly (SEQ ID NO:39), Gly-Ser-Gly-Gly-Gly (SEQ ID NO: 40), Gly-Gly-Gly-Ser-Gly (SEQ ID NO:41), Gly-Ser-Ser-Ser-Gly (SEQ ID NO:42), Gly-Gly-Ser-Gly-Gly-Ser (SEQ ID NO:20), Ser-Gly-Gly-Gly-Gly-Ser (SEQ ID NO:21), Gly-Arg-Ala-Gly-Gly-Gly-Gly-Ala-Gly-Gly-Gly-Gly (SEQ ID NO:22), Gly-Arg-Ala-Gly-Gly-Gly (SEQ ID NO: 29), GGGGSGGGGSGGGGS (SEQ ID NO:43), GGGGS (SEQ ID NO:44), and the like. In some embodiments, the linker between the VH of the anti-CD3 Fab fragment and the anti-CD19 antigen binding fragment (e.g., scFv) is GGGGS (SEQ ID NO:44). In some embodiments, the linker between the VL of the anti-CD3 Fab fragment and the anti-CD19 antigen binding fragment (e.g., scFv) is GGGGS (SEQ ID NO:44). In some embodiments, the linker connecting the VH and VL of the ani-CD19 scFv is GGGGSGGGGSGGGGS (SEQ ID NO:43). The ordinarily skilled artisan will recognize that design of a CD3×CD19 MSAP (such as BSAP) can include linkers that are all or partially flexible, such that the linker can include a flexible linker portion as well as one or more portions that confer less flexible structure to provide a desired CD3×CD19 MSAP (such as BSAP) structure.

In some embodiments, the linker between the anti-CD3 Fab fragment and the anti-CD19 antigen binding fragment (e.g., scFv) is a stable linker (not cleavable by protease, especially MMPs).

In some embodiments, the linker is a cleavable linker. In some embodiments, the linker between the VH or VL of the anti-CD3 Fab fragment and the anti-CD19 antigen binding fragment (e.g., scFv) comprises a protease substrate cleavage sequence, for example, an MMP substrate cleavage sequence. Substrate sequences that can be cleaved by MMPs have been extensively studied. For example, the sequence of PLGLAG (SEQ ID NO:30) can be cleaved by most MMPs. In some embodiments, the protease cleavage site is recognized by MMP-2, MMP-9, or a combination thereof.

In some embodiments, the CD3×CD19 MSAP (such as BSAP) described herein comprises a first polypeptide comprising the structure: N'-anti-CD19 VH-L1-anti-CD19 VL-L2-anti-CD3 VH-CH1-C', and a second polypeptide comprising the structure: N'-anti-CD3 VL-CL-C'. In some embodiments, the CD3×CD19 MSAP (such as BSAP) comprises a first polypeptide comprising the structure: N'-anti-CD19 VL-L1-anti-CD19 VH-L2-anti-CD3 VH-CH1-C', and a second polypeptide comprising the structure: N'-anti-CD3 VL-CL-C'. In some embodiments, the CD3×CD19 MSAP (such as BSAP) comprises a first polypeptide comprising the structure: N'-anti-CD3 VH-CH1-C', and a second polypeptide comprising the structure: N'-anti-CD19 VH-L1-anti-CD19 VL-L2-anti-CD3 VL-CL-C'. In some embodiments, the CD3×CD19 MSAP (such as BSAP) comprises a first polypeptide comprising the structure: N'-anti-CD19 VL-L1-anti-CD19 VH-L2-anti-CD3 VL-CL-C'. In some embodiments, the CD3×CD19 MSAP (such as BSAP) comprises a first polypeptide comprising the structure: N'-anti-CD19 VH-L1-anti-CD19 VL-L2-anti-CD3 VH-CH1-C', and a second polypeptide comprising the structure: N'-anti-CD19 VH-L3-anti-CD19 VL-L4-anti-CD3 VL-CL-C'. In some embodiments, the CD3×CD19 MSAP (such as BSAP) comprises a first polypeptide comprising the structure: N'-anti-CD19 VH-L1-anti-CD19 VL-L2-anti-CD3 VH-CH1-C', and a second polypeptide comprising the structure: N'-anti-CD19 VL-L3-anti-CD19 VH-L4-anti-CD3 VL-CL-C'. In some embodiments, the CD3×CD19 MSAP (such as BSAP) comprises a first polypeptide comprising the structure: N'-anti-CD19 VL-L1-anti-CD19 VH-L2-anti-CD3 VH-CH1-C', and a second polypeptide comprising the structure: N'-anti-CD19 VL-L3-anti-CD19 VH-L4-anti-CD3 VL-CL-C'. L1, L2, L3, and L4 are any possible linkers (such as peptide liners) described herein. L1-L4 can be the same or different.

In some embodiments, the CD3×CD19 MSAP (such as BSAP) comprises a first polypeptide comprising the amino acid sequence of SEQ ID NO:53, or an amino acid sequence at least about 85% (such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%) identical to the sequence of SEQ ID NO:53. In some embodiments, the CD3×CD19 MSAP (such as BSAP) comprises a first polypeptide comprising the amino acid sequence of SEQ ID NO:60, or an amino acid sequence at least about 85% (such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%) identical to the sequence of SEQ ID NO:60. In some embodiments, the CD3×CD19 MSAP (such as BSAP) comprises a second polypeptide comprising the amino acid sequence of SEQ ID NO:54, or an amino acid sequence at least about 85% (such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%) identical to the sequence of SEQ ID NO:54. In some embodiments, the CD3×CD19 MSAP (such as BSAP) comprises a second polypeptide comprising the amino acid sequence of SEQ ID NO:61, or an amino acid sequence at least about 85% (such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%) identical to the sequence of SEQ ID NO:61. In some embodiments, the CD3×CD19 MSAP (such as BSAP) comprises a first polypeptide comprising the amino acid sequence of SEQ ID NO: 53 or 60, and a second polypeptide comprising the amino acid sequence of SEQ ID NO:54 or 61. In some embodiments, the CD3×CD19 MSAP (such as BSAP) comprises a first polypeptide comprising the amino acid sequence of SEQ ID NO:53, and a second polypeptide comprising the amino acid sequence of SEQ ID NO:54. In some embodiments, the first polypeptide is encoded by a nucleic acid comprising the sequence of SEQ ID NO:55. In some embodiments, the second polypeptide is encoded by a nucleic acid comprising the sequence of SEQ ID NO:56. In some embodiments, the CD3×CD19 MSAP (such as BSAP) comprises a first polypeptide comprising the amino acid sequence of SEQ ID NO:60, and a second polypeptide comprising the amino acid sequence of SEQ ID NO:61. In some embodiments, the CD3×CD19 MSAP (such as BSAP) comprises a first polypeptide comprising the amino acid sequence of SEQ ID NO:53, and a second polypeptide comprising the amino acid sequence of SEQ ID NO: 58. In some embodiments, the CD3×CD19 MSAP (such as BSAP) comprises a first polypeptide comprising the amino acid sequence of SEQ ID NO:60, and a second polypeptide comprising the amino acid sequence of SEQ ID NO:58. In some embodiments, the CD3×CD19 MSAP (such as BSAP) comprises a first polypeptide comprising the amino acid sequence of SEQ ID NO:57, and a second polypeptide comprising the amino acid sequence of SEQ ID NO: 54. In some embodiments, the CD3×CD19 MSAP (such as BSAP) comprises a first polypeptide comprising the amino acid sequence of SEQ ID NO:57, and a second polypeptide comprising the amino acid sequence of SEQ ID NO:61. Further provided are CD3×CD19 MSAPs (such as BSAPs) and compositions (such as pharmaceutical compositions) thereof comprising a first polypeptide comprising the amino acid sequence of SEQ ID NO:53, and a second polypeptide comprising the amino acid sequence of SEQ ID NO:54. Further provided are CD3×CD19 MSAPs (such as BSAPs) and compositions (such as pharmaceutical compositions) thereof comprising a first polypeptide comprising the amino acid sequence of SEQ ID NO:60, and a second polypeptide comprising the amino acid sequence of SEQ ID NO:61. Further provided are CD3×CD19 MSAPs (such as BSAPs)

and compositions (such as pharmaceutical compositions) thereof comprising a first polypeptide comprising the amino acid sequence of SEQ ID NO:53 or 60, and a second polypeptide comprising the amino acid sequence of SEQ ID NO: 58. Further provided are CD3×CD19 MSAPs (such as BSAPs) and compositions (such as pharmaceutical compositions) thereof comprising a first polypeptide comprising the amino acid sequence of SEQ ID NO:57, and a second polypeptide comprising the amino acid sequence of SEQ ID NO:54 or 61.

In some embodiments, the C-terminus of the first and/or second polypeptide of the CD3×CD19 MSAP (such as BSAP) comprises a covalent binding region CPPC (SEQ ID NO:45) or CPPCS (SEQ ID NO:46) capable of forming an intermolecular disulfide bond. For example, in some embodiments, the covalent binding region capable of forming an intermolecular disulfide bond is located at the C-terminus of CH1 and CL of the anti-CD3 Fab fragment. In some embodiments, the N-terminus or C-terminus of the first and/or the second polypeptide may comprise a histidine tag (HIS-tag) for protein purification. For example, in some embodiments, the N-terminus of the anti-CD19 antigen binding fragment (e.g., scFv) is additionally fused with a histidine tag. In some embodiments, the C-terminus of CH1 and/or CL of the anti-CD3 Fab fragment is additionally fused with a histidine tag. In some embodiments, the N-terminus of the first and/or the second polypeptide of the CD3×CD19 MSAP (such as BSAP) is additionally fused with a signal peptide for better expression, such as the signal peptide sequence set forth in SEQ ID NO:25, or a signal peptide encoded by a nucleic acid sequence of SEQ ID NO:26.

```
(amino acid sequence of a first polypeptide anti-CD19 VL - anti-CD19 VH -
GGGGS linker - anti-CD3 VH - CH1 - CPPCS; linkers are bolded, HVRs are underlined)
                                                                   SEQ ID NO: 53
DVVMTQSPSSIPVTLGESVSISCRSSKSLQNVNGNTYLYWFQQRPGQSPQLLIYRMSNLN

SGVPDRFSGSGSGTDFTLRISGVEPEDVGVYYCMQHLEYPLTFGAGTKLEIKGGGGSGG

GGSGGGGSQVQLVQSGPELIKPGGSVKMSCKASGYTFTSYVMHWVRQKPGQGLEWIG

YINPYNDGTKYNEKFKGRATLTSDKSSSTAYMELSSLRSEDSAVYYCARGTYYYGSRVF

DYWGQGTTVTVSSGGGGSEVQLVESGGGLVQPGGSLRLSCAASGFTFNTYAMNWVRQ

APGKGLEWVARIRSKYNNYATYYADSVKDRFTISRDDSKNTLYLQMNSLRAEDTAVYY

CVRHGNFGNSYVSWFAYWGQGTMVTVSSASTKGPSVFPLAPSSKSTSGGTAALGCLVK

DYFPEPVTVSWNSGALTSGVHTFPAVLQSSGLYSLSSVVTVPSSSLGTQTYICNVNHKPS

NTKVDKKVEPKSCPPCS (amino acid sequence of a second polypeptide anti-CD19 VL - anti-CD19 VH -
GGGGS linker - anti-CD3 VL - CL - CPPCS; linkers are bolded, HVRs are underlined)
                                                                   SEQ ID NO: 54
DVVMTQSPSSIPVTLGESVSISCRSSKSLQNVNGNTYLYWFQQRPGQSPQLLIYRMSNLN

SGVPDRFSGSGSGTDFTLRISGVEPEDVGVYYCMQHLEYPLTFGAGTKLEIKGGGGSGG

GGSGGGGSQVQLVQSGPELIKPGGSVKMSCKASGYTFTSYVMHWVRQKPGQGLEWIG

YINPYNDGTKYNEKFKGRATLTSDKSSSTAYMELSSLRSEDSAVYYCARGTYYYGSRVF

DYWGQGTTVTVSSGGGGSQAVVTQEPSLTVSPGGTVTLTCRSSTGAVTTSNYANWVQ

QKPGQAPRGLIGGTNKRAPGTPARFSGSLLGGKAALTLSGVQPEDEAEYYCALWYSNL

WVFGGGTKLTVLGQPKAAPSVTLFPPSSEELQANKATLVCLISDFYPGAVTVAWKADSS
```

PVKAGVETTTPSKQSNNKYAASSYLSLTPEQWKSHRSYSCQVTHEGSTVEKTVAPTE*CP*

*PCS*

(nucleic acid sequence encoding a first polypeptide anti-CD19 VL - anti-CD19
VH - GGGGS linker - anti-CD3 VH - CH1 - CPPCS)

SEQ ID NO: 55 gatgttgtgatgactcagtctcccagcagcatccccgtgaccctgggcgagtctgtgtccatcagctgcagaagcagcaagagcctgcaga acgtcaacggcaacacctacctgtactggttccagcagcggcctggccagtctcccagctgctgatctaccggatgagcaacctgaacag cggcgtgcccgatagattttctggctctggcagcggcaccgacttcaccctgagaatctccggcgtggaacccgaggacgtgggcgtgta ctactgtatgcagcacctggaataccccctgaccttcggagccggcaccaagctggagatcaaaggcggaggcggtagtggcggtggtg gttcaggcggtggcggatctcaggtgcagctggtgcagtctggccccgagctaatcaagcctggcggcagcgtgaagatgagctgcaag gcctccggctacaccttcaccagctacgtgatgcactgggtgcgccagaagcctggacagggcctggaatggatcggctacatcaacccc tacaacgatggcaccaagtacaacgagaagttcaagggcagagccaccctgaccagcgacaagagcagcagcaccgcctacatggaac tgagcagcctgcggagcgaggacagcgccgtgtactattgtgccagaggcacctactactacggcagccgggtgttcgactactgggga cagggcaccacggtcaccgtctcctcaggtggcggaggatctgaggtgcagctggtggagtctgggggaggcttggtacagcctgggg ggtccctgagactctcctgtgcagcctctggattcaccttttaacacctacgccatgaactgggtccgccaggctccagggaaggggctgga gtgggtcgcacgcataagaagtaaatataataattatgcaacatattatgccgattcagtgaaagaccggttcaccatctccagagacgattcc aagaacacgctgtatctgcaaatgaacagcctgagagccgaggacacggccgtatattactgtgtgagacatgggaacttcggtaatagct acgtttcctggtttgcttactggggccaagggacaatggtcaccgtctcttcagctagcaccaagggcccatccgtcttccccctggcaccct cctccaagagcacctctggggggcacagcggccctgggctgcctggtcaaggactacttccccgaaccggtgacggtgtcgtggaactca ggcgccctgaccagcggcgtgcacaccttcccggctgtcctacagtcctcaggactctactccctcagcagcgtggtgaccgtgccctcca gcagcttgggcacccagacctacatctgcaacgtgaatcacaagcccagcaacaccaaggtggacaagaaagttgagcccaaatcttgtc caccgtgctca*tag*

(nucleic acid sequence encoding a second polypeptide anti-CD19 VL - anti-
CD19 VH - GGGGS linker - anti-CD3 VL - CL - CPPCS)

SEQ ID NO: 56 gatgttgtgatgactcagtctcccagcagcatccccgtgaccctgggcgagtctgtgtccatcagctgcagaagcagcaagagcctgcaga acgtcaacggcaacacctacctgtactggttccagcagcggcctggccagtctcccagctgctgatctaccggatgagcaacctgaacag cggcgtgcccgatagattttctggctctggcagcggcaccgacttcaccctgagaatctccggcgtggaacccgaggacgtgggcgtgta ctactgtatgcagcacctggaataccccctgaccttcggagccggcaccaagctggagatcaaaggcggaggcggtagtggcggtggtg gttcaggcggtggcggatctcaggtgcagctggtgcagtctggccccgagctaatcaagcctggcggcagcgtgaagatgagctgcaag gcctccggctacaccttcaccagctacgtgatgcactgggtgcgccagaagcctggacagggcctggaatggatcggctacatcaacccc tacaacgatggcaccaagtacaacgagaagttcaagggcagagccaccctgaccagcgacaagagcagcagcaccgcctacatggaac tgagcagcctgcggagcgaggacagcgccgtgtactattgtgccagaggcacctactactacggcagccgggtgttcgactactgggga cagggcaccacggtcaccgtctcctcaggtggcggaggatctcaggctgtggtgactcaggagccctcactgactgtgtccccaggagg gacagtcactctcacctgtcgctcaagtactggggctgttacaactagtaactatgccaactgggtccagcagaaacctggacaagcaccca ggggtctgattggtggtaccaacaagcgagctccaggtaccctgcccggttctcaggctccctccttggggcaaagctgccctgacact gtcaggtgtgcagcctgaggacgaggctgagtattactgcgctctatggtacagcaacctctgggtgttcggcggagggaccaagctgac cgtcctaggccaaccgaaagcggcgccctcggtcactctgttcccgccctcctctgaggagcttcaagccaacaaggccacactggtgtgt ctcataagtgacttctacccgggagccgtgacagtggcctggaaggcagatagcagccccgtcaaggcgggagtggagaccaccacac cctccaaacaaagcaacaacaagtacgcggccagcagctatctgagcctgacgcctgagcagtggaagtcccacagaagctacagctgc caggtcacgcatgaagggagcaccgtggagaagacagtggcccctacagaatgtccaccgtgctca*tag*

-continued

```
(amino acid sequence of a first polypeptide anti-CD19 VL - anti-CD19 VH -
GGGGS linker - anti-CD3 VH - CH1 - CPPCS; linkers are bolded, HVRs are underlined)
                                                              SEQ ID NO: 60
DVVMTQSPSSIPVTLGESVSISCRSSKSLQNVNGNTYLYWFQQRPGQSPQLLIYRMSNLN

SGVPDRFSGSGSGTDFTLRISGVEPEDVGVYYCMQHLEYPITFGAGTKLEIKGGGGSGG

GGSGGGGSQVQLVQSGPELIKPGGSVKMSCKASGYTFTSYVMHWVRQKPGQGLEWIG

YINPYNDGTKYNEKFKGRATLTSDKSSSTAYMELSSLRSEDSAVYYCARGTYYYGSRVF

DYWGQGTTVTVSSGGGGSEVQLVESGGGLVQPGGSLRLSCAASGFTFNTYAMNWVRQ

APGKGLEWVARIRSKYNNYATYYADSVKDRFTISRDDSKNTLYLQMNSLRAEDTAVYY

CVRHGNFGNSYVSWFAYWGQGTMVTVSSASTKGPSVFPLAPSSKSTSGGTAALGCLVK

DYFPEPVTVSWNSGALTSGVHTFPAVLQSSGLYSLSSVVTVPSSSLGTQTYICNVNHKPS

NTKVDKKVEPKSCPPCS (amino acid sequence of a second polypeptide anti-CD19 VL - anti-CD19 VH -
GGGGS linker - anti-CD3 VL - CL - CPPCS; linkers are bolded, HVRs are underlined)
                                                              SEQ ID NO: 61
DVVMTQSPSSIPVTLGESVSISCRSSKSLQNVNGNTYLYWFQQRPGQSPQLLIYRMSNLN

SGVPDRFSGSGSGTDFTLRISGVEPEDVGVYYCMQHLEYPITFGAGTKLEIKGGGGSGG

GGSGGGGSQVQLVQSGPELIKPGGSVKMSCKASGYTFTSYVMHWVRQKPGQGLEWIG

YINPYNDGTKYNEKFKGRATLTSDKSSSTAYMELSSLRSEDSAVYYCARGTYYYGSRVF

DYWGQGTTVTVSSGGGGSQAVVTQEPSLTVSPGGTVTLTCRSSTGAVTTSNYANWVQ

QKPGQAPRGLIGGTNKRAPGTPARFSGSLLGGKAALTLSGVQPEDEAEYYCALWYSNL

WVFGGGTKLTVLGQPKAAPSVTLFPPSSEELQANKATLVCLISDFYPGAVTVAWKADSS

PVKAGVETTTPSKQSNNKYAASSYLSLTPEQWKSHRSYSCQVTHEGSTVEKTVAPTECP

PCS
```

III. Methods of Preparation

The CD3×CD19 MSAPs (such as BSAPs) described herein may be prepared by any of the known protein expression and purification methods in the art. For example, see Example 1. DNA sequence encoding the CD3×CD19 MSAP (such as BSAP) can be fully synthesized. After obtaining such sequence, it is cloned into a suitable expression vector, then transfected into a suitable host cell. The transfected host cells are cultured, and the supernatant is harvested and purified to obtain the CD3×CD19 MSAP (such as BSAP) of the present invention.

In some embodiments, the present application provides isolated nucleic acids encoding one or more of the polypeptides of any one of the CD3×CD19 MSAPs (such as BSAPs) described herein. In some embodiments, the isolated nucleic acid comprises the nucleic acid sequence of SEQ ID NO:55 or 56. The isolated nucleic acids may be DNA or RNA.

In some embodiments, the isolated nucleic acid is inserted into a vector, such as an expression vector, a viral vector, or a cloning vector. For expression of the nucleic acids, the vector may be introduced into a host cell to allow expression of the nucleic acids within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art. For example, the promoter sequences may be selected to promote the transcription of the polynucleotide in the vector. Suitable promoter sequences include, without limitation, T7 promoter, T3 promoter, SP6 promoter, beta-actin promoter. EF1a promoter, CMV promoter, and SV40 promoter. Enhancer sequences may be selected to enhance the transcription of the nucleic acids. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell. In some embodiments, the isolated nucleic acids further comprise a nucleic acid sequence encoding a signal peptide. In some embodiments, the signal peptide comprises the amino acid sequence of SEQ ID NO:25. In some embodiments, the nucleic acid sequence encoding the signal peptide comprises the nucleic acid sequence of SEQ ID NO:26.

SEQ ID NO:25 (amino acid sequence of signal peptide)
    MEWSWVFLFFLSVTTGVHS

SEQ ID NO:26 (nucleic acid encoding signal peptide)
    atggaatggagctgggtctttctcttcttcctgtcagtaacgactggtgtc-
    cactcc In some embodiments, there is provided an isolated host cell containing the vector described above. The host cells containing the vector may be useful in expression or cloning of the isolated nucleic acids. Suitable host cells can include, without limitation, prokaryotic cells, fungal cells, yeast cells, or higher eukaryotic cells such as mammalian cells. The expression of antibodies and antigen-binding fragments in prokaryotic cells such as *E. coli* is well established in the art. For a review, see for example Pluckthun, A. BioTechnology 9:545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4:573-576; Trill J. J. et al. (1995) Curr. Opinion Biotech 6:553-560. Higher eukaryotic cells, in particular, those derived from multicellular organisms can be used for expression of glycosylated polypeptides. Suitable higher eukaryotic cells include, without limitation, invertebrate cells and insect cells, and vertebrate cells.

The vector can be introduced to the host cell using any suitable methods known in the art, including, but not limited to, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In some embodiments, the host cells comprise a first vector encoding a first polypeptide and a second vector encoding a second polypeptide. In some embodiments, the host cells comprise a single vector comprising isolated nucleic acids encoding a first polypeptide and a second polypeptide.

In some embodiments, the present application provides methods of expressing any of the CD3×CD19 MSAPs (such as BSAPs) described herein, comprising culturing the isolated host cell containing the vector and recovering the CD3×CD19 MSAPs (such as BSAPs) from the cell culture. The isolated host cells are cultured under conditions that allow expression of the isolated nucleic acids inserted in the vectors. Suitable conditions for expression of polynucleotides may include, without limitation, suitable medium, suitable density of host cells in the culture medium, presence of necessary nutrients, presence of supplemental factors, suitable temperatures and humidity, and absence of microorganism contaminants. A person with ordinary skill in the art can select the suitable conditions as appropriate for the purpose of the expression.

In some embodiments, the polypeptides expressed in the host cell can form a dimer and thus produce a CD3×CD19 MSAP (such as BSAP) described herein. In some embodiments, the polypeptides expressed in the host cell can form a polypeptide complex which is a homodimer. In some embodiments, the host cells express a first polynucleotide and a second polynucleotide, the first polynucleotide and the second polynucleotide can form a polypeptide complex which is a heterodimer.

In some embodiments, the polypeptide complex (such as the CD3×CD19 MSAPs or BSAPs) may be formed inside the host cell. For example, the dimer may be formed inside the host cell with the aid of relevant enzymes and/or cofactors. In some embodiments, the polypeptide complex may be secreted out of the cell. In some embodiments, a first polypeptide and a second polypeptide may be secreted out of the host cell and form a dimer (such as the CD3×CD19 MSAPs or BSAPs) outside of the host cell.

In some embodiments, a first polypeptide and a second polypeptide may be separately expressed and allowed to dimerize to form the CD3×CD19 MSAP (such as BSAP) under suitable conditions. For example, the first polypeptide and the second polypeptide may be combined in a suitable buffer and allow the first protein monomer and the second protein monomer to dimerize through appropriate interactions such as hydrophobic interactions. In some embodiments, the first polypeptide and the second polypeptide may be combined in a suitable buffer containing an enzyme and/or a cofactor which can promote the dimerization of the first polypeptide and the second polypeptide. In some embodiments, the first polypeptide and the second polypeptide may be combined in a suitable vehicle and allow them to react with each other in the presence of a suitable reagent and/or catalyst.

The expressed polypeptide(s) and/or the polypeptide complex can be collected using any suitable methods. The polypeptide(s) and/or the polypeptide complex can be expressed intracellularly, in the periplasmic space or be secreted outside of the cell into the medium. If the polypeptide and/or the polypeptide complex are expressed intracellularly, the host cells containing the polypeptide and/or the polypeptide complex may be lysed and polypeptide and/or the polypeptide complex may be isolated from the lysate by removing the unwanted debris by centrifugation or ultrafiltration. If the polypeptide and/or the polypeptide complex is secreted into periplasmic space of E. coli, the cell paste may be thawed in the presence of agents such as sodium acetate (pH 3.5), EDTA, and phenylmethylsulfonylfluoride (PMSF) for about 30 min, and cell debris can be removed by centrifugation (Carter et al., BioTechnology 10:163-167 (1992)). If the polypeptide and/or the polypeptide complex is secreted into the medium, the supernatant of the cell culture may be collected and concentrated using a commercially available protein concentration filter, for example, an Amincon or Millipore Pellicon ultrafiltration unit. A protease inhibitor and/or an antibiotics may be included in the collection and concentration steps to inhibit protein degradation and/or growth of contaminated microorganisms.

The expressed polypeptide(s) and/or the polypeptide complex can be further purified by a suitable method, such as without limitation, affinity chromatography, hydroxylapatite chromatography, size exclusion chromatography, gel electrophoresis, dialysis, ion exchange fractionation on an ion-exchange column, ethanol precipitation, reverse phase HPLC, chromatography on silica, chromatography on heparin sepharose, chromatography on an anion or cation exchange resin (such as a polyaspartic acid column), chromatofocusing, SDS-PAGE, and ammonium sulfate precipitation (see, for review, Bonner, P. L., Protein purification, published by Taylor & Francis. 2007; Janson, J. C., et al, Protein purification: principles, high resolution methods and applications, published by Wiley-VCH, 1998).

In some embodiments, the polypeptides and/or polypeptide dimer complexes can be purified by affinity chromatography. In some embodiments, protein A chromatography or protein A/G (fusion protein of protein A and protein G) chromatography can be useful for purification of polypeptides and/or polypeptide complexes comprising a component derived from antibody CH2 domain and/or CH3 domain (Lindmark et al., J. Immunol. Meth. 62:1-13 (1983)); Zettlit, K. A., Antibody Engineering, Part V, 531-535, 2010). In some embodiments, protein G chromatography can be useful for purification of polypeptides and/or polypeptide complexes comprising IgG γ3 heavy chain (Guss et al., EMBO J. 5:1567 1575 (1986)). In some embodiments, protein L chromatography can be useful for purification of polypeptides and/or polypeptide complexes comprising k light chain (Sudhir, P., Antigen engineering protocols, Chapter 26, published by Humana Press, 1995; Nilson, B. H. K. at al, J. Biol. Chem., 267, 2234-2239 (1992)). The matrix to which the affinity ligand is attached is most often agarose, but other matrices are available.

Mechanically stable matrices such as controlled pore glass or poly(styrenedivinyl)benzene allow for faster flow rates and shorter processing times than can be achieved with agarose. Where the CD3×CD19 MSAP (such as BSAP) comprises an additional CH3 domain, the Bakerbond ABX resin (J. T. Baker, Phillipsburg, N.J.) is useful for purification.

IV. Pharmaceutical Compositions, Unit Dosages, Articles of Manufacture, and Kits Further provided by the present application are pharmaceutical compositions comprising any one of the CD3× CD19 MSAPs (such as BSAPs) described herein, and optionally a pharmaceutically acceptable carrier.

The pharmaceutical compositions may be suitable for a variety of modes of administration described herein, including for example systemic or localized administration. In some embodiments, the pharmaceutical composition is formulated for intravenous administration. In some embodiments, the pharmaceutical composition is formulated for subcutaneous administration. In some embodiments, the pharmaceutical composition is formulated for local administration to a tumor site. In some embodiments, the pharmaceutical composition is formulated for intratumoral injection.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such as glycerol.

The pharmaceutical compositions to be used for in vivo administration are generally formulated as sterile, substantially isotonic, and in full compliance with all Good Manufacturing Practice (GMP) regulations of the U.S. Food and Drug Administration. Sterility is readily accomplished by filtration through sterile filtration membranes. In some embodiments, the composition is free of pathogen. For injection, the pharmaceutical composition can be in the form of liquid solutions, for example in physiologically compatible buffers such as Hank's solution or Ringer's solution. In addition, the pharmaceutical composition can be in a solid form and re-dissolved or suspended immediately prior to use. Lyophilized compositions are also included.

In some embodiment, the pharmaceutical composition is formulated in accordance with routine procedures as a pharmaceutical composition adapted for injection intravenously, introperitoneally, or intravitreally. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In some embodiments, the pharmaceutical composition is suitable for administration to a human. In some embodiments, the pharmaceutical composition is suitable for administration to a rodent (e.g., mice, rats) or non-human primates (e.g., Cynomolgus monkey). In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

Also provided are unit dosage forms of the CD3×CD19 MSAPs (such as BSAPs) described herein, or compositions (such as pharmaceutical compositions) thereof. The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

The present application further provides articles of manufacture comprising the compositions (such as pharmaceutical compositions) described herein in suitable packaging. Suitable packaging for compositions (such as pharmaceutical compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present application also provides kits comprising compositions (such as pharmaceutical compositions) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

V. Methods of Treating Cancer

One aspect of the present application provides a method of treating a cancer (e.g., DLBCL or ALL) in an individual (such as a human), comprising administering to the individual an effective amount of any of the CD3×CD19 MSAPs (such as BSAPs) described herein, or a composition (such as pharmaceutical composition) thereof. In some embodiments, the CD3×CD19 MSAP (such as BSAP) or the composition (such as pharmaceutical composition) thereof is administered intravenously. In some embodiments, the method does not induce cytokine storm.

In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv). In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers are identical in sequence. In some embodiments, the first and the second linkers have different sequences. In some embodiments, the anti-CD3 Fab fragment specifically binds to the N-terminus of CD38 (e.g., an epitope within amino acids 1-27 of CD3E). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO: 2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 antigen binding fragment is an scFv. In some embodiments, the anti-CD19 antigen binding fragment is an scFv comprising the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the MSAP (such as BSAP) or the composition (such as pharmaceutical composition) thereof is administered intravenously. In some embodiments, the method does not induce cytokine storm. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the method of treating cancer described herein has one or more of the following biological activities: (1) killing cancer cells; (2) inhibiting proliferation of cancer cells; (3) inducing peripheral T cell redistribution (e.g., recruiting T cells to tissues or tumors that express CD19); (4) reducing tumor size; (5) alleviating one or more symptoms in an individual having cancer; (6) inhibiting tumor metastasis (e.g., metastasis to lymph nodes); (7) prolonging survival; (8) prolonging time to cancer progression; and (9) preventing, inhibiting, or reducing the likelihood of the recurrence of a cancer. In some embodiments, the method of killing cancer cells mediated by the CD3×CD19 MSAPs (such as BSAPs) described herein or pharmaceutical composition thereof can achieve a tumor cell death rate of at least about any of 40%, 50%, 60%, 70%, 80%, 90%, 95%, or more. In some embodiments, the method of reducing tumor size mediated by the CD3×CD19 MSAPs (such as BSAPs) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes) mediated by the CD3×CD19 MSAPs (such as BSAPs) described herein or pharmaceutical composition thereof can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the CD3×CD19 MSAPs (such as BSAPs) described herein or pharmaceutical composition thereof can prolongs the survival of the individual by at least any of 1, 2, 3, 4, 5, 6, 7, 8, 9, 10, 11, 12, 18, or 24 months, or more. In some embodiments, the method of prolonging time to cancer progression mediated by the CD3×CD19 MSAPs (such as BSAPs) described herein or pharmaceutical composition thereof can prolong the time to cancer progression by at least any of 1, 2, 3, 4, 5, 6, 7, 8, 9, 10, 11, or 12 weeks, or more. In some embodiments, the CD3×CD19 MSAPs (such as BSAPs) described herein or pharmaceutical composition thereof can increase, enhance, or stimulate an immune response or function in a subject by activating effector cells (e.g., T cells, e.g., CD8+ and/or CD4+ T cells). In some embodiments, the CD4 and/or CD8 T cells in the individual have increased or enhanced priming, activation, proliferation, cytokine release and/or cytolytic activity relative to prior to the administration of the CD3×CD19 MSAPs (such as BSAPs) described herein or pharmaceutical composition thereof.

In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO:14; II. an anti-CD19 antigen binding fragment (e.g., scFv) that specifically binds to CD19, wherein the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO:14; II. an anti-CD19 antigen binding fragment (e.g., scFv) that specifically binds to CD19, wherein the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO: 6 or 49; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO:10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; wherein the first and/or the second anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers are identical in sequence. In some embodiments, the first and the second linkers have different sequences. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises the amino acid sequence of SEQ ID NO:15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 antigen binding fragment is an scFv comprising the amino acid sequence of SEQ ID NO: 51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the MSAP (such as BSAP) or the composition (such as pharmaceutical composition) thereof is administered intravenously. In some embodiments, the method does not induce cytokine storm. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the method of treating cancer described herein has one or more of the following biological activities: (1) killing cancer cells; (2) inhibiting proliferation of cancer cells; (3) inducing peripheral T cell redistribution (e.g., recruiting T cells to tissues or tumors that express CD19); (4) reducing tumor size; (5) alleviating one or more symptoms in an individual having cancer; (6) inhibiting tumor metastasis (e.g., metastasis to lymph nodes); (7) prolonging survival; (8) prolonging time to cancer progression; and (9) preventing, inhibiting, or reducing the likelihood of the recurrence of a cancer. In some embodiments, the method of killing cancer cells mediated by the CD3×CD19 MSAPs (such as BSAPs) described herein or pharmaceutical composition thereof can achieve a tumor cell death rate of at least about any of 40%, 50%, 60%, 70%, 80%, 90%, 95%, or more. In some embodiments, the method of reducing tumor size mediated by the CD3×CD19 MSAPs (such as BSAPs) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes) mediated by the CD3×CD19 MSAPs (such as BSAPs) described herein or pharmaceutical composition thereof can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the CD3×CD19 MSAPs (such as BSAPs) described herein or pharmaceutical composition thereof can prolongs the survival of the individual by at least any of 1, 2, 3, 4, 5, 6, 7, 8, 9, 10, 11, 12, 18, or 24 months, or more. In some embodiments, the method of prolonging time to cancer progression mediated by the CD3×CD19 MSAPs (such as BSAPs) described herein or pharmaceutical composition thereof can prolong the time to cancer progression by at least any of 1, 2, 3, 4, 5, 6, 7, 8, 9, 10, 11, or 12 weeks, or more. In some embodiments, the CD3×CD19 MSAPs (such as BSAPs) described herein or pharmaceutical composition thereof can increase, enhance, or stimulate an immune response or function in a subject by activating effector cells (e.g., T cells, e.g., CD8+ and/or CD4+ T cells). In some embodiments, the CD4 and/or CD8 T cells in the individual have increased or enhanced priming, activation, proliferation, cytokine release and/or cytolytic activity relative to prior to the administration of the CD3×CD19 MSAPs (such as BSAPs) described herein or pharmaceutical composition thereof.

In some embodiments, the MSAP specifically binds to more than two (such as 3 or more) epitopes. For example, in some embodiments, the MSAP comprises a first anti-CD19 antigen binding fragment (e.g., scFv) fused to the N-terminus of the VH of the anti-CD3 Fab fragment, and a second anti-CD19 antigen binding fragment (e.g., scFv) fused to the N-terminus of the VL of the anti-CD3 Fab fragment, wherein the first and the second anti-CD19 antigen binding fragments (e.g., scFvs) bind to different CD19 epitopes. In some embodiments, the MSAP is a trispecific. In some embodiments, the MSAP is bispecific (e.g., a BSAP) and bivalent. For example, in some embodiments, the bivalent and bispecific MSAP (or BSAP) comprises one anti-CD19 antigen binding fragment (e.g., scFv) fused to the N-terminus of either VH or VL of the anti-CD3 Fab fragment. In some embodiments, the MSAP is bispecific (e.g., a BSAP)

and trivalent. For example, in some embodiments, the MSAP comprises a first anti-CD19 antigen binding fragment (e.g., scFv) fused to the N-terminus of the VH of the anti-CD3 Fab fragment, and a second anti-CD19 antigen binding fragment (e.g., scFv) fused to the N-terminus of the VL of the anti-CD3 Fab fragment, wherein the first and the second anti-CD19 antigen binding fragments (e.g., scFvs) bind to the same CD19 epitope. In some embodiments, the first and the second anti-CD19 antigen binding fragments (e.g., scFvs) have different amino acid sequences and/or structures but bind to the same CD19 epitope. In some embodiments, the first and the second anti-CD19 antigen binding fragments (e.g., scFvs) have the same amino acid sequence. In some embodiments, the anti-CD19 antigen binding fragment is an scFv. In some embodiments, the anti-CD19 antigen binding fragment is an scFv comprising the amino acid sequence of SEQ ID NO:51 or 59.

Thus in some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 scFv that specifically binds to CD19; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; wherein the CH1 and the CL of the anti-CD3 Fab fragment are connected by a disulfide bond; II. an anti-CD19 scFv that specifically binds to CD19; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the first and the second anti-CD19 scFvs have the same amino acid sequence, such as SEQ ID NO:51 or 59. In some embodiments, the first and the second anti-CD19 scFvs have different sequences. In some embodiments, the first and the second anti-CD19 scFvs bind to the same CD19 epitope. In some embodiments, the first and the second anti-CD19 scFvs bind to different CD19 epitopes. In some embodiments, the first and the second linkers are identical in sequence. In some embodiments, the first and the second linkers have different sequences. In some embodiments, the anti-CD3 Fab fragment specifically binds to the N-terminus of CD3δ (e.g., an epitope within amino acids 1-27 of CD3δ). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 scFv comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 scFv comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide and a second polypeptide, wherein the first polypeptide comprises the amino acid sequence of SEQ ID NO:53 or 60, and wherein the second polypeptide comprises the amino acid sequence of SEQ ID NO:54 or 61. In some embodiments, the MSAP (such as BSAP) comprises a first polypeptide and a second polypeptide, wherein the first polypeptide comprises the amino acid sequence of SEQ ID NO:53, and wherein the second polypeptide comprises the amino acid sequence of SEQ ID NO:54. In some embodiments, the MSAP (such as BSAP) comprises a first polypeptide and a second polypeptide, wherein the first polypeptide comprises the amino acid sequence of SEQ ID NO:60, and wherein the second polypeptide comprises the amino acid sequence of SEQ ID NO:61. In some embodiments, the MSAP (such as BSAP)

comprises a first polypeptide and a second polypeptide, wherein the first polypeptide comprises the amino acid sequence of SEQ ID NO:53 or 60, and wherein the second polypeptide comprises the amino acid sequence of SEQ ID NO:58. In some embodiments, the MSAP (such as BSAP) comprises a first polypeptide and a second polypeptide, wherein the first polypeptide comprises the amino acid sequence of SEQ ID NO:57, and wherein the second polypeptide comprises the amino acid sequence of SEQ ID NO:54 or 61. In some embodiments, the MSAP (such as BSAP) or the composition (such as pharmaceutical composition) thereof is administered intravenously. In some embodiments, the method does not induce cytokine storm. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the method of treating cancer described herein has one or more of the following biological activities: (1) killing cancer cells; (2) inhibiting proliferation of cancer cells; (3) inducing peripheral T cell redistribution (e.g., recruiting T cells to tissues or tumors that express CD19); (4) reducing tumor size; (5) alleviating one or more symptoms in an individual having cancer; (6) inhibiting tumor metastasis (e.g., metastasis to lymph nodes); (7) prolonging survival; (8) prolonging time to cancer progression; and (9) preventing, inhibiting, or reducing the likelihood of the recurrence of a cancer. In some embodiments, the method of killing cancer cells mediated by the CD3×CD19 MSAPs (such as BSAPs) described herein or pharmaceutical composition thereof can achieve a tumor cell death rate of at least about any of 40%, 50%, 60%, 70%, 80%, 90%, 95%, or more. In some embodiments, the method of reducing tumor size mediated by the CD3× CD19 MSAPs (such as BSAPs) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes) mediated by the CD3×CD19 MSAPs (such as BSAPs) described herein or pharmaceutical composition thereof can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the CD3×CD19 MSAPs (such as BSAPs) described herein or pharmaceutical composition thereof can prolongs the survival of the individual by at least any of 1, 2, 3, 4, 5, 6, 7, 8, 9, 10, 11, 12, 18, or 24 months, or more. In some embodiments, the method of prolonging time to cancer progression mediated by the CD3×CD19 MSAPs (such as BSAPs) described herein or pharmaceutical composition thereof can prolong the time to cancer progression by at least any of 1, 2, 3, 4, 5, 6, 7, 8, 9, 10, 11, or 12 weeks, or more. In some embodiments, the CD3×CD19 MSAPs (such as BSAPs) described herein or pharmaceutical composition thereof can increase, enhance, or stimulate an immune response or function in a subject by activating effector cells (e.g., T cells, e.g., CD8+ and/or CD4+ T cells). In some embodiments, the CD4 and/or CD8 T cells in the individual have increased or enhanced priming, activation, proliferation, cytokine release and/or cytolytic activity relative to prior to the administration of the CD3×CD19 MSAPs (such as BSAPs) described herein or pharmaceutical composition thereof.

In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO: 3; and/or a VL comprising: an HVR-L1 comprising the amino acid sequence of SEQ ID NO: 47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 scFv; wherein the anti-CD19 scFv is fused to the N-terminus of the VH of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO:12, an HVR-L2 comprising the amino acid sequence of SEQ ID NO: 13, and an HVR-L3 comprising the amino acid sequence of SEQ ID NO: 14; II. an anti-CD19 scFv that specifically binds to CD19, wherein the anti-CD19 scFv comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a linker connecting the anti-CD3 Fab fragment and the anti-CD19 scFv; wherein the anti-CD19 scFv is fused to the N-terminus of the VL of the anti-CD3 Fab fragment. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the first and/or the second anti-CD19 scFv comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the first and the second anti-CD19 scFvs have the same amino acid sequence. In some embodiments, the first and the second anti-CD19 scFvs have different sequences. In some embodiments, the first and the second anti-CD19 scFvs bind to the same CD19 epitope. In some embodiments, the first and the second anti-CD19 scFvs bind to different CD19 epitopes. In some embodiments, the first and the second linkers are identical in sequence. In some embodiments, the first and the second linkers have different sequences. In some embodiments, the anti-CD3 Fab fragment specifically binds to the N-terminus of CD3δ (e.g., an epitope within amino acids 1-27 of CD3E). In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO:18; and/or the CL of the anti-CD3 Fab fragment comprises the amino acid sequence of SEQ ID NO: 52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 scFv comprises a VH comprising the amino acid sequence of SEQ ID NO: 7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO: 54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the MSAP (such as BSAP) or the composition (such as pharmaceutical composition) thereof is administered intravenously. In some embodiments, the method does not induce cytokine storm. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the method of treating cancer described herein has one or more of the following biological activities: (1) killing cancer cells; (2) inhibiting proliferation of cancer cells; (3) inducing peripheral T cell redistribution (e.g., recruiting T cells to tissues or tumors that express CD19); (4) reducing tumor size; (5) alleviating one or more symptoms in an individual having cancer; (6) inhibiting tumor metastasis (e.g., metastasis to lymph nodes); (7) prolonging survival; (8) prolonging time to cancer progression; and (9) preventing, inhibiting, or reducing the likelihood of the recurrence of a cancer. In some embodiments, the method of killing cancer cells mediated by the CD3× CD19 MSAPs (such as BSAPs) described herein or pharmaceutical composition thereof can achieve a tumor cell death rate of at least about any of 40%, 50%, 60%, 70%, 80%, 90%, 95%, or more. In some embodiments, the method of reducing tumor size mediated by the CD3×CD19 MSAPs (such as BSAPs) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes) mediated by the CD3×CD19 MSAPs (such as BSAPs) described herein or pharmaceutical composition thereof can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the CD3×CD19 MSAPs (such as BSAPs) described herein or pharmaceutical composition thereof can prolongs the survival of the individual by at least any of 1, 2, 3, 4, 5, 6, 7, 8, 9, 10, 11, 12, 18, or 24 months, or more. In some embodiments, the method of prolonging time to cancer progression mediated by the CD3×CD19 MSAPs (such as BSAPs) described herein or pharmaceutical composition thereof can prolong the time to cancer progression by at least any of 1, 2, 3, 4, 5, 6, 7, 8, 9, 10, 11, or 12 weeks, or more. In some embodiments, the CD3×CD19 MSAPs (such as BSAPs) described herein or pharmaceutical composition thereof can increase, enhance, or stimulate an immune response or function in a subject by activating effector cells (e.g., T cells, e.g., CD8+ and/or CD4+ T cells). In some embodiments, the CD4 and/or CD8 T cells in the individual have increased or enhanced priming, activation, proliferation, cytokine release and/or cytolytic activity relative to prior to the administration of the CD3×CD19 MSAPs (such as BSAPs) described herein or pharmaceutical composition thereof.

In some embodiments, the MSAP (such as BSAP) comprises two anti-CD19 scFvs. In some embodiments, the two anti-CD19 scFvs both comprise the amino acid sequence of SEQ ID NO: 51 or 59.

Thus in some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; wherein the VH of the anti-CD3 Fab fragment comprises an HVR-H1 comprising the amino acid sequence of SEQ ID NO:9, an HVR-H2 comprising the amino acid sequence of SEQ ID NO:10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO: 14; II. a first anti-CD19 scFv and a second anti-CD19 scFv that specifically bind to CD19, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment; wherein the first and the second anti-CD19 scFvs both comprise amino acid sequence of SEQ ID NO:51 or 59; and III. optionally, a first linker connecting the VH of the anti-CD3 Fab fragment and the first anti-CD19 scFv, and a second linker connecting the VL of the anti-CD3 Fab fragment and the second anti-CD19 scFv. In some embodiments, the first and the second linkers are identical in sequence. In some embodiments, the first and the second linkers have different sequences. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO: 54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) or the composition (such as pharmaceutical composition) thereof is administered intravenously. In some embodiments, the method does not induce cytokine storm. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the method of treating cancer described herein has one or more of the following biological activities: (1) killing cancer cells; (2) inhibiting proliferation of cancer cells; (3) inducing peripheral T cell redistribution (e.g., recruiting T cells to tissues or tumors that express CD19); (4) reducing tumor size; (5) alleviating one or more symptoms in an individual having cancer; (6) inhibiting tumor metastasis (e.g., metastasis to lymph nodes); (7) prolonging survival; (8) prolonging time to cancer progression; and (9) preventing, inhibiting, or reducing the likelihood of the recurrence of a cancer. In some embodiments, the method of killing cancer cells mediated by the CD3×CD19 MSAPs (such as BSAPs) described herein or pharmaceutical composition thereof can achieve a tumor cell death rate of at least about any of 40%, 50%, 60%, 70%, 80%, 90%, 95%, or more. In some embodiments, the method of reducing tumor size mediated by the CD3× CD19 MSAPs (such as BSAPs) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes) mediated by the CD3×CD19 MSAPs (such as BSAPs) described herein or pharmaceutical composition thereof can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the CD3×CD19 MSAPs (such as BSAPs) described herein or pharmaceutical composition thereof can prolongs the survival of the individual by at least any of 1, 2, 3, 4, 5, 6, 7, 8, 9, 10, 11, 12, 18, or 24 months, or more. In some embodiments, the method of prolonging time to cancer progression mediated by the CD3×CD19 MSAPs (such as BSAPs) described herein or pharmaceutical composition thereof can prolong the time to cancer progression by at least any of 1, 2, 3, 4, 5, 6, 7, 8, 9, 10, 11, or 12 weeks, or more. In some embodiments, the CD3×CD19 MSAPs (such as BSAPs) described herein or pharmaceutical composition thereof can increase, enhance, or stimulate an immune response or function in a subject by activating effector cells (e.g., T cells, e.g., CD8+ and/or CD4+ T cells). In some embodiments, the CD4 and/or CD8 T cells in the individual have increased or enhanced priming, activation, proliferation, cytokine release and/or cytolytic activity relative to prior to the administration of the CD3×CD19 MSAPs (such as BSAPs) described herein or pharmaceutical composition thereof.

In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising a first polypeptide and a second polypeptide, wherein the first polypeptide comprises the amino acid sequence of SEQ ID NO:53 or 60, and the second polypeptide comprises the amino acid sequence of SEQ ID NO:54 or 61. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising a first polypeptide and a second polypeptide, wherein the first polypeptide comprises the amino acid sequence of SEQ ID NO:53, and the second polypeptide comprises the amino acid sequence of SEQ ID NO:54. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising a first polypeptide and a second polypeptide, wherein the first polypeptide comprises the amino acid sequence of SEQ ID NO:60, and the second polypeptide comprises the amino acid sequence of SEQ ID NO:61. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising a first polypeptide and a second polypeptide, wherein the first polypeptide comprises the amino acid sequence of SEQ ID NO:53 or 60, and the second polypeptide comprises the amino acid sequence of SEQ ID NO: 58. In some embodiments, there is provided a method of treating a cancer (e.g., DLBCL or ALL) in an individual (such as a human), comprising administering to the individual an effective amount of a MSAP (such as BSAP; or a pharmaceutical composition thereof) comprising a first polypeptide and a second polypeptide, wherein the first polypeptide comprises the amino acid sequence of SEQ ID NO:57, and the second polypeptide comprises the amino acid sequence of SEQ ID NO:54 or 61. In some embodiments, the MSAP (such as BSAP) or the composition (such as pharmaceutical composition) thereof is administered intravenously. In some embodiments, the method does not induce cytokine storm. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the method of treating cancer described herein has one or more of the following biological activities: (1) killing cancer cells; (2) inhibiting proliferation of cancer cells; (3) inducing peripheral T cell redistribution (e.g., recruiting T cells to tissues or tumors that express CD19); (4) reducing tumor size; (5) alleviating one or more symptoms in an individual having cancer; (6) inhibiting tumor metastasis (e.g., metastasis to lymph nodes); (7) prolonging survival; (8) prolonging time to cancer progression; and (9) preventing, inhibiting, or reducing the likelihood of the recurrence of a cancer. In some embodiments, the method of killing cancer cells mediated by the CD3×CD19 MSAPs (such as BSAPs) described herein or pharmaceutical composition thereof can achieve a tumor cell death rate of at least about any of 40%, 50%, 60%, 70%, 80%, 90%, 95%, or more. In some embodiments, the method of reducing tumor size mediated by the CD3×CD19 MSAPs (such as BSAPs) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes) mediated by the CD3×CD19 MSAPs (such as BSAPs) described herein or pharmaceutical composition thereof can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the CD3×CD19 MSAPs (such as BSAPs) described herein or pharmaceutical composition thereof can prolongs the survival of the individual by at least any of 1, 2, 3, 4, 5, 6, 7, 8, 9, 10, 11, 12, 18, or 24 months, or more. In some embodiments, the method of prolonging time to cancer progression mediated by the CD3×CD19 MSAPs (such as BSAPs) described herein or pharmaceutical composition thereof can prolong the time to cancer progression by at least any of 1, 2, 3, 4, 5, 6, 7, 8, 9, 10, 11, or 12 weeks, or more. In some embodiments, the CD3×CD19 MSAPs (such as BSAPs) described herein or pharmaceutical composition thereof can increase, enhance, or stimulate an immune response or function in a subject by activating effector cells (e.g., T cells, e.g., CD8+ and/or CD4+ T cells). In some embodiments, the CD4 and/or CD8 T cells in the individual have increased or enhanced priming, activation, proliferation, cytokine release and/or cytolytic activity relative to prior to the administration of the CD3×CD19 MSAPs (such as BSAPs) described herein or pharmaceutical composition thereof.

In some embodiments, there is provided a method of killing cancer cells (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a method of killing cancer cells (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of killing cancer cells (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the tumor cell death rate mediated by the MSAP (such as BSAP) is at least about any of 10%, 20%, 30%, 40%, 50%, 60%, 70%, 80%, 90%, 95%, or more. In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises an HVR-H1 comprising the amino acid sequence of SEQ ID NO: 9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO:12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO: 6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO: 54 or 61. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

In some embodiments, there is provided a method of inhibiting proliferation of cancer cells (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a method of inhibiting proliferation of cancer cells (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of inhibiting proliferation of cancer cells (e.g., DLBCL or ALL) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen binding fragment (e.g., scFv). In some the same amino acid sequence. In some embodiments, the first and the second anti-CD19 antigen binding fragments (e.g., scFvs) have different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the cancer cell proliferation rate is reduced by at least about any of 10%, 20%, 30%, 40%, 50%, 60%, 70%, 80%, 90%, 95%, or more in the present of MSAP (such as BSAP; or a pharmaceutical composition thereof). In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD3& (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO: 6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO: 54 or 61. In some embodiments, the cancer is selected from the group consisting of acute myeloid leukemia (AML), chronic myelogenous leukemia (CML) including blastic crisis of CML and Abelson onco-gene associated with CML (Bcr-ABL translocation), myelo-dysplastic syndrome (MDS), acute B lymphoblastic leuke-mia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid den-dritic cell neoplasm (BPDCN), non-Hodgkin lymphomas (NHL) including mantel cell leukemia (MCL) and small lymphocytic lymphoma (SLL), Hodgkin's lymphoma, sys-temic mastocytosis, and Burkitt's lymphoma.

In some embodiments, there is provided a method of inducing redistribution of peripheral T cells (e.g., recruiting T cells to tissues or tumors that express CD19) in an individual (such as a human), comprising administering to the individual an effective amount of a MSAP (such as BSAP; or a pharmaceutical composition thereof) compris-ing: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen bind-ing fragment (e.g., scFv) is fused to the N-terminus of the VH of the anti-CD3 Fab fragment. In some embodiments, there is a method of inducing redistribution of peripheral T cells (e.g., recruiting T cells to tissues or tumors that express CD19) in an individual (such as a human), comprising administering to the individual an effective amount of a MSAP (such as BSAP; or a pharmaceutical composition thereof) comprising: I. an anti-CD3 Fab fragment that spe-cifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of inducing redistribution of peripheral T cells (e.g., recruiting T cells to tissues or tumors that express CD19) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO: 45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO: 54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

In some embodiments, there is provided a method of reducing tumor size in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is a method of reducing tumor size in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of reducing tumor size in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the tumor size is reduced by at least about 10% (including for example at least about any of 20%, 30%, 40%, 60%, 70%, 80%, 90%, or 100%) in the presence of the MSAP (such as BSAP; or pharmaceutical composition thereof). In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO:16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO: 6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO: 54 or 61. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

In some embodiments, there is provided a method of alleviating one or more symptoms in an individual (such as a human) having cancer (e.g., DLBCL or ALL), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is a method of alleviating one or more symptoms in an individual (such as a human) having cancer (e.g., DLBCL or ALL), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of alleviating one or more symptoms in an individual (such as a human) having cancer (e.g., DLBCL or ALL), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO:13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO: 54 or 61. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

In some embodiments, there is provided a method of reducing (such as eradicating) pre-existing tumor metastasis (such as metastasis to the lymph node) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is a method of reducing (such as eradicating) pre-existing tumor metastasis (such as metastasis to the lymph node) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of reducing (such as eradicating) pre-existing tumor metastasis (such as metastasis to the lymph node) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, tumor metastasis (e.g., metastasis to lymph nodes) is reduced by at least about 10% (including for example at least about any of 20%, 30%, 40%, 60%, 70%, 80%, 90%, or 100%) in the presence of the MSAP (such as BSAP; or pharmaceutical composition thereof). In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO: 45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO: 54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

In some embodiments, there is provided a method of reducing incidence or burden of preexisting tumor metastasis (such as metastasis to the lymph node) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is a method of reducing incidence or burden of preexisting tumor metastasis (such as metastasis to the lymph node) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL;

optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of reducing incidence or burden of preexisting tumor metastasis (such as metastasis to the lymph node) in an individual (such as a human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO:18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO: 2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO: 54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

In some embodiments, there is provided a method of prolonging survival in an individual (such as a human) having cancer (e.g., DLBCL or ALL), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL;

optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is a method of prolonging survival in an individual (such as a human) having cancer (e.g., DLBCL or ALL), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of prolonging survival in an individual (such as a human) having cancer (e.g., DLBCL or ALL), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different amino acid sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the method prolongs the survival of the individual by at least any of 1, 2, 3, 4, 5, 6, 7, 8, 9, 10, 11, 12, 18, or 24 month. In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD3 (e.g., an epitope within amino acids 1-27 of CD3E). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO: 45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO:2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO: 54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the cancer is selected from the group consisting of acute myeloid leukemia (AML), chronic myelogenous leukemia (CML) including blastic crisis of CML and Abelson onco-gene associated with CML (Bcr-ABL translocation), myelodysplastic syndrome (MDS), acute B lymphoblastic leuke-mia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid den-dritic cell neoplasm (BPDCN), non-Hodgkin lymphomas (NHL) including mantel cell leukemia (MCL) and small lymphocytic lymphoma (SLL), Hodgkin's lymphoma, sys-temic mastocytosis, and Burkitt's lymphoma.

In some embodiments, there is provided a method of prolonging time to disease progression of cancer (e.g., DLBCL or ALL) in an individual (such as human), com-prising administering to the individual an effective amount of a MSAP (such as BSAP; or a pharmaceutical composition thereof) comprising: I. an anti-CD3 Fab fragment that spe-cifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is a method of prolonging time to disease progression of cancer (e.g., DLBCL or ALL) in an individual (such as human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding frag-ment (e.g., scFv) is fused to the N-terminus of the VL of the anti-CD3 Fab fragment. In some embodiments, there is provided a method of prolonging time to disease progression of cancer (e.g., DLBCL or ALL) in an individual (such as human), comprising administering to the individual an effective amount of a MSAP (such as BSAP; or a pharma-ceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen bind-ing fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VH of the anti-CD3 Fab fragment and the second anti-CD19 antigen bind-ing fragment (e.g., scFv). In some embodiments, the first and the second anti-CD19 antigen binding fragments (e.g., scFvs) have the same amino acid sequence. In some embodi-ments, the first and the second anti-CD19 antigen binding fragments (e.g., scFvs) have different amino acid sequences.

In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers have the same amino acid sequence. In some embodiments, the first and the second linkers have different amino acid sequence. In some embodiments, the method prolongs the time to disease progression by at least any of 1, 2, 3, 4, 5, 6, 7, 8, 9, 10, 11, or 12 weeks, or more. In some embodiments, the MSAP (such as BSAP; or pharmaceutical composition thereof) is administered intravenously. In some embodiments, the method does not induce cytokine storm. In some embodiments, the anti-CD3 Fab fragment specifically binds to the N-terminus of CD38 (e.g., an epitope within amino acids 1-27 of CD3E). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO: 11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO:14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO:18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO: 2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 scFv comprises the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO: 54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

The methods provided herein may be practiced in an adjuvant setting. In some embodiments, the method is practiced in a neoadjuvant setting, i.e., the method may be carried out before the primary/definitive therapy. In some embodiments, the method is used to treat an individual (such as human) who has previously been treated. Any of the methods of treatment provided herein may be used to treat an individual (such as human) who has not previously been treated. In some embodiments, the method is used as a first line therapy. In some embodiments, the method is used as a second line therapy.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radiofrequency ablation or the like, in an adjuvant setting or a neoadjuvant setting. In some embodiments, the cancer has been refractory to prior therapy.

Examples of solid cancers that may be treated by the methods of the invention include, but are not limited to, glioblastoma, non-small cell lung cancer, lung cancer other than non-small cell lung cancer, breast cancer, prostate cancer, pancreatic cancer, liver cancer, colon cancer, epithelial cancer, stomach cancer, spleen cancer, skin cancer, brain cancer other than glioblastoma, renal cancer, thyroid cancer, etc.

Examples of non-solid cancers that may be treated by the methods of the invention include, but are not limited to, acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the cancer is DLBCL or B-ALL.

In some embodiments, the method is suitable for treating cancers that overexpress CD19 on the surface of the cancer cells. In some embodiments, the cancer cells in the individual express at least about any of more than 2, 5, 10, 20, 50, 100, 200, 500, 1000 or more fold of CD19 compared to normal cells. In some embodiments, the CD19-positive cancer is a leukemia or lymphoma. In some embodiments, the CD19-positive cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

Thus, in some embodiments, there is provided a method of treating a CD19-positive cancer (such as leukemia or lymphoma) in an individual (such as human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VH of the anti-CD3 Fab fragment. In some embodiments, there is provided a method of treating a CD19-positive cancer (such as leukemia or lymphoma) in an individual (such as human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. an anti-CD19 antigen binding fragment (e.g., scFv) that specifically binds to CD19; and III. optionally, a linker connecting the anti-CD3 Fab fragment and the anti-CD19 antigen binding fragment (e.g., scFv); wherein the anti-CD19 antigen binding fragment (e.g., scFv) is fused to the N-terminus of the VL of the anti-CD3 Fab fragment. In some embodiments, there is provided a method of treating a CD19-positive cancer (such as leukemia or lymphoma) in an individual (such as human), comprising administering to the individual an effective amount of a MSAP (such as BSAP; or a pharmaceutical composition thereof) comprising: I. an anti-CD3 Fab fragment that specifically binds to CD3, wherein the anti-CD3 Fab fragment comprises: (a) an Ig VH and an Ig CH1; and (b) an Ig VL and an Ig CL; optionally wherein the CH1 and the CL of the anti-CD3 Fab fragment are connected by a disulfide bond; II. a first anti-CD19 antigen binding fragment (e.g., scFv) and a second anti-CD19 antigen binding fragment (e.g., scFv) that specifically bind to CD19, wherein the first anti-CD19 antigen binding fragment (e.g., scFv) is fused to the N-terminus of the VH of the anti-CD3 Fab fragment, and wherein the second anti-CD19 antigen binding fragment (e.g., scFv) is fused to the N-terminus of the VL of the anti-CD3 Fab fragment; and III. optionally, a first linker connecting the VH of the anti-CD3 Fab fragment and the first anti-CD19 antigen binding fragment (e.g., scFv), and a second linker connecting the VL of the anti-CD3 Fab fragment and the second anti-CD19 antigen binding fragment (e.g., scFv). In some embodiments, the first and the second anti-CD19 antigen binding fragments (e.g., scFvs) have the same amino acid sequence. In some embodiments, the first and the second anti-CD19 antigen binding fragments (e.g., scFvs) have different sequences. In some embodiments, the first and the second anti-CD19 antigen binding fragments (e.g., scFvs) bind to the same CD19 epitope. In some embodiments, the first and the second anti-CD19 antigen binding fragments (e.g., scFvs) bind to different CD19 epitopes. In some embodiments, the first and the second linkers are identical in sequence. In some embodiments, the first and the second linkers have different sequences. In some embodiments, the anti-CD3 Fab fragment specifically binds to the N-terminus of CD38 (e.g., an epitope within amino acids 1-27 of CD38). In some embodiments, the VH of the anti-CD3 Fab fragment comprises an HVR-H1 comprising the amino acid sequence of SEQ ID NO:9, an HVR-H2 comprising the amino acid sequence of SEQ ID NO: 10, and an HVR-H3 comprising the amino acid sequence of SEQ ID NO:11; and/or wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14. In some embodiments, the VH of the anti-CD3 Fab fragment comprises the amino acid sequence of SEQ ID NO: 15; and/or the VL of the anti-CD3 Fab fragment comprises the amino acid sequence of SEQ ID NO: 16. In some embodiments, the CH1 and the CL of the anti-CD3 Fab fragment are connected by about 1 to about 5 disulfide bonds (e.g., 2 disulfide bonds). In some embodiments, the CH1 of the anti-CD3 Fab fragment comprises the amino acid sequence of SEQ ID NO: 18; and/or the CL of the anti-CD3 Fab fragment comprises the amino acid sequence of SEQ ID NO:52. In some embodiments, the C-terminus of the CH1 and the CL of the anti-CD3 Fab fragment each further comprises a covalent binding sequence of CPPC (SEQ ID NO:45) or CPPCS (SEQ ID NO:46) capable of forming an intermolecular disulfide bond. In some embodiments, the anti-CD19 antigen binding fragment (e.g., scFv) comprises a VH comprising: an HVR-H1 comprising the amino acid sequence of SEQ ID NO:1, an HVR-H2 comprising the amino acid sequence of SEQ ID NO: 2, and an HVR-H3 comprising the amino acid sequence of SEQ ID NO:3; and/or a VL comprising: an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49. In some embodiments, the anti-CD19 antigen binding fragment (e.g., scFv) comprises a VH comprising the amino acid sequence of SEQ ID NO:7, and/or a VL comprising the amino acid sequence of SEQ ID NO:8 or 50. In some embodiments, the anti-CD19 antigen binding fragment is an scFv. In some embodiments, the anti-CD19 antigen binding fragment is an scFv comprising the amino acid sequence of SEQ ID NO:51 or 59. In some embodiments, the linker comprises about 2 to about 30 (e.g., about 2 to about 15) amino acid residues selected from the group consisting of glycine, serine, arginine, and alanine. In some embodiments, the linker is selected from the group consisting of SEQ ID NOs: 20-22, 29, and 31-44 (e.g., SEQ ID NO:44). In some embodiments, the MSAP (such as BSAP) comprises a first polypeptide comprising the amino acid sequence of SEQ ID NO:53 or 60, and a second polypeptide comprising the amino acid sequence of SEQ ID NO:54 or 61. In some embodiments, the MSAP (such as BSAP) comprises a first polypeptide comprising the amino acid sequence of SEQ ID NO:53, and a second polypeptide comprising the amino acid sequence of SEQ ID NO:54. In some embodiments, the MSAP (such as BSAP) comprises a first polypeptide comprising the amino acid sequence of SEQ ID NO:60, and a second polypeptide comprising the amino acid sequence of SEQ ID NO:61. In some embodiments, the MSAP (such as BSAP) comprises a first polypeptide comprising the amino acid sequence of SEQ ID NO:53 or 60, and a second polypeptide comprising the amino acid sequence of SEQ ID NO:58. In some embodiments, the MSAP (such as BSAP) comprises a first polypeptide comprising the amino acid sequence of SEQ ID NO:57, and a second polypeptide comprising the amino acid sequence of SEQ ID NO:54 or 61. In some embodiments, the MSAP (such as BSAP) or the composition (such as pharmaceutical composition) thereof is administered intravenously. In some embodiments, the method does not induce cytokine storm. In some embodiments, the CD19-positive cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma. In some embodiments, the method of treating CD19-positive cancer described herein has one or more of the following biological activities: (1) killing cancer cells; (2) inhibiting proliferation of cancer cells; (3) inducing peripheral T cell redistribution (e.g., recruiting T cells to tissues or tumors that express CD19); (4) reducing tumor size; (5) alleviating one or more symptoms in an individual having cancer; (6) inhibiting tumor metastasis (e.g., metastasis to lymph nodes); (7) prolonging survival; (8) prolonging time to cancer progression; and (9) preventing, inhibiting, or reducing the likelihood of the recurrence of a cancer. In some embodiments, the method of killing cancer cells mediated by the CD3× CD19 MSAPs (such as BSAPs) described herein or pharmaceutical composition thereof can achieve a tumor cell death rate of at least about any of 40%, 50%, 60%, 70%, 80%, 90%, 95%, or more. In some embodiments, the method of reducing tumor size mediated by the CD3×CD19 MSAPs (such as BSAPs) described herein or pharmaceutical composition thereof can reduce at least about 10% (including for example at least about any of 20%, 30%, 40%, 60%, 70%, 80%, 90%, or 100%) of the tumor size. In some embodiments, the method of inhibiting tumor metastasis (e.g., metastasis to lymph nodes) mediated by the CD3×CD19 MSAPs (such as BSAPs) described herein or pharmaceutical composition thereof can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the CD3×CD19 MSAPs (such as BSAPs) described herein or pharmaceutical composition thereof can prolongs the survival of the individual by at least any of 1, 2, 3, 4, 5, 6, 7, 8, 9, 10, 11, 12, 18, or 24 months, or more. In some embodiments, the method of prolonging time to cancer progression mediated by the CD3×CD19 MSAPs (such as BSAPs) described herein or pharmaceutical composition thereof can prolong the time to cancer progression by at least any of 1, 2, 3, 4, 5, 6, 7, 8, 9, 10, 11, or 12 weeks, or more. In some embodiments, the CD3×CD19 MSAPs (such as BSAPs) described herein or pharmaceutical composition thereof can increase, enhance, or stimulate an immune response or function in a subject by activating effector cells (e.g., T cells, e.g., CD8+ and/or CD4+ T cells). In some embodiments, the CD4 and/or CD8 T cells in the individual have increased or enhanced priming, activation, proliferation, cytokine release and/or cytolytic activity relative to prior to the administration of the CD3×CD19 MSAPs (such as BSAPs) described herein or pharmaceutical composition thereof.

Exemplary routes of administration of the CD3×CD19 MSAP (such as BSAP; or pharmaceutical composition thereof) described herein (or pharmaceutical composition thereof) include, but are not limited to, oral, intravenous, intracavitary, intratumoral, intraarterial, intramuscular, subcutaneous, parenteral, transmucosal, transdermal, ocular, topical, intraperitoneal, intracranial, intrapleural, and epidermal routes, or be delivered into lymph glands, body spaces, organs or tissues known to contain cancer cells. In some embodiments, the MSAP (such as BSAP; or pharmaceutical composition thereof) is administered intravenously. In some embodiments, the MSAP (such as BSAP; or pharmaceutical composition thereof) is administered by infusion. In some embodiments, the MSAP (such as BSAP; or pharmaceutical composition thereof) is administered subcutaneously. In some embodiments, the MSAP is administered by injection.

In some embodiments, the CD3×CD19 MSAP (such as BSAP; or pharmaceutical composition thereof) is administered by intravenous infusion. In some embodiments, the MSAP (such as BSAP; or pharmaceutical composition thereof) is infused to the individual over a period of time no more than about any of 24 hours, 20 hours, 15 hours, 10 hours, 8 hours, 6 hours, 3 hours, 2 hours, 1 hours, 30 minutes, or less. In some embodiments, the (such as BSAP) is infused to the individual over a period of time of any one of about 30 minutes to about 1 hour, about 1 hour to about 2 hours, about 2 hours to about 4 hours, about 4 hours to about 6 hours, about 6 hours to about 8 hours, about 8 hours to about 10 hours, about 10 hours to about 12 hours, about 12 hours to about 18 hours, about 18 hours to about 24 hours, about 30 minutes to about 2 hours, about 2 hours to about 5 hours, about 5 hours to about 10 hours, about 10 hours to about 20 hours, about 30 minutes to about 10 hours, or about 30 minutes to about 20 hours. The (such as BSAP) may be infused to the individual at any suitable rate. In some embodiments, the (such as BSAP) may be infused at a rate more than about any of 0.01 µg/kg/hr, 0.02 µg/kg/hr, 0.05 µg/kg/hr, 0.1 µg/kg/hr, 0.2 µg/kg/hr, 0.5 µg/kg/hr, 0.6 µg/kg/hr, 0.7 µg/kg/hr, 0.8 µg/kg/hr, 0.9 µg/kg/hr, 1 µg/kg/hr, 1.5 µg/kg/hr, 2 µg/kg/hr, 3 µg/kg/hr, 4 µg/kg/hr, 5 µg/kg/hr, 10

µg/kg/hr, 15 µg/kg/hr, 20 µg/kg/hr, 25 µg/kg/hr, 50 µg/kg/hr, 75 µg/kg/hr, 100 µg/kg/hr or more.

The dosing regimen of the CD3×CD19 MSAPs (such as BSAPs) administered to the individual (such as human) may vary with the particular MSAP (such as BSAP) composition (such as pharmaceutical composition), the method of administration, and the particular type and stage of cancer being treated. In some embodiments, that effective amount of the MSAP (such as BSAP; or pharmaceutical composition thereof) is below the level that induces a toxicological effect (i.e., an effect above a clinically acceptable level of toxicity) or is at a level where a potential side effect can be controlled or tolerated when the composition is administered to the individual.

In some embodiments, the effective amount of the CD3× CD19 MSAP (such as BSAP; or pharmaceutical composition thereof) is below the level that induces an adverse effect in the central nervous system. For example, an adverse effect observed in antibody therapy is the occurrence of infusion-related side effects, such as the cytokine release syndrome ("CRS"), the severe cases of which are known as "cytokine storms". When a "cytokine storm" is induced, the healthy individual's immune system is activated and releases large amounts of the pro-inflammatory cytokines, such as INF-γ, CCL2, IIL-10, IL-6, etc. It is a potentially fatal immune reaction typically consisting of a positive feedback loop between cytokines and immune cells, with highly elevated levels of various cytokines. Other adverse side effects described to be associated with CRS are fatigue, vomiting, tachycardia, hypertension, back pain, but also central nervous system reactions (CNS reactions), such as seizures, encephalopathy, cerebral edema, aseptic meningitis, and headache. In some embodiments, the CD3×CD19 MSAP (such as BSAP; or pharmaceutical composition thereof) is administered at a dose that does not induce cytokine release syndrome, such as cytokine storm. In some embodiments, the CD3×CD19 MSAP (such as BSAP; or pharmaceutical composition thereof) is administered at a dose that does not induce significant release of one or more cytokines selected from the group consisting of IL-2, IL-4, IL-5, IL-6, TNF, and INF-γ. In some embodiments, a significant release of a cytokine is sustained release of a cytokine over the course of at least about any of 1 hour, 2 hours, 4 hours, 6 hours, 8 hours, 10 hours, 12 hours, 18 hours, 24 hours, or more. In some embodiments, a significant release of a cytokine is a serum or blood level of a cytokine at a concentration of at least about any of 1, 5, 10, 20, 50, 100, 200, 500, 1000 or more pg/mL. Without being bound by any theory, the CD3×CD19 MSAPs (such as BSAPs) described herein (or pharmaceutical compositions thereof) require binding to CD19 on the target tumor cell in order to recruit and activate T cells. Such requirement can greatly reduce unwanted cytokine storms, and unwanted activation of T cells in the absence of the desired target tumor cell.

In some embodiments, the CD3×CD19 MSAP (such as BSAP; or pharmaceutical composition thereof) is administered at a dose of no more than about any one of 0.01 µg/kg, 0.05 µg/kg, 0.1 µg/kg, 0.5 µg/kg, 1 µg/kg, 2 µg/kg, 5 µg/kg, 10 µg/kg, 15 µg/kg, 20 µg/kg, 25 µg/kg, 30 µg/kg, 50 µg/kg, 100 µg/kg, 150 µg/kg, 200 µg/kg, 250 µg/kg, 300 µg/kg, 400 µg/kg, 500 µg/kg, 600 µg/kg, 700 µg/kg, 800 µg/kg, 900 µg/kg, or 1 mg/kg. The doses described herein may refer to a suitable dose for cynomolgus monkeys, a human equivalent dose thereof, or an equivalent dose for the specific species of the individual.

The effective amount of the CD3×CD19 MSAP (such as BSAP; or pharmaceutical composition thereof) may be administered in a single dose or in multiple doses. For methods that comprises administration of the MSAP (such as BSAP; or pharmaceutical composition thereof) in multiple doses, exemplary dosing frequencies include, but are not limited to, daily, daily without break, weekly, weekly without break, weekly for two out of three weeks, weekly for three out of four weeks, once every three weeks, once every two weeks, monthly, every six months, yearly, etc. In some embodiments, the CD3×CD19 MSAP (such as BSAP; or pharmaceutical composition thereof) is administered about once every 2 weeks, once every 3 weeks, once every 4 weeks, once every 6 weeks, or once every 8 weeks. In some embodiments, the CD3×CD19 MSAP (such as BSAP; or pharmaceutical composition thereof) is administered at least about any of 1×, 2×, 3×, 4×, 5×, 6×, or 7×(i.e., daily) a week. In some embodiments, the intervals between each administration are less than about any of 3 years, 2 years, 12 months, 11 months, 10 months, 9 months, 8 months, 7 months, 6 months, 5 months, 4 months, 3 months, 2 months, 1 month, 4 weeks, 3 weeks, 2 weeks, 1 week, 6 days, 5 days, 4 days, 3 days, 2 days, or 1 day. In some embodiments, the intervals between each administration are more than about any of 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 12 months, 2 years, or 3 years. In some embodiments, there is no break in the dosing schedule.

The administration of the CD3×CD19 MSAP (such as BSAP; or pharmaceutical composition thereof) can be extended over an extended period of time, such as from 1 day to about a week, from about a week to about a month, from about a month to about a year, from about a year to about several years. In some embodiments, the CD3×CD19 MSAP (such as BSAP; or pharmaceutical composition thereof) is administered over a period of at least any of about 1 day, 2 days, 3 days, 4 days, 5 days, 6 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 1 year, 2 years, 3 years, 4 years, or more.

Exemplary Embodiments

Embodiment 1. A multispecific antigen binding protein comprising:
I. an anti-CD3 Fab fragment that specifically binds to CD3, wherein the anti-CD3 Fab fragment comprises:
(a) an immunoglobulin (Ig) heavy chain variable region (VH) and an Ig heavy chain constant region (CH1); and
(b) an Ig light chain variable region (VL) and an Ig light chain constant region (CL);
Optionally wherein the CH1 and the CL of the anti-CD3 Fab fragment are connected by a disulfide bond;
II. an anti-CD19 antigen binding fragment that specifically binds to CD19; and
III. optionally, a linker connecting the anti-CD3 Fab fragment and the anti-CD19 antigen binding fragment.
Embodiment 2. The multispecific antigen binding protein of embodiment 1, wherein the anti-CD19 antigen binding fragment is fused to the N-terminus of the VH of the anti-CD3 Fab fragment.
Embodiment 3. The multispecific antigen binding protein of embodiment 1, wherein the anti-CD19 antigen binding fragment is fused to the N-terminus of the VL of the anti-CD3 Fab fragment.

Embodiment 4. The multispecific antigen binding protein of embodiment 1, comprising a first anti-CD19 antigen binding fragment and a second anti-CD19 antigen binding fragment, wherein the first anti-CD19 antigen binding fragment is fused to the N-terminus of the VH of the anti-CD3 Fab fragment, and wherein the second anti-CD19 antigen binding fragment is fused to the N-terminus of the VL of the anti-CD3 Fab fragment.

Embodiment 5. The multispecific antigen binding protein of any one of embodiments 1-4, wherein the anti-CD3 Fab fragment specifically binds to the N-terminus of CD3E.

Embodiment 6. The multispecific antigen binding protein of embodiment 5, wherein the anti-CD3 Fab fragment specifically binds to an epitope within amino acids 1-27 of CD38.

Embodiment 7. The multispecific antigen binding protein of embodiment 5 or 6, wherein the VH of the anti-CD3 Fab fragment comprises a heavy chain hypervariable region H1 (HVR-H1) comprising the amino acid sequence of SEQ ID NO:9, an HVR-H2 comprising the amino acid sequence of SEQ ID NO:10, and an HVR-H3 comprising the amino acid sequence of SEQ ID NO:11; and/or wherein the VL of the anti-CD3 Fab fragment comprises a light chain hypervariable region L1 (HVR-L1) comprising the amino acid sequence of SEQ ID NO: 12, an HVR-L2 comprising the amino acid sequence of SEQ ID NO:13, and an HVR-L3 comprising the amino acid sequence of SEQ ID NO:14.

Embodiment 8. The multispecific antigen binding protein of any one of embodiments 5-7, wherein the VH of the anti-CD3 Fab fragment comprises the amino acid sequence of SEQ ID NO: 15; and/or wherein the VL of the anti-CD3 Fab fragment comprises the amino acid sequence of SEQ ID NO:16.

Embodiment 9. The multispecific antigen binding protein of any one of embodiments 1-8, wherein the CH1 and the CL of the anti-CD3 Fab fragment are connected by about 1 to about 5 disulfide bonds.

Embodiment 10. The multispecific antigen binding protein of embodiment 9, wherein the CH1 and the CL of the anti-CD3 Fab fragment are connected by about 2 disulfide bonds.

Embodiment 11. The multispecific antigen binding protein of any one of embodiments 1-10, wherein the CH1 of the anti-CD3 Fab fragment comprises the amino acid sequence of SEQ ID NO: 18; and/or wherein the CL of the anti-CD3 Fab fragment comprises the amino acid sequence of SEQ ID NO:52.

Embodiment 12. The multispecific antigen binding protein of any one of embodiments 1-11, wherein the anti-CD19 antigen binding fragment comprises a VH, wherein the VH of the anti-CD19 antigen binding fragment comprises an HVR-H1 comprising the amino acid sequence of SEQ ID NO: 1, an HVR-H2 comprising the amino acid sequence of SEQ ID NO:2, and an HVR-H3 comprising the amino acid sequence of SEQ ID NO:3; and/or wherein the anti-CD19 antigen binding fragment comprises a VL, wherein the VL of the anti-CD19 antigen binding fragment comprises an HVR-L1 comprising the amino acid sequence of SEQ ID NO:47, an HVR-L2 comprising the amino acid sequence of SEQ ID NO:48, and an HVR-L3 comprising the amino acid sequence of SEQ ID NO:6 or 49.

Embodiment 13. The multispecific antigen binding protein of embodiment 12, wherein the VH of the anti-CD19 antigen binding fragment comprises the amino acid sequence of SEQ ID NO: 7; and/or wherein the VL of the anti-CD19 antigen binding fragment comprises the amino acid sequence of SEQ ID NO:8 or 50.

Embodiment 14. The multispecific antigen binding protein of any one of embodiments 1-13, wherein the anti-CD19 antigen binding fragment is a single chain variable fragment (scFv).

Embodiment 15. The multispecific antigen binding protein of embodiment 14, wherein the anti-CD19 scFv comprises the amino acid sequence of SEQ ID NO:51 or 59.

Embodiment 16. The multispecific antigen binding protein of embodiment 14 or 15, wherein the multispecific antigen binding protein comprises a first anti-CD19 scFv and a second anti-CD19 scFv.

Embodiment 17. The multispecific antigen binding protein of embodiment 16, wherein the first anti-CD19 scFv and the second anti-CD19 scFv have the same amino acid sequence.

Embodiment 18. The multispecific antigen binding protein of any one of embodiments 1-17, wherein the linker comprises about 2 to about 30 amino acid residues selected from the group consisting of glycine, serine, arginine, and alanine.

Embodiment 19. The multispecific antigen binding protein of embodiment 18, wherein the linker comprises about 2 to about 15 amino acid residues.

Embodiment 20. The multispecific antigen binding protein of embodiment 18 or 19, wherein the linker is selected from the group consisting of SEQ ID NOs: 20-22, 29, and 31-44.

Embodiment 21. The multispecific antigen binding protein of any one of embodiments 1-20, wherein the multispecific antigen binding protein comprises a first polypeptide and a second polypeptide, wherein the first polypeptide comprises the amino acid sequence of SEQ ID NO: 53 or 60, and wherein the second polypeptide comprises the amino acid sequence of SEQ ID NO: 54 or 61.

Embodiment 22. The multispecific antigen binding protein of embodiment 21, wherein the first polypeptide comprises the amino acid sequence of SEQ ID NO:53, and the second polypeptide comprises the amino acid sequence of SEQ ID NO:54.

Embodiment 23. The multispecific antigen binding protein of embodiment 21, wherein the first polypeptide comprises the amino acid sequence of SEQ ID NO:60, and the second polypeptide comprises the amino acid sequence of SEQ ID NO:61.

Embodiment 24. An isolated nucleic acid encoding the multispecific antigen binding protein of any one of embodiments 1-23.

Embodiment 25. A pharmaceutical composition comprising the multispecific antigen binding protein of any one of embodiments 1-23, and optionally a pharmaceutically acceptable carrier.

Embodiment 26. A method of treating a cancer in an individual in need thereof, comprising administering to the individual an effective amount of the pharmaceutical composition of embodiment 25.

Embodiment 27. The method of embodiment 26, wherein the pharmaceutical composition is administered intravenously.

Embodiment 28. The method of embodiment 26 or 27, wherein the individual is a human.

Embodiment 29. The method of any one of embodiments 26-28, wherein the cancer is selected from the group consisting of acute myeloid leukemia (AML), chronic myelogenous leukemia (CML) including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL) including Richter's syndrome or Richter's transformation of CLL, hairy cell leukemia (HCL), blastic plasmacytoid dendritic cell neoplasm (BPDCN), non-Hodgkin lymphomas (NHL) including mantel cell leukemia (MCL) and small lymphocytic lymphoma (SLL), Hodgkin's lymphoma, systemic mastocytosis, and Burkitt's lymphoma.

Embodiment 30. The method of embodiment 29, wherein the cancer is DLBCL or ALL.

EXAMPLES

The examples below are intended to be purely exemplary of the invention and should therefore not be considered to limit the invention in any way. The following examples and detailed description are offered by way of illustration and not by way of limitation. For the embodiments in which details of the experimental methods are not described, such methods are carried out according to conventional conditions such as those described in Sambrook et al. Molecular Cloning: A Laboratory Manual (New York: Cold Spring Harbor Laboratory Press, 1989), or as suggested by the manufacturers.

Example 1: Expression and Purification of Exemplary Multispecific Antigen Binding Proteins Multispecific antigen binding proteins (MSAPs) were expressed using standard protocols. DNA fragments encoding the first polypeptide chain and the second polypeptide chain of the MSAPs were cloned into pBOS based vector to generate constructs expressing the first polypeptide chain and the second polypeptide chain. The constructs also contained sequences encoding signal peptides in order to facilitate secretion of the first polypeptide chain and the second polypeptide chain proteins.

Amino acid sequences of exemplary CD19×CD3 MSAPs and nucleic acid sequences encoding thereof are shown in Table 1. FIG. 1A depicts the ITAB2009 MSAP conformation with an anti-CD3 scFv fused at the N-terminus the VH of an anti-CD19 Fab fragment. FIG. 1B depicts the ITAB2007 MSAP conformation with a first anti-CD19 scFv fused at the N-terminus of the VH of an anti-CD3 Fab fragment, and a second anti-CD19 scFv fused at the N-terminus of the VL of the anti-CD3 Fab fragment.

also contained Kozak sequences and sequences encoding signal peptides (amino acid sequence is shown as SEQ ID NO: 25, nucleic acid sequence is shown as SEQ ID NO:26) upstream of the first polypeptide chain and/or the second polypeptide chain, thereby producing a construct that expresses the first polypeptide chain and the second polypeptide chain of the ITAB2007 MSAP. CD19×CD3 MSAP ITAB2009 was constructed similarly. Sequencing results indicated correct gene insertion. The constructs were transformed into *E. coli* to obtain transfection-grade plasmid DNA. HEK293 cells were grown in EXPI293™ expression medium (Invitrogen). For transfection, 10 mL of medium containing plasmid DNA (DNA constructs encoding the first polypeptide and the second polypeptide of MSAP) and 25 kD Polyethylenimine (PEI; DNA/linear 25 kD PEI weight ratio of 1:3) was added to 90 mL of cell culture. Alternatively, about 30 µg DNA mixture ((DNA constructs encoding the first polypeptide and the second polypeptide of MSAP) was transfected into HEK293 cells using ExpiFectamine 293 transfection kit (Invitrogen) according to the manufacturer's instruction. Transfected cells were cultured in a CO₂ incubator (37° C., 5% CO₂, 125 rpm) for about 6 days, then the supernatant was collected.

The cell culture supernatant was purified with IgG-CH1 affinity chromatography (Thermo Fisher Scientific) to obtain target protein. The cell culture supernatant was filtered through a 0.22 µm sterile membrane, loaded onto the IgG-CH1 affinity matrix balanced with 150 mM NaCl and 10 mM phosphate buffered saline (PBS, pH 7.5), and eluted with 150 mM NaCl and 50 mM NaAc Buffer (pH 3.5). The eluate was adjusted with 2M Tris elution to a pH of 7.2, and concentrated with Vivaspin centrifugal concentrators having a 10 kD molecular weight cutoff (Sartorius). Purified protein was stored at 4° C.

Example 2: Determination of Binding Affinities of CD19×CD3 MSAPs

Antigen Binding Affinity

The binding affinity of the anti-CD19 and anti-CD3 binding domains in exemplary CD19×CD3 MSAPs (i.e., ITAB2007 and ITAB2009) with the corresponding human and cynomolgus monkey antigens were measured using Octet QK$^e$ with an anti-human IgG Fc Capture (AHC)

TABLE 1

Exemplary CD19 x CD3 MSAPs

| Protein code | Amino acid sequence of the first polypeptide chain | Amino acid sequence of the second polypeptide chain | Nucleic acid sequence encoding the first polypeptide chain | Nucleic acid sequence encoding the second polypeptide chain | Linker |
|---|---|---|---|---|---|
| ITAB2007 | SEQ ID NO: 53 | SEQ ID NO: 54 | SEQ ID NO: 55 | SEQ ID NO: 56 | SEQ ID NO: 44 (GGGGS) |
| ITAB2009 | SEQ ID NO: 23 | SEQ ID NO: 24 | SEQ ID NO: 28 | SEQ ID NO: 27 | SEQ ID NO: 21 (SGGGGS) |

Using CD19×CD3 MSAP ITAB2007 as an example, DNA fragment encoding the first polypeptide chain of ITAB2007 (nucleic acid sequence SEQ ID NO:55) and DNA fragment encoding the second polypeptide chain of ITAB2007 (nucleic acid sequence SEQ ID NO:56) were cloned into pBOS based vector, respectively. The construct biosensor. The human CD3 antigen construct (CD3εAA 1-27.Fc) and the cynomolgus CD3 antigen construct (cynoCD3εAA 1-27.Fc) had a peptide consisting of amino acids 1-27 of the CD3 epsilon fused to a human IgG Fc. The expression of the CD3 antigen constructs has been described in U.S. Pat. No. 8,846,042. The CD3 antigen constructs or the CD19 antigen (Cynomolgus/Rhesus CD19 Protein (Fc Tag), Sino Biological. Inc; Recombinant Human CD19 Fc Chimera, R&D Systems. Inc) were diluted to 0.02 mg/mL with dilution (PBS), and then immobilized on an anti-Human Fc capture (AHC) biosensor. ITAB2007 and ITAB2009 were diluted to various concentrations, and added to a black microplate. Control wells containing PBS only were also set up. The detection results were analyzed using ForteBio Data Acquisition and ForteBio Data Analysis software.

As shown in Table 2, the exemplary CD19×CD3 MSAPs (ITAB2007 or ITAB2009) exhibited cross-reactivity towards human and cynomolgus monkey antigens (CD19 or CD3) in vitro. The cross-reactivity of the MSAPs can facilitate extrapolation of toxicity and efficacy study results from cynomolgus monkeys to human clinical studies.

TABLE 2

| In vitro binding affinities (KD) | | |
|---|---|---|
| Antigen | ITAB2007 | ITAB2009 |
| huCD19.Fc | $8.91 \times 10^{-10}$M | $1.82 \times 10^{-8}$M |
| cynoCD19.Fc | $8.91 \times 10^{-9}$M | $2.96 \times 10^{-8}$M |
| CD3ε&AA 1-27.Fc | $5.99 \times 10^{-9}$M | $35 \times 10^{-8}$M |
| cyno CD3εAA 1-27.Fc | $1.88 \times 10^{-8}$M | $1.29 \times 10^{-8}$M |

Example 3: CD19×CD3 MSAP Mediated PBMC Cytotoxicity Against Autologous B Cells Human PBMC (hPBMC) Preparation: White blood cell concentrate samples from healthy human adults were diluted with PBS buffer (Gibco), centrifuged by density gradient centrifugation (Ficoll-Paque, GE Healthcare) to obtain PBMC, washed twice with PBS, then centrifuged at room temperature, 1000 g for 10 min. Cells were collected, and resuspended in RPMI 1640 Medium (Gibco) containing 10% FBS.

200 μL of $3 \times 10^5$ PBMCs per well were added to a 96-well plate. CD19×CD3 MSAPs ITAB2007 and ITAB2009 diluted to various concentrations were then added according to experimental design. Wells containing PBMCs without adding CD19×CD3 MSAPs were set up as controls. The mixture was incubated at 37° C., 5% $CO_2$ for about 18-24 hours. Cells were harvested and incubated with antibody FITC Mouse Anti-Human CD20 (BD Pharmingen™) for 30 minutes at room temperature. Propidium iodide (Sigma) was added at 2 μg/mL and stained for 15 minutes. Analysis was performed using ACCURI C6 (BD Bioscience).

Propidium iodide (PI) is a commonly used nuclear fluorescent dye. PI cannot penetrate intact cell membranes, and cannot stain live cells with intact cell membranes. Due to the loss of membrane integrity of dead cells, PI can enter dead cells to bind DNA. Thus PI staining can be used to identify dead cells. CD20-positive is indicative of viable B cells, while cells positive for both CD20 and PI represent dead B cells. CD19×CD3 MSAP-mediated cytotoxicity was calculated using the following formula: % death rate=[1−(sample well alive B cells/sample well total B cells)/(control well alive B cells/control well total B cells)]×100%.

Death rate was set as the y-axis, and MSAP concentration was set as the x-axis. The curves were fitted using a 4-parameter logistic model to determine EC50.

Figure 2:
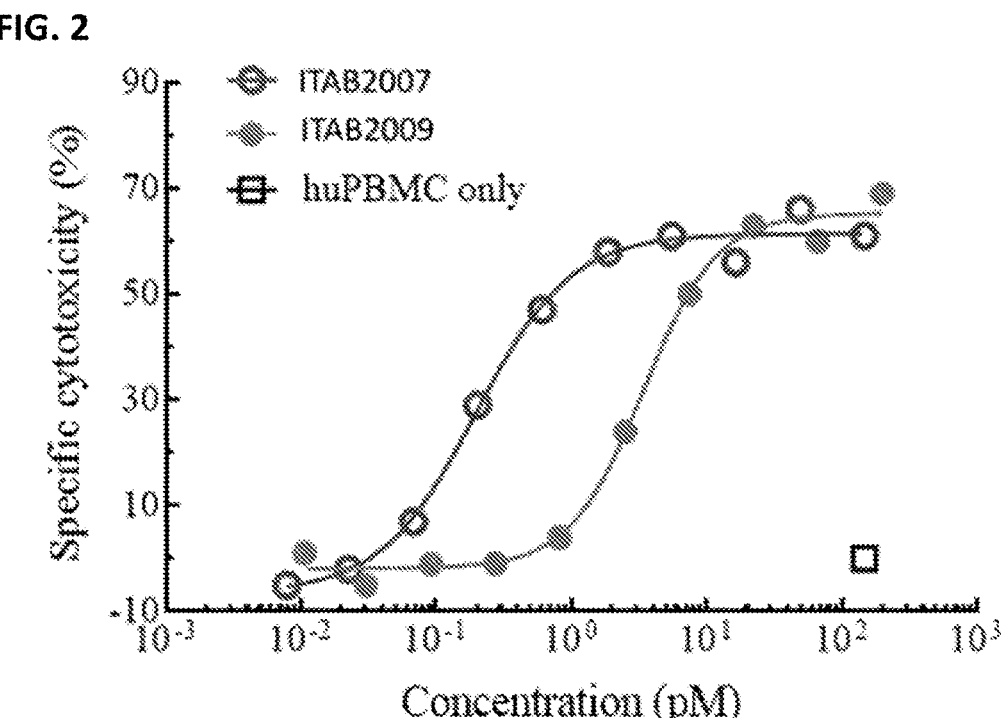
FIG. 2 depicts CD19×CD3 MSAP (ITAB2009 or ITAB2007) mediated human PBMC cytotoxicity against autologous B cells. B cells mixed with human PBMC only without adding CD19×CD3 MSAP served as control.

As can be seen from FIG. 2, both CD19×CD3 ITAB2007 and ITAB2009 MSAPs were able to mediate autologous B cell killing by human PBMCs, with EC50 of about 0.16 pM and 2.4 pM, respectively. ITAB2007 CD19×CD3 MSAP is superior to ITAB2009 in killing autologous B cells.

Example 4: CD19×CD3 MSAP Mediated PBMC Cytotoxicity Against Tumor Cells (Cytotoxicity Assays)

Human PBMC were prepared according to the method described in Example 3, and resuspended in RPMI 1640 Medium (Gibco) containing 10% FBS (Gibco).

Daudi cells (target cells) were washed and centrifuged, stained by DiOC18 (3,3'-Dioctadecyloxacarbocyanine perchlorate, Life technologies) for 15 minutes, then resuspended in RPMI 1640 Medium containing 10% FBS (Gibco). 100 μL $3 \times 10^4$ Daudi cells and 100 μL $3 \times 10^5$ PBMC were added to each well of a 96-well plate. CD19×CD3 MSAPs (e.g., ITAB2007, ITAB2009) were diluted to various concentrations according to experimental design and added to the cell mixture. Wells with no MSAP added (PBMC+Daudi target cells) were set up as controls. About 48 hr incubation was carried out at 37° C. with 5% $CO_2$. DiOC18 non-stained control wells were set up. Cells were stained by propidium iodide (PI, Sigma) to represent dead cells. ACCURI C6 Cytometer (BD Bioscience) was used for analysis.

DiOC18-positive cells represent alive Daudi cells, while cells positive for both DiOC18 and PI represent dead Daudi cells. CD19×CD3 MSAP-mediated cytotoxicity was calculated using the below formula: % death rate=[1−(sample well alive B cells/sample well total B cells)/(control well alive B cells/control well total B cells)]×100%.

Death rate was set as the y-axis, and MSAP concentration was set as the x-axis. The curves were fitted using a 4-parameter logistic model to determine EC50.

Figure 3:
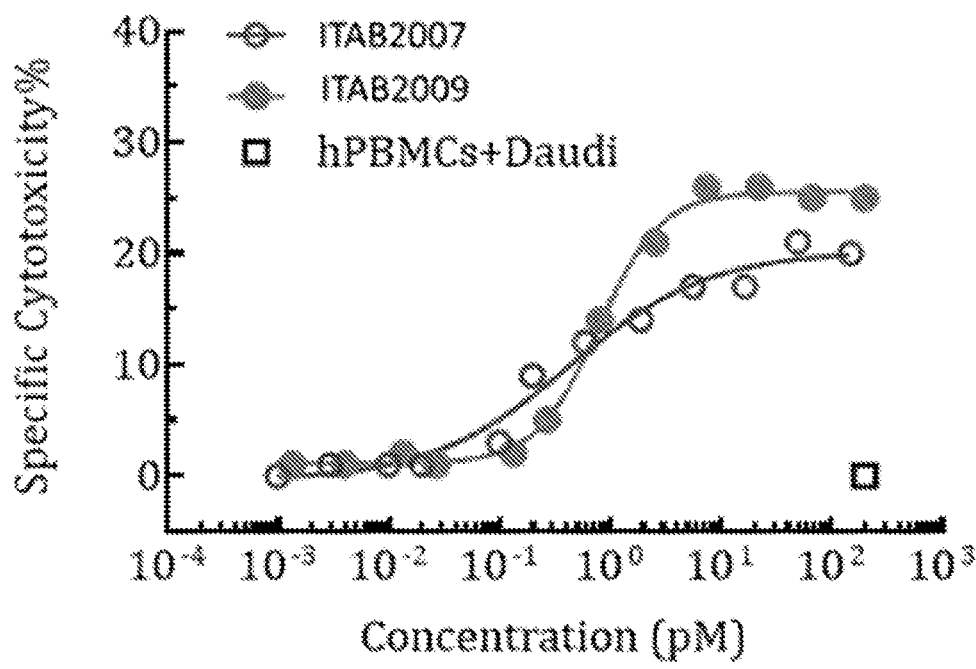
FIG. 3 depicts CD19×CD3 MSAP (ITAB2009 or ITAB2007) mediated human PBMC cytotoxicity against Daudi tumor cells. Daudi tumor cells mixed with human PBMC only without adding CD19×CD3 MSAP served as control.

As can be seen from FIG. 3, CD19×CD3 MSAP ITAB2007 and ITAB2009 were both effective in mediating human PBMC to kill tumor cells such as Daudi.

Example 5: Tumor-Dependent Activation of Human Pri-T Cells by an CD19×CD3 MSAP CD8 is a typical T cell surface antigen. CD69 is a cell surface receptor, which is upregulated upon T cell activation. The percentage of the $CD69^+CD8^+$ subtype can serve as an effective indicator of the activation status of T cells. FACS-based T cell activation assays were performed to determine the ability of exemplary CD19×CD3 MSAP (i.e., ITAB2009 and ITAB2007) in T cell activation.

Figure 4:
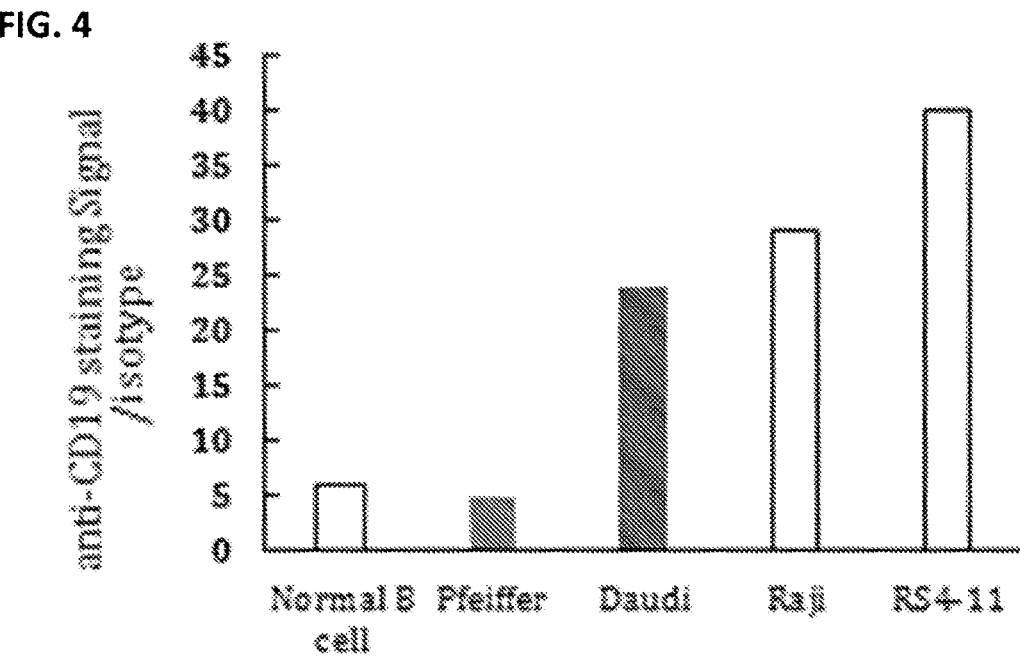
FIG. 4 depicts CD19 expression level of different cells, as reflected by anti-CD19 staining signal.

Pfeiffer (diffuse large B cell lymphoma) and Daudi (Burkitt's lymphoma), two B lymphoma cell lines with different CD19 expression levels (FIG. 4) were studied in ITAB2009- or ITAB2007-mediated human T cell activation (CD69+ CD8+ T cell ratio over total CD8+ T cells).

Preparation of Pri-T cells: Human PBMC were prepared according to the method described in Example 3, and resuspended in RPMI 1640 Medium (Gibco) containing 10% FBS (Gibco). PBMCs were inoculated into culture flasks coated with Mouse IgG2a anti-human CD3 antibodies (5 μg/mL; BioLegend, Inc.) and Mouse IgG1 anti-human CD28 antibodies (1 μg/mL; BioLegend, Inc.), and cultured for 3 days in a 37° C., 5% $CO_2$ incubator. Cells were treated with IL-2 for another 3 days, then collected for future experiments. These cells were named as Pri-T.

Figure 5A:
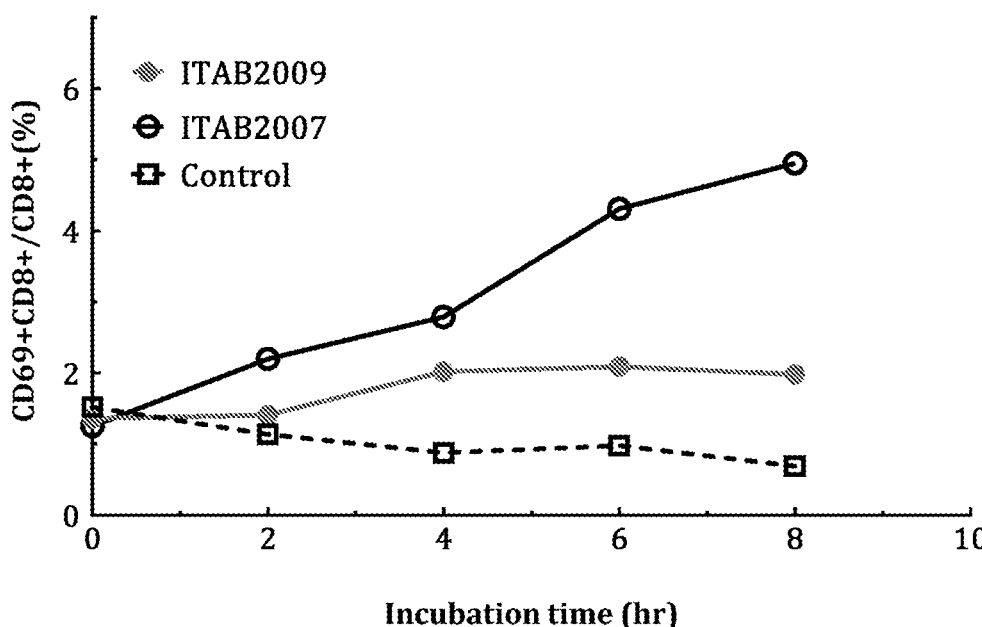
FIGS. 5A-5B depict CD19×CD3 MSAP (ITAB2009 or ITAB2007) mediated T cell activation in the presence of Pfeiffer cells (FIG. 5A) or Daudi cells (FIG. 5B). T cells mixed with Pfeiffer cells or Daudi cells without the addition of CD19×CD3 MSAP served as controls.
Figure 5B:
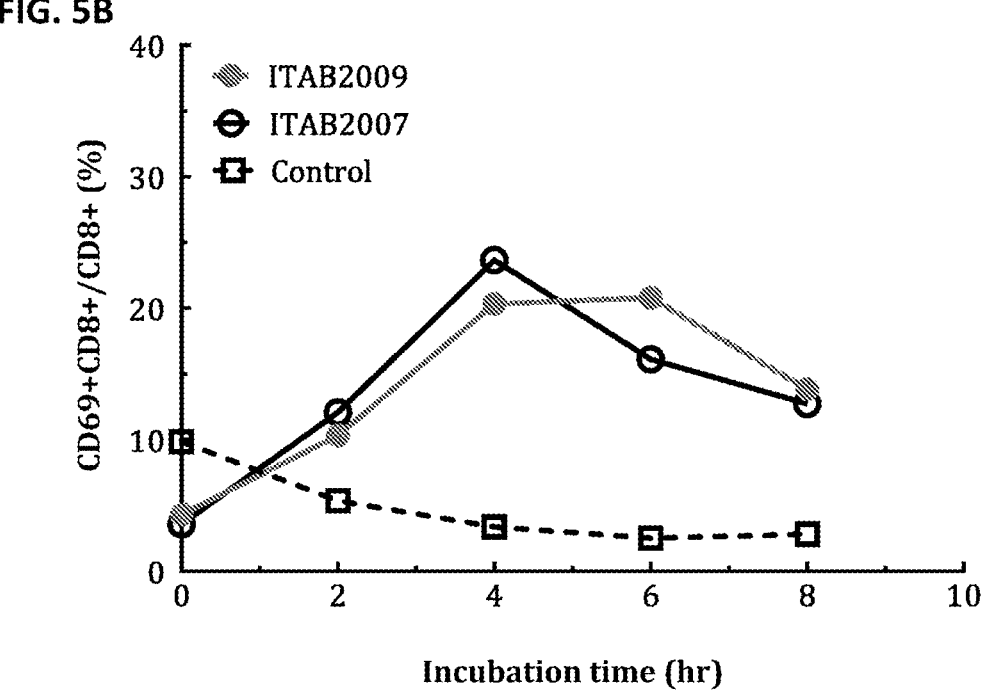

Pri-T ($3 \times 10^4$ cells/100 μL) and Daudi or Pfeiffer cells ($3 \times 10^4$ cells/100 μL) were mixed gently, then ITAB2009 or ITAB2007 CD19×CD3 MSAP were added and incubated for different incubation time. Cells were then collected for staining with FITC Mouse Anti-Human CD69 antibody (BD Pharmingen™) and CD8 antibody (3B5) RPE conjugate (Invitrogen) for 30 minutes, and flow cytometer was used for analysis. Samples were analyzed using ACCURIR C6 Cytometer (BD Biosciences). Results are shown in FIGS. 5A-5B. Data were presented by calculating CD69+ percentage over CD8+.

As shown in FIGS. 5A-5B, under the same conditions, ITAB2007 CD19×CD3 MSAP induced T cell activation more effectively than ITAB2009 for Pfeiffer cells, the diffuse large B cell lymphoma (DLBCL) cell line with low CD19 expression (FIG. 5A, FIG. 4); while for Daudi, the lymphoma cell line with high CD19 expression (FIG. 4), ITAB2007 and ITAB2009 CD19×CD3 MSAPs showed similar T cell activation effect (FIG. 5B). These results indicate that the bispecific trivalent ITAB2007 CD19×CD3 MSAP have the potential of targeting low CD19-expressing tumor cells.

Example 6: CD19×CD3 MSAP Mediated Human Pri-T Cell Cytotoxicity Against Tumor Cells (Cytotoxicity Assays)

Pri-T cells were prepared according to the method described in Example 5, and resuspended in RPMI 1640 Medium (Gibco) containing 10% FBS (Gibco).

Reh cells (acute lymphocytic leukemia) were washed and centrifuged, stained by CFSE (5-(and 6)-Carboxyfluorescein diacetate succinimidyl ester, eBioscience) for 10 minutes, then resuspended in RPMI 1640 Medium (Gibco) containing 10% FBS (Gibco). 100 µL $1 \times 10^4$ Reh cells and 100 µL $4 \times 10^4$ Pri-T cells were added to each well of a 96-well plate. CD19×CD3 MSAPs (e.g., ITAB2007, ITAB2009) were diluted to various concentrations according to experimental design and added to the cell mixture. Wells with no MSAP added (Pri-T+Reh target cells) were set up as controls. About 24 hr incubation was carried out at 37° C. with 5% $CO_2$. Cells were stained by 7-AAD (7-Amino-Actinomycin, BD) for 10 min. Cytoflex S (Beckman) was used for analysis.

CFSE-positive cells represent Reh cells, while cells positive for 7-AAD represent dead cells. CD19×CD3 MSAP-mediated cytotoxicity was calculated using the below formula: % death rate=[1−(sample well alive B cells/sample well total alive cells)/(control well alive B cells/control well total alive cells)]×100%.

Death rate was set as the y-axis, and MSAP concentration was set as the x-axis. The curves were fitted using a 4-parameter logistic model to determine EC50.

Figure 6:
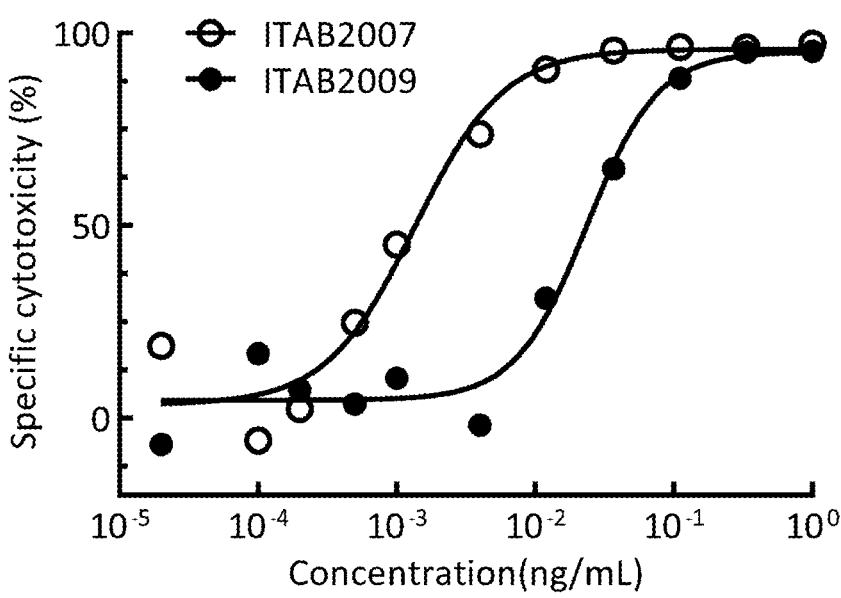
FIG. 6 depicts CD19×CD3 MSAP (ITAB2009 or ITAB2007) mediated human Pri-T cells cytotoxicity against Reh cells.

As shown in FIG. 6, CD19×CD3 MSAP ITAB2007 showed significantly better effectiveness compared to ITAB2009 in mediating human Pri-T cells to kill tumor cells such as Reh cells.

Example 7: Efficacy Assay of an CD19×CD3 MSAP in Killing Human Burkitt's Lymphoma Tumor Xenograft in an Immune-Reconstructed Mouse Model To examine the effect of an exemplary CD19×CD3 MSAP (i.e., ITAB2007) on inhibiting the growth of human burkitt's lymphoma tumor xenograft, in vivo drug efficacy assays were carried out on immunodeficient mice having immune system reconstructed with human lymphocytes and implanted with Raji tumor cells.

For cancer cell inoculation, Raji burkitt's lymphoma cell line was cultured in vitro and collected, resuspended with serum-free L-15 Medium (Gibco) pre-cooled on ice, and placed on ice for later use. For human PBMC reconstitution, white cell concentrate donated by healthy human donors was collected, centrifuged by density gradient centrifugation (Ficoll-Paque, GE Healthcare) to obtain PBMC, resuspended in RPMI 1640 Medium (Gibco) pre-cooled on ice, and placed on ice for later use.

Seven to eight weeks old female NOG mice (NOD.Cg-Prkdc$^{scid}$II2rg$^{Tm/Sug}$/JicCrl) were raised under SPF conditions (AAALAC accredited) at least one week before the study began. Mice were treated with Busulfan (Sigma) intraperitoneally at the concentration of 25 mg/kg per day for two days (day −4 and day −3), then subcutaneously inoculated with $2.0 \times 10^6$ cells/mouse of Raji cells in the right dorsal flank of the mice in a volume of 0.2 mL/mouse on day 0, followed with reconstitution using $4.0 \times 10^6$ cells/mouse of unstimulated human PBMCs from one healthy donor intraperitoneally in a volume of 0.2 mL/mouse on day 3.

Thirty-two tumor bearing mice were randomized into 4 groups for CD19×CD3 MSAP treatment (eight mice per group) on day 14 when Raji tumors grew to around 100-300 mm$^3$, and treated intraperitoneally daily with vehicle (PBST, control), ITAB2007 at 0.5 µg/kg, ITAB2007 at 5 µg/kg, or ITAB2007 at 50 µg/kg, respectively. The length and width of each tumor were measured using a caliper twice a week after randomization. Individual tumor volume was calculated based on the following formula: tumor volume (mm$^3$)= length (mm)×width (mm)×width (mm)×0.5. Tumor growth inhibition rate (TGI %) was used to evaluate drug efficacy. TGI %=[1−(avT$_i$−avT$_0$)/(avC$_i$−avC$_0$)]×100, wherein avT$_i$− avT$_0$ is the average tumor volume on day i minus the average tumor volume on the day of treatment initiation (i.e. day 14) for the treatment group, and avCi−0 is the average tumor volume on day i minus the average tumor volume on the day of treatment initiation (i.e. day 14) for the vehicle control group.

Figure 7:
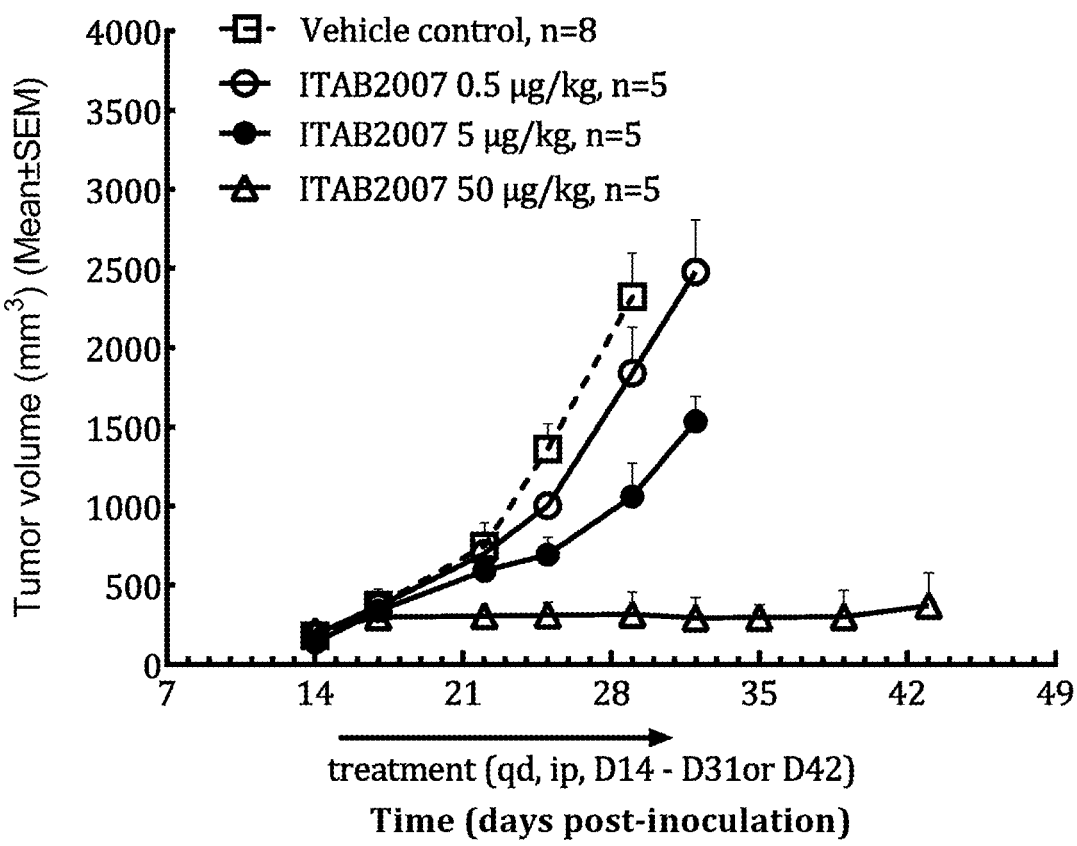
FIG. 7 depicts the growth inhibitory effect of ITAB2007 CD19×CD3 MSAP against subcutaneous Raji xenograft tumor in immune-reconstructed NOG mice inoculated with human PBMC. Vehicle injection (PBST) served as control. The results indicated that ITAB2007 inhibited Raji xenograft tumor growth in huPBMC engrafted mice in a concentration dependent manner.

FIG. 7 shows the growth inhibitory effect of ITAB2007 against subcutaneous Raji xenograft tumor in immune-reconstructed NOG mice inoculated with human PBMC. At the end of the study, the average tumor volumes were 2320.96±276.62 mm$^3$ (on day 29) for vehicle control group, 2477.04±331.34 mm$^3$ (on day 32) for ITAB2007 at 0.5 µg/kg group, 1534.02±159.21 mm$^3$ (on day 32) for ITAB2007 at 5 µg/kg group, and 370.05±207.68 mm$^3$ (on day 43) for ITAB2007 at 50 µg/kg group. The tumor growth inhibition rate (TGI %) was 23.0% (p=0.9999), 57.0% (p=0.5176), and 95.1% (p=0.0002) upon treatment with ITAB2007 at 0.5 µg/kg, 5 µg/kg, and 50 µg/kg on day 29, respectively.

Therefore, after Busulfan conditioning of the bone marrow in NOG mice, and reconstruction of the immune system using human PBMC, administration of CD19×CD3 MSAP (i.e., ITAB2007) could effectively inhibit in vivo growth of human burkitt's lymphoma cells Raji in mice, indicating that CD19×CD3 MSAP could mediate immune cells to kill tumor cells in vivo, and significantly inhibit tumor growth in a dose-dependent manner.

Example 8: Efficacy Assay of CD19×CD3 MSAPs on Mouse Survival Model with Intravenously Injected Reh Leukemia Tumor Xenograft and Human Primary T Cells (Immune-Reconstructed Mouse Model)

To examine the growth inhibitory effect of exemplary CD19×CD3 MSAPs (ITAB2007 and ITAB2009) on xenograft tumors, immunodeficient NOD/SCID mice intravenously injected with human Precursor B-cell (preB) acute lymphoblastic leukemia (ALL) Reh cells and human primary T cells were evaluated for MSAP in vivo efficacy of prolonged leukemia survival.

Eight to ten weeks old female NOD/SCID (NOD.CB17-Prkdc$^{scid}$/NcrCrl) mice were raised under SPF conditions (AAALAC accredited) at least one week before study began.

Pri-T cells were prepared according to the method described in Example 5, and resuspended in RPMI 1640 Medium (Gibco) containing 10% FBS (Gibco).

Reh cells were cultured in RPMI 1640 Medium (Gibco) containing 10% FBS (Gibco) in a 37° C., 5% CO$_2$ incubator.

Mice were inoculated intravenously via tail vein with $1.0 \times 10^7$ cells/mouse Reh cells in a volume of 0.2 mL/mouse on day 0, followed by reconstitution with $4.0 \times 10^6$ cells/ animal of in vitro cultured human primary T cells (Pri-T) intravenously via tail vein in a volume of 0.2 mL/mouse for a total of 4 injections on day 3, day 9, day 15, and day 21.

Thirty-seven NOD/SCID mice with Reh cancer cell inoculation and human primary T cell reconstitution were randomized into 3 groups for intraperitoneal treatment with vehicle (PBST; n=13), ITAB2009 (n=12), or ITAB2007 (n=12) after injection of human primary T cells on day 3. The dosing regimen of ITAB2009 and ITAB2007 was as follows: 50 µg/kg, q.d. for 3 days followed with 100 µg/kg, q.d. for 3 days per cycle, for a total of 4 cycles from day 3 to day 26, and initialized 2 hours after injection of human primary T cells. Clinical observation and survival were monitored and recorded daily.

Figure 8:
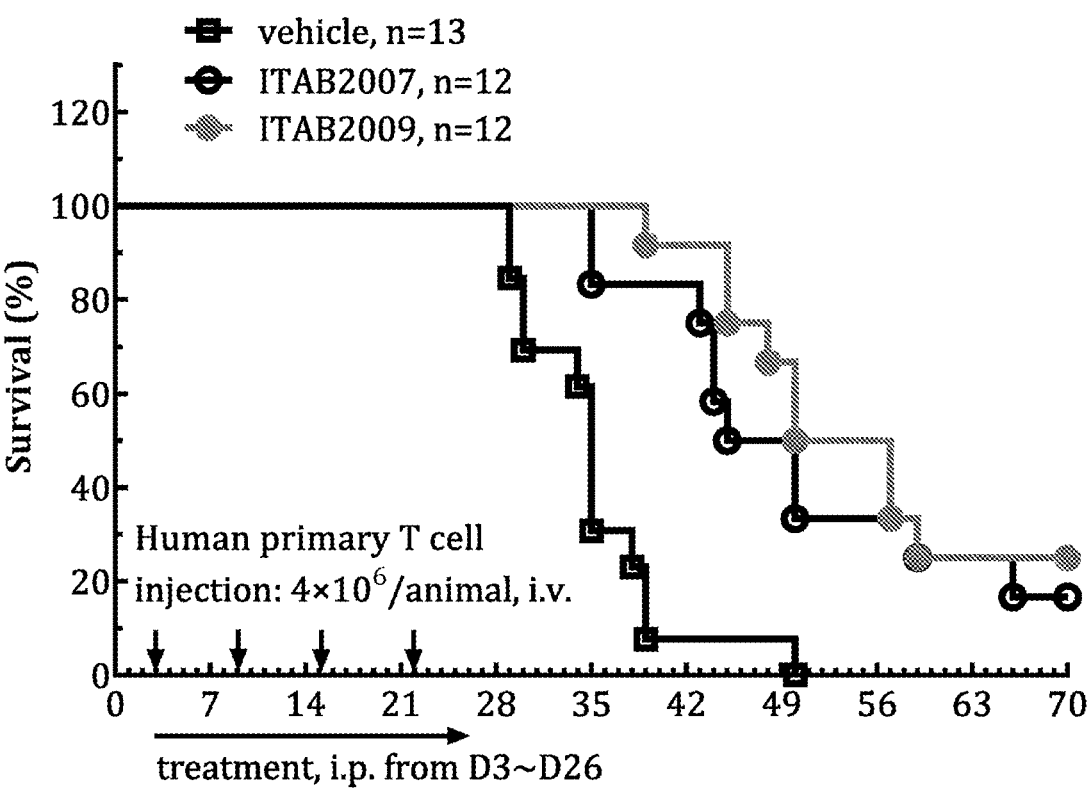
FIG. 8 depicts survival rate of Reh inoculated mice with immune system reconstructed with human primary T cells and under treatment with CD19×CD3 MSAP or vehicle control.

As shown in FIG. 8, the median survival of mice in the vehicle group was 35 days post tumor cell inoculation, with all mice died or euthanized by day 50. ITAB2009 or ITAB2007 CD19×CD3 MSAP treatment significantly prolonged mice survival, with a median survival of 53.5 days for ITAB2009 (p<0.0001, HR=0.2294) and 47.5 days for ITAB2007 (p=0.0003, HR=0.2977), as compared with the vehicle control.

In summary, the trivalent format ITAB2007 CD19×CD3 MSAP demonstrated great in vivo Reh cell (ALL cell line) killing efficacy, and significantly better potency compared to ITAB2009 in mediating Reh cell killing in vitro by human Pri-T cells. Further, ITAB2007 showed much better efficacy for in vitro and in vivo human B cell tumor killing, compared to bivalent format ITAB2009 CD19×CD3 MSAP. In summary, ITAB2007 demonstrated great potential to target low-CD19 expressing tumor cells.

All references mentioned in the present invention are incorporated herein by reference as if each of those references has been incorporated by reference individually. Although the description referred to particular embodiments, it will be clear to a person skilled in the art that the present invention may be practiced with variation of these specific details. Hence this invention should not be construed as limited to the embodiments set forth herein.

---

What is claimed is:

1. A multispecific antigen binding protein comprising:

(I) an anti-CD3 Fab fragment that specifically binds to CD3, wherein the anti-CD3 Fab fragment comprises:

(a) an immunoglobulin (Ig) heavy chain variable region (VH) and an Ig heavy chain constant region (CH1); and (b) an Ig light chain variable region (VL) and an Ig light chain constant region (CL);

(II) an anti-CD19 single chain variable fragment (scFv) that specifically binds to CD19, wherein the anti-CD19 scFv comprises a VH, wherein the VH of the anti-CD19 scFv comprises an HVR-H1 comprising the amino acid sequence of SEQ ID NO: 1, an HVR-H2 comprising the amino acid sequence of SEQ ID NO: 2, and an HVR-H3 comprising the amino acid sequence of SEQ ID NO: 3; and wherein the anti-CD19 scFv comprises a VL, wherein the VL of the anti-CD19 scFv comprises an HVR-L1 comprising the amino acid sequence of SEQ ID NO: 47, an HVR-L2 comprising the amino acid sequence of SEQ ID NO: 48, and an HVR-L3 comprising the amino acid sequence of SEQ ID NO: 49; and (III) an optional linker connecting the anti-CD3 Fab fragment and the anti-CD19 scFv; and wherein:

(i) the anti-CD19 scFv is connected to the N-terminus of the VH or the VL of the anti-CD3 Fab fragment; or (ii) the multispecific antigen binding protein comprises a first anti-CD19 scFv and a second anti-CD19 scFv, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment.

2. The multispecific antigen binding protein of claim 1, wherein the anti-CD19 scFv is fused to the N-terminus of the VH of the anti-CD3 Fab fragment.

3. The multispecific antigen binding protein of claim 1, wherein the anti-CD19 scFv is fused to the N-terminus of the VL of the anti-CD3 Fab fragment.

4. The multispecific antigen binding protein of claim 1, wherein the multispecific antigen binding protein comprises a first anti-CD19 scFv and a second anti-CD19 scFv, wherein the first anti-CD19 scFv is fused to the N-terminus of the VH of the anti-CD3 Fab fragment, and wherein the second anti-CD19 scFv is fused to the N-terminus of the VL of the anti-CD3 Fab fragment.

5. The multispecific antigen binding protein of claim 4, wherein the VH of the anti-CD3 Fab fragment comprises an HVR-H1 comprising the amino acid sequence of SEQ ID NO: 9, an HVR-H2 comprising the amino acid sequence of SEQ ID NO: 10, and an HVR-H3 comprising the amino acid sequence of SEQ ID NO: 11; and wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14.

6. The multispecific antigen binding protein of claim 5, wherein the first anti-CD19 scFv and the second anti-CD19 scFv have the same amino acid sequence.

7. The multispecific antigen binding protein of claim 6, wherein the first anti-CD19 scFv and the second anti-CD19 scFv each comprises the amino acid sequence of SEQ ID NO: 51.

8. The multispecific antigen binding protein of claim 4, wherein the VH of the first anti-CD19 scFv and the VH of the second anti-CD19 scFv each comprises the amino acid sequence of SEQ ID NO: 7, and wherein the VL of the first anti-CD19 scFv and the VL of the second anti-CD19 scFv each comprises the amino acid sequence of SEQ ID NO: 50.

9. The multispecific antigen binding protein of claim 4, wherein the first anti-CD19 scFv and the second anti-CD19 scFv have the same amino acid sequence.

10. The multispecific antigen binding protein of claim 1, wherein the VH of the anti-CD3 Fab fragment comprises an HVR-H1 comprising the amino acid sequence of SEQ ID NO: 9, an HVR-H2 comprising the amino acid sequence of SEQ ID NO: 10, and an HVR-H3 comprising the amino acid sequence of SEQ ID NO: 11; and wherein the VL of the anti-CD3 Fab fragment comprises an HVR-L1 comprising the amino acid sequence of SEQ ID NO: 12, an HVR-L2 comprising the amino acid sequence of SEQ ID NO: 13, and an HVR-L3 comprising the amino acid sequence of SEQ ID NO: 14.

11. The multispecific antigen binding protein of claim 10, wherein the VH of the anti-CD3 Fab fragment comprises the amino acid sequence of SEQ ID NO: 15; and wherein the VL of the anti-CD3 Fab fragment comprises the amino acid sequence of SEQ ID NO: 16.

12. The multispecific antigen binding protein of claim 11, wherein the anti-CD3 Fab fragment comprises a heavy chain polypeptide comprising the amino acid sequence of SEQ ID NO: 57, and a light chain polypeptide comprising the amino acid sequence of SEQ ID NO: 58.

13. The multispecific antigen binding protein of claim 12, wherein:

i) the multispecific antigen binding protein comprises an anti-CD19 scFv connected to the N-terminus of the VH of the anti-CD3 Fab fragment via a linker to form a first polypeptide of the multispecific antigen binding protein, wherein the first polypeptide of the multispecific antigen binding protein comprises the amino acid sequence of SEQ ID NO: 53, and wherein the multispecific antigen binding protein comprises a second polypeptide comprising the amino acid sequence of SEQ ID NO: 58; or ii) the multispecific antigen binding protein comprises a first polypeptide comprising the amino acid sequence of SEQ ID NO: 57, wherein the multispecific antigen binding protein comprises an anti-CD19 scFv connected to the N-terminus of the VL of the anti-CD3 Fab fragment via a linker to form a second polypeptide of the multispecific antigen binding protein, and wherein the second polypeptide of the multispecific antigen binding protein comprises the amino acid sequence of SEQ ID NO: 54.

14. The multispecific antigen binding protein of claim 12, wherein the anti-CD19 scFv, or the first anti-CD19 scFv and/or the second anti-CD19 scFv, comprises the amino acid sequence of SEQ ID NO: 51.

15. The multispecific antigen binding protein of claim 1, wherein the VH of the anti-CD19 scFv, or the VH of the first anti-CD19 scFv and/or the second anti-CD19 scFv, comprises the amino acid sequence of SEQ ID NO: 7; and wherein the VL of the anti-CD19 scFv, or the VL of the first anti-CD19 scFv and/or the second anti-CD19 scFv, comprises the amino acid sequence of SEQ ID NO: 50.

16. The multispecific antigen binding protein of claim 1, wherein the anti-CD19 scFv, or the first anti-CD19 scFv and/or the second anti-CD19 scFv, comprises the amino acid sequence of SEQ ID NO: 51.

17. The multispecific antigen binding protein of claim 1, wherein the linker comprises the amino acid sequence of any one of SEQ ID NOs: 20-22, 29, and 31-44.

18. An isolated nucleic acid encoding the multispecific antigen binding protein of claim 1.

19. A pharmaceutical composition comprising the multispecific antigen binding protein of claim 1, and optionally a pharmaceutically acceptable carrier.

20. A method of treating a CD19-positive cancer in an individual, comprising administering to the individual an effective amount of the pharmaceutical composition of claim 19.

21. The method of claim 20, wherein the CD19-positive cancer is selected from the group consisting of acute myeloid leukemia (AML), chronic myelogenous leukemia (CML), myelodysplastic syndrome (MDS), acute B lymphoblastic leukemia (B-ALL), diffuse large B cell lymphoma (DLBCL), follicular lymphoma, chronic lymphocytic leukemia (CLL), hairy cell leukemia (HCL), blastic plasmacytoid dendritic cell neoplasm (BPDCN), non-Hodgkin's lymphoma (NHL), Hodgkin's lymphoma, systemic mastocytosis, and Burkitt's lymphoma.

22. A multispecific antigen binding protein comprising:

(I) an anti-CD3 Fab fragment that specifically binds to CD3, wherein the anti-CD3 Fab fragment comprises:
  (a) a VH and a CH1; and
  (b) a VL and a CL;

(II) a first anti-CD19 scFv and a second anti-CD19 scFv; and (III) a first linker and a second linker;
  wherein the first anti-CD19 scFv is fused to the N-terminus of the VH of the anti-CD3 Fab fragment via the first linker to form a first polypeptide of the multispecific antigen binding protein, and the second anti-CD19 scFv is fused to the N-terminus of the VL of the anti-CD3 Fab fragment via the second linker to form a second polypeptide of the multispecific antigen binding protein;
  wherein the first polypeptide of the multispecific antigen binding protein comprises the amino acid sequence of SEQ ID NO: 53, and wherein the second polypeptide of the multispecific antigen binding protein comprises the amino acid sequence of SEQ ID NO: 54.

23. A pharmaceutical composition comprising the multispecific antigen binding protein of claim 22, and optionally a pharmaceutically acceptable carrier.

24. A multispecific antigen binding protein comprising:

(I) an anti-CD3 Fab fragment that specifically binds to CD3, wherein the anti-CD3 Fab fragment comprises:
  (a) a VH and a CH1; and
  (b) a VL and a CL;

(II) a first anti-CD19 scFv and a second anti-CD19 scFv; and (III) a first linker and a second linker;

wherein the first anti-CD19 scFv is fused to the N-terminus of the VH of the anti-CD3 Fab fragment via the first linker to form a first polypeptide of the multispecific antigen binding protein, and the second anti-CD19 scFv is fused to the N-terminus of the VL of the anti-CD3 Fab fragment via the second linker to form a second polypeptide of the multispecific antigen binding protein;

wherein the first polypeptide of the multispecific antigen binding protein comprises the amino acid sequence of SEQ ID NO: 60, and wherein the second polypeptide of the multispecific antigen binding protein comprises the amino acid sequence of SEQ ID NO: 61.

25. A pharmaceutical composition comprising the multispecific antigen binding protein of claim 24, and optionally a pharmaceutically acceptable carrier.

26. A multispecific antigen binding protein, wherein:

i) the multispecific antigen binding protein comprises a first polypeptide comprising the amino acid sequence of SEQ ID NO: 57, wherein the multispecific antigen binding protein comprises an anti-CD19 scFv connected to the N-terminus of the VL of an anti-CD3 Fab fragment via a linker to form a second polypeptide of the multispecific antigen binding protein, wherein the second polypeptide of the multispecific antigen binding protein comprises the amino acid sequence of SEQ ID NO: 61;

ii) the multispecific antigen binding protein comprises an anti-CD19 scFv connected to the N-terminus of the VH of an anti-CD3 Fab fragment via a linker to form a first polypeptide of the multispecific antigen binding protein, wherein the first polypeptide of the multispecific antigen binding protein comprises the amino acid sequence of SEQ ID NO: 60, and wherein the multispecific antigen binding protein comprises a second polypeptide comprising the amino acid sequence of SEQ ID NO: 58;

iii) the multispecific antigen binding protein comprises a first anti-CD19 scFv connected to the N-terminus of the VH of an anti-CD3 Fab fragment via a first linker to form a first polypeptide of the multispecific antigen binding protein, wherein the first polypeptide of the multispecific antigen binding protein comprises the amino acid sequence of SEQ ID NO: 53, wherein the multispecific antigen binding protein comprises a second anti-CD19 scFv connected to the N-terminus of the VL of the anti-CD3 Fab fragment via a second linker to form a second polypeptide of the multispecific antigen binding protein, and wherein the second polypeptide of the multispecific antigen binding protein comprises the amino acid sequence of SEQ ID NO: 61; or iv) the multispecific antigen binding protein comprises an anti-CD19 scFv connected to the N-terminus of the VH of an anti-CD3 Fab fragment via a first linker to form a first polypeptide of the multispecific antigen binding protein, wherein the first polypeptide of the multispecific antigen binding protein comprises the amino acid sequence of SEQ ID NO: 60, wherein the multispecific antigen binding protein comprises a second anti-CD19 scFv connected to the N-terminus of the VL of the anti-CD3 Fab fragment via a second linker to form a second polypeptide of the multispecific antigen binding protein, and wherein the second polypeptide of the multispecific antigen binding protein comprises the amino acid sequence of SEQ ID NO: 54.

* * * * *